United States Patent
Parham et al.

(10) Patent No.: US 8,835,626 B2
(45) Date of Patent: Sep. 16, 2014

(54) MATERIALS FOR ORGANIC ELECTROLUMINESCENT DEVICES

(75) Inventors: Amir Hossain Parham, Frankfurt am Main (DE); Christof Pflumm, Frankfurt am Main (DE); Teresa Mujica-Fernaud, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 25 days.

(21) Appl. No.: 13/636,752

(22) PCT Filed: Feb. 25, 2011

(86) PCT No.: PCT/EP2011/000944
§ 371 (c)(1),
(2), (4) Date: Sep. 24, 2012

(87) PCT Pub. No.: WO2011/116865
PCT Pub. Date: Sep. 29, 2011

(65) Prior Publication Data
US 2013/0012700 A1    Jan. 10, 2013

(30) Foreign Application Priority Data
Mar. 25, 2010   (DE) .................. 10 2010 012 738

(51) Int. Cl.
| C07D 471/16 | (2006.01) |
| --- | --- |
| C07D 471/22 | (2006.01) |
| C07D 487/06 | (2006.01) |
| C07D 487/16 | (2006.01) |
| C07D 487/20 | (2006.01) |
| C07D 487/22 | (2006.01) |
| C07D 495/22 | (2006.01) |
| C07D 513/12 | (2006.01) |
| C07D 513/22 | (2006.01) |
| C07D 513/16 | (2006.01) |
| C09B 57/00 | (2006.01) |
| C07F 7/08 | (2006.01) |
| H01L 51/00 | (2006.01) |
| C07F 9/6584 | (2006.01) |
| C09B 57/10 | (2006.01) |
| H01L 51/50 | (2006.01) |

(52) U.S. Cl.
CPC .......... *C07D 471/16* (2013.01); *C07D 487/20* (2013.01); *C07D 513/16* (2013.01); *C09B 57/007* (2013.01); *C07F 7/0814* (2013.01); *C07D 487/06* (2013.01); *H01L 51/0072* (2013.01); *C07D 471/22* (2013.01); *H01L 51/5016* (2013.01); *C07D 513/22* (2013.01); *C07F 9/65848* (2013.01); *C07D 495/22* (2013.01); *C09B 57/00* (2013.01); *C07D 487/16* (2013.01); *Y02E 10/549* (2013.01); *C07D 487/22* (2013.01); *H01L 51/5012* (2013.01); *C09B 57/10* (2013.01)

USPC ........................... 540/492; 540/494; 540/555

(58) Field of Classification Search
USPC ......................... 540/492, 494, 555
See application file for complete search history.

(56) References Cited

U.S. PATENT DOCUMENTS

| 4,521,534 A | 6/1985 | Gauthier et al. |
| 4,596,799 A | 6/1986 | Wasley |
| 2009/0302752 A1 | 12/2009 | Parham et al. |

FOREIGN PATENT DOCUMENTS

WO    WO-2008/086851 A1    7/2008

OTHER PUBLICATIONS

Klunder, Janice M., "Sommelet-Hauser Rearrangement of an Ammonium Ylide Derived from the HIV-1 Reverse Transcriptase Inhibitor Nevirapine", J. Heterocyclic Chem., vol. 32, (1995), pp. 1687-191.

Shafiee, A., et al., "Syntheses of 7-Phenyl-5H-Thiazlo[5,4-e]Pyrrolo[1,2-a][1,4]Diazepin-10(9H)One, 7-Phenyl-5H-Thiazlo[5,4-e][1,2,3,4]Tetrazolo[5,1-c]-Pyrrolo[1,2-a][1,4]Diazepine and 7-Phenyl-5H-Thiazlo[5,4-e]-[1,3,4]Triazolo[5,1-c]Pyrrolo[1,2-a][1,4]Diazepines [1]", J. Heterocylic Chem., vol. 39, (2002), pp. 213-216.

Duceppe, Jean-Simon, et al., "Synthesis of Novel Imidazo[1,2-a]Pyrrolo[2,1-c][1,4]Benzodiazepines and Pyrimido[1,2-a]Pyrrolo[2,1-c][1,4]Benzodiazepines", J. Heterocyclic Chem., vol. 22, (1985), pp. 305-310.

Beugelmans-Verrier, Michele, et al., Synthesis of Pentacyclic β-Carboline and 1,4-Benzodiazepine Hybrid Molecules by Dehydrogenation-Transamidation of Quinazolino-Tetrahydro-β-Carbolines, Tetrahedron, vol. 43, No. 15, (1987), pp. 3465-3470.

Stefancich, et al., "Research on Nitrogen Containing Heterocyclic Compounds. XVIII. Synthesis of 9H-Pyrrolo[2,1-c]-s-Triazolo[4,3-a][1,4]Benzodiazepine, a Novel Tetracyclic Ring of Pharmaceutical Interest", J. Heterocyclic Chem., vol. 29, (1992), pp. 1005-1007.

Massa, Silvio, et al., "Research on Nitrogen Containing Heterocyclic Compounds. XX. Synthesis of 8H-Imidazo[5,1-c-]Pyrrolo-'1,2-a][1,4]Benzodiazepine and its 6-Derivatives", J. Heterocyclic Chem., vol. 30, (1993), pp. 749-753.

Silvestri, Romano, et al., "Synthesis and Anti-HIV Activity of 10,11-Dihydropyrrolo [1,2-b][1,2,5]Benzothiadiazepine-11-Acetic Acid 5,5-Dioxide Derivatives and Related Compounds", II Farmaco, vol. 51, No. 6, (1996), pp. 425-430.

Danieli, Bruno, et al., "Quinazolinocarboline Alkaloids Chemistry: Reactivity of Euxylophorines—Part 1", Heterocycles, vol. 12, No. 3, (1979), pp. 353-357.

International Search Report for PCT/EP2011/000944 mailed Apr. 15, 2011.

*Primary Examiner* — Bruck Kifle
(74) *Attorney, Agent, or Firm* — Drinker Biddle & Reath LLP

(57) ABSTRACT

The present invention relates to compounds of the formula (1) which are suitable for use in electronic devices, in particular organic electroluminescent devices.

12 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2011/000944, filed Feb. 25, 2011, which claims benefit of German application 10 2010 012 738.8, filed Mar. 25, 2010.

The present invention relates to materials for use in electronic devices, in particular in organic electroluminescent devices.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescent emitters. In general, however, there is still a need for improvement in OLEDs, in particular also in OLEDs which exhibit triplet emission (phosphorescence), for example with respect to efficiency, operating voltage and lifetime. This applies, in particular, to OLEDs which emit in the relatively short-wave region, for example green.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is also still a need for improvement in these materials for fluorescent OLEDs.

In accordance with the prior art, ketones (for example in accordance with WO 2004/093207 or WO 2010/006680) or phosphine oxides (for example in accordance with WO 2005/003253), inter alia, are used as matrix materials for phosphorescent emitters. However, there is still a need for improvement on use of these matrix materials as in the case of other matrix materials, in particular with respect to the efficiency and lifetime of the device.

In accordance with the prior art, carbazole derivatives, for example in accordance with WO 2005/039246, US 2005/0069729, JP 2004/288381, EP 1205527 or WO 2008/086851, and indolocarbazole derivatives, for example in accordance with WO 2007/063754 or WO 2008/056746, are furthermore employed as matrix materials for phosphorescent emitters in organic electroluminescent devices. These have the disadvantage that they are frequently very oxidation-sensitive, which impairs the preparation, purification and storage of the materials and the long-term stability of solutions comprising the materials. Further improvements are desirable here, likewise with respect to the efficiency, lifetime and thermal stability of the materials.

The object of the present invention is the provision of compounds which are suitable for use in a fluorescent or phosphorescent OLED, in particular a phosphorescent OLED, for example as matrix material or as hole-transport/electron-blocking material or exciton-blocking material or as electron-transport or hole-blocking material. In particular, the object of the present invention is to provide matrix materials which are suitable for green- and red-, but also for blue-phosphorescent OLEDs.

Surprisingly, it has been found that the compounds described in greater detail below achieve this object and result in significant improvements in the organic electroluminescent device, in particular with respect to the lifetime, efficiency and operating voltage. This applies, in particular, to red- and green-phosphorescent electroluminescent devices, in particular on use of the compounds according to the invention as matrix material. The materials according to the invention are furthermore distinguished by improved oxidation stability in solution and by high temperature stability. The present invention therefore relates to these materials and to organic electroluminescent devices which comprise compounds of this type.

The present invention relates to a compound of the following formula (1):

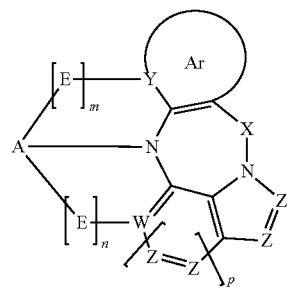

formula (1)

where the following applies to the symbols and indices used:

X is C=O, C(R)$_2$, NR, O, S, C=S, C=NR, C=C(R)$_2$, Si(R)$_2$, BR, PR, P(=O)R, SO or SO$_2$;

Y is, identically or differently, W, as defined below, or is NR, O or S, with the proviso that Y=C if a group E is bonded to the group Y;

W is on each occurrence, identically or differently, CR or N, with the proviso that not more than three groups W in a ring stand for N, and with the further proviso that W=C if a group E is bonded to this group W;

Z is, identically or differently on each occurrence, CR or N; or two adjacent groups Z stand for a group of the formula (2)

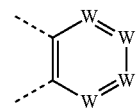

formula (2)

in which the dashed bonds indicate the linking of this unit;

E is, identically or differently on each occurrence, a single bond, C(R)$_2$, NR, O, S, C=O, C=S, C=NR, C=C(R)$_2$, Si(R)$_2$, BR, PR, P(=O)R, SO or SO$_2$;

Ar is, together with the group Y and the two carbon atoms, an aryl or heteroaryl group having 5 to 30 aromatic ring atoms, which may be substituted by one or more radicals R;

A is R if m=n=0, and is an aryl or heteroaryl group having 5 to 30 aromatic ring atoms, which may in each case be substituted by R, or a group —CR=CR—, —CR=N— or —N=N— if an index m or n=1 and the other index m or n=0, or is an aryl or heteroaryl group having 5 to 30 aromatic ring atoms, which may in each case be substituted by R, if the indices m=n=1;

R is selected on each occurrence, identically or differently, from the group consisting of H, D, F, Cl, Br, I, CN, $NO_2$, $N(Ar^1)_2$, $N(R^1)_2$, $C(=O)Ar^1$, $C(=O)R^1$, $P(=O)(Ar^1)_2$, a straight-chain alkyl, alkoxy or thioalkyl group having 1 to 40 C atoms or a branched or cyclic alkyl, alkoxy or thio- alkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C=CR^1$, $C≡C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, an aromatic or heteroaromatic ring system having 5 to 80, preferably 5 to 60, aromatic ring atoms, which may in each case be substituted by one or more radicals $R^1$, an aryloxy or heteroaryloxy group having 5 to 60 aromatic ring atoms, which may be substituted by one or more radicals $R^1$, or a combination of these systems, where two or more adjacent substituents R may optionally form a monocyclic or polycyclic, aliphatic, aromatic or heteroaromatic ring system, which may be substituted by one or more radicals $R^1$;

$R^1$ is selected on each occurrence, identically or differently, from the group consisting of H, D, F, Cl, Br, I, CN, $NO_2$, $N(Ar^1)_2$, $N(R^2)_2$, $C(=O)Ar$, $C(=O)R^2$, $P(=O)(Ar^1)_2$, a straight-chain alkyl, alkoxy or thioalkyl group having 1 to 40 C atoms or a branched or cyclic alkyl, alkoxy or thio- alkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which may be substituted by one or more radicals $R^2$, or a combination of these systems, where two or more adjacent substituents R may optionally form a monocyclic or polycyclic, aliphatic, aromatic or heteroaromatic ring system, which may be substituted by one or more radicals $R^2$;

$R^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic, aromatic or heteroaromatic ring system with one another;

$Ar^1$ is on each occurrence, identically or differently, an aromatic or heteroaromatic ring system having 5-30 aromatic ring atoms, which may be substituted by one or more non-aromatic radicals $R^2$; two radicals $Ar^1$ which are bonded to the same N atom or P atom may also be bridged to one another here by a single bond or a bridge selected from N(R), $C(R^2)_2$ or O;

m, n are, identically or differently on each occurrence, 0 or 1, where, for m=0, a group R instead of the group E is bonded to A, and where, for n=0, a group R instead of the group E is bonded to A;

p is 0 or 1, where, for p=0, a group R instead of the group Z=Z is bonded to each of the carbon atom and to W, with the proviso that p=1 if m=n=0.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl, are, by contrast, not referred to as an aryl or heteroaryl group, but instead as an aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom. Thus, for example, systems such as fluorene, 9,9'-spirobifluorene, 9,9- diarylfluorene, triarylamine, diaryl ether, stilbene, etc., are also intended to be taken to be aromatic ring systems in the sense of this invention, as are systems in which two or more aryl groups are interrupted, for example, by a short alkyl group.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neo- hexyl, cyclohexyl, n-heptyl, cycloheptyl, n-octyl, cyclooctyl, 2-ethylhexyl, trifluoromethyl, pentafluoroethyl, 2,2,2-trifluo- roethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2- trifluoroethoxy. A thioalkyl group having 1 to 40 C atoms is taken to mean, in particular, methylthio, ethylthio, n-propy- lthio, i-propylthio, n-butylthio, i-butylthio, s-butylthio, t-bu- tylthio, n-pentylthio, s-pentylthio, n-hexylthio, cyclohexy- lthio, n-heptylthio, cycloheptylthio, n-octylthio, cyclooctylthio, 2-ethylhexylthio, trifluoromethylthio, pen- tafluoroethylthio, 2,2,2-trifluoroethylthio, ethenylthio, pro- penylthio, butenylthio, pentenylthio, cyclopentenylthio, hex- enylthio, cyclohexenylthio, heptenylthio, cycloheptenylthio, octenylthio, cyclooctenylthio, ethynylthio, propynylthio, butynylthio, pentynylthio, hexynylthio, heptynylthio or octy- nylthio. In general, alkyl, alkoxy or thioalkyl groups in accor- dance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, furthermore preferably F or CN, particularly preferably CN.

An aromatic or heteroaromatic ring system having 5-80 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis-or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

In a preferred embodiment of the invention, X stands for C=O, $CR_2$, S, O or $SO_2$, particularly preferably for C=O or $SO_2$.

In a further preferred embodiment of the invention, E stands, identically or differently on each occurrence, for a single bond, $CR_2$, C=O, NR, O or S, particularly preferably for a single bond, $CR_2$, C=O or NR, very particularly preferably for a single bond, $CR_2$ or C=O, in particular for a single bond.

In yet a further preferred embodiment of the invention, the group A stands for an aryl or heteroaryl group having 5 to 16, in particular 5 to 10, aromatic ring atoms, which may in each case be substituted by one or more radicals R, or for a group of the formula —CR=CR—, —CR=N— or —N=N—.

In a particularly preferred embodiment of the invention, the group A stands for a group of the following formula (3), (4), (5) or (6):

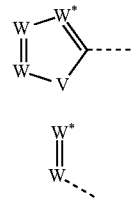

formula (3)

formula (4)

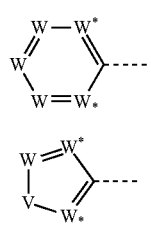

formula (5)

formula (6)

where the dashed bond indicates the link to N, * indicates the position of the link to E if a group E is present, and W has the meaning given above. W here is equal to C if a group E is bonded at this position. Furthermore, V stands for NR, O or S.

In a further preferred embodiment of the invention, the unit Z=Z in the five-membered ring of the formula (1) stands for a group of the formula (2) given above. Furthermore, the unit Z=Z in the six-membered ring of the formula (1) preferably stands for —CR=CR— or —CR=N—, in particular for —CR=CR—.

In a further preferred embodiment of the invention, the group Ar stands for a group of one of the following formulae (7), (8), (9) or (10):

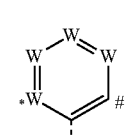

formula (7)

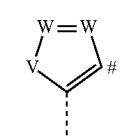

formula (8)

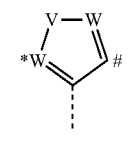

formula (9)

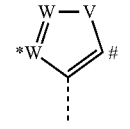

formula (10)

where the dashed bond indicates the link to N, # indicates the position of the link to X, * indicates the position of the link to E if a group E is present, and W and V have the meanings given above. W here is equal to C if a group E is bonded at this position.

In yet a further preferred embodiment of the invention, at least one index m or n=1. Particularly preferably, m+n=1.

In yet a further preferred embodiment of the invention, the index p=1.

In a particularly preferred embodiment of the invention, the preferences given above occur simultaneously. Particular preference is therefore given to compounds of the formula (1) for which:

X is C=O, $CR_2$, S, O or $SO_2$;

E is, identically or differently on each occurrence, a single bond, $CR_2$, C=O, NR, O or S;

A is an aryl or heteroaryl group having 5 to 16 aromatic ring atoms, which may in each case be substituted by one or more radicals R, or a group —CR=CR—, —CR=N— or —N=N—;

Z=Z in the five-membered ring of the formula (1) stands for a group of the formula (2) given above;

Ar stands for a group of one of the following formulae (7) to (10):

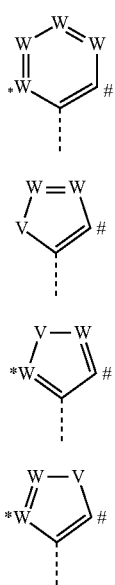

formula (7)

formula (8)

formula (9)

formula (10)

where the dashed bond indicates the link to N, # indicates the position of the link to X, * indicates the position of the link to E if a group E is present, and W has the meaning given above; W here is equal to C if a group E is bonded at this position; furthermore, V stands for NR, O, S or $CR_2$;

m, n are, identically or differently on each occurrence, 0 or 1, where at least one index m or n=1.

In a very particularly preferred embodiment of the invention, the following applies to compounds of the formula (1):

X is C=O or $SO_2$;

E is, identically or differently on each occurrence, a single bond, $CR_2$, C=O or NR, preferably a single bond, $CR_2$ or C=O, particularly preferably a single bond;

A stands for a group of one of the following formulae (3) to (6):

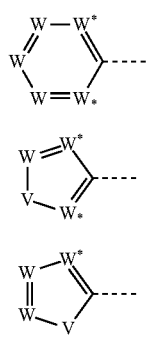

formula (3)

formula (4)

formula (5)

formula (6)

where the dashed bond indicates the link to Y, * indicates the position of the link to E if a group E is present, and W and V have the meanings given above; W here is equal to C if a group E is bonded at this position;

Z=Z in the five-membered ring of the formula (1) stands for a group of the formula (2) given above and in the six-membered ring of the formula (1) stands for CR=CR or CR=N;

Ar stands for a group of one of the formulae (7) to (10) given above; m, n are, identically or differently, 0 or 1, where m+n=1;

p is equal to 1.

Particularly preferred embodiments of the invention are therefore compounds of the following formulae (11) to (37):

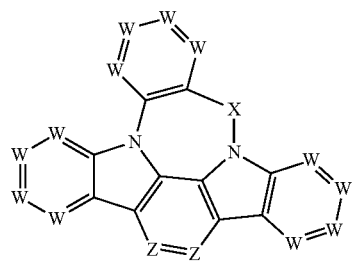

formula (11)

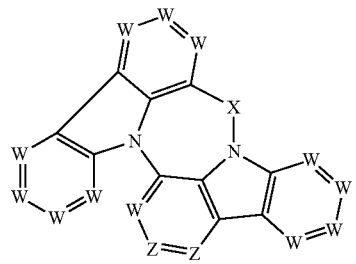

formula (12)

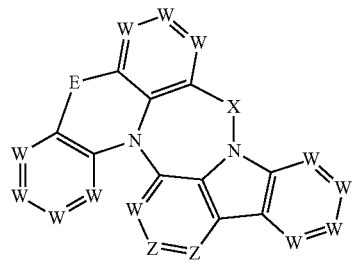

formula (13)

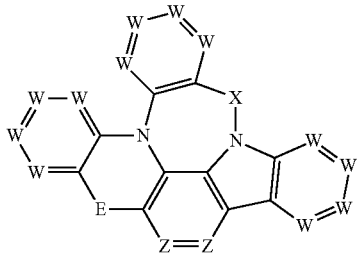

formula (14)

formula (15)
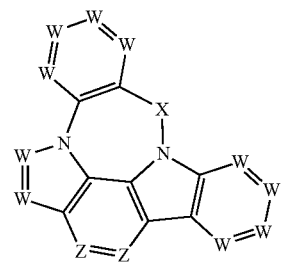
formula (16)
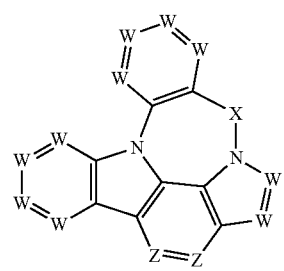
formula (17)
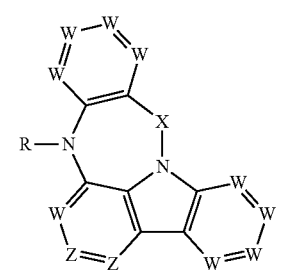
formula (18)
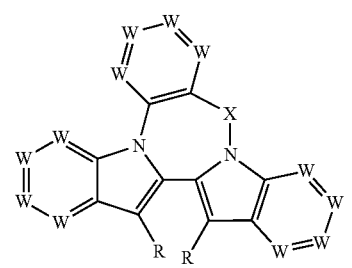
formula (19)
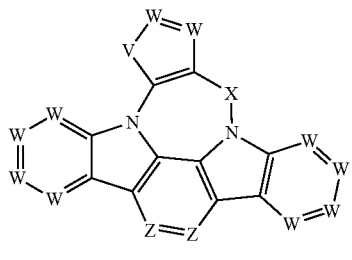
formula (20)
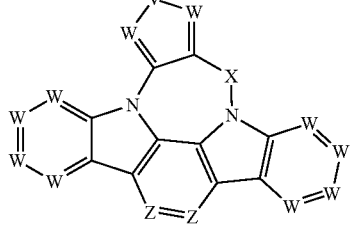
formula (21)
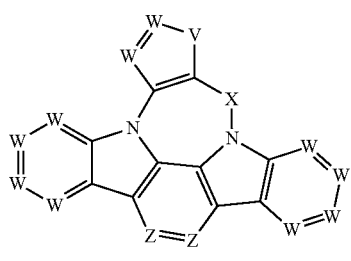
formula (22)
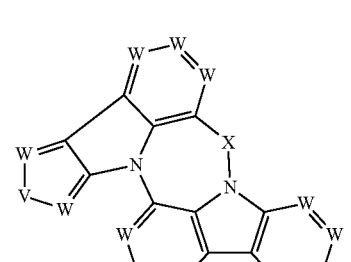
formula (23)
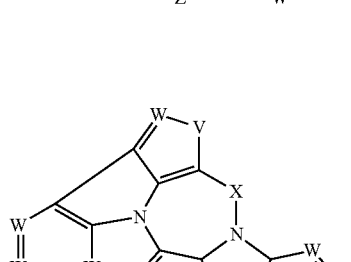
formula (24)
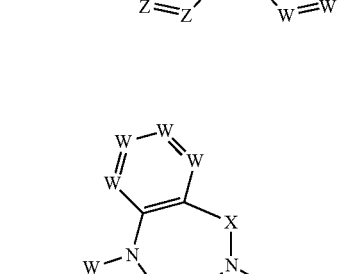
formula (25)
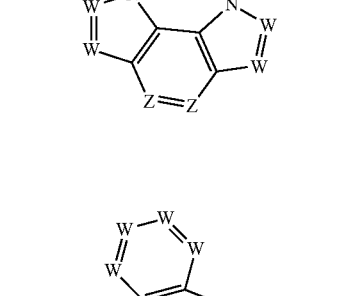

formula (26)
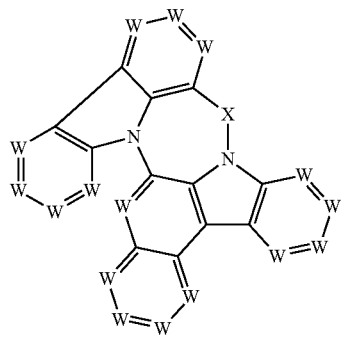
formula (27)
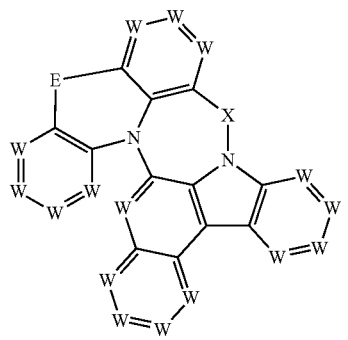
formula (28)
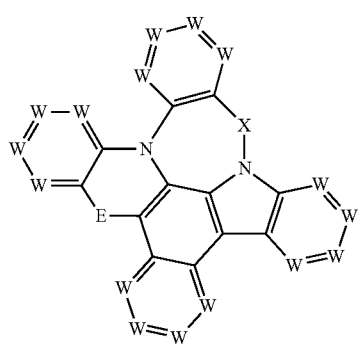
formula (29)
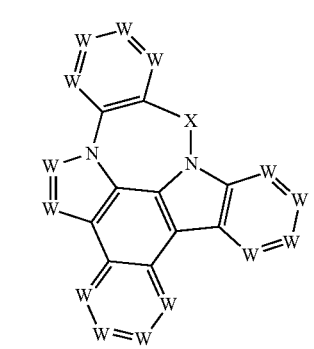
formula (30)
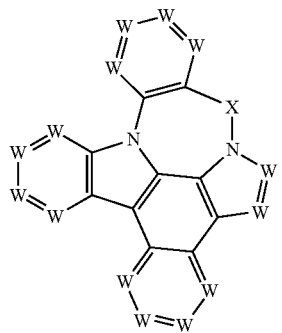
formula (31)
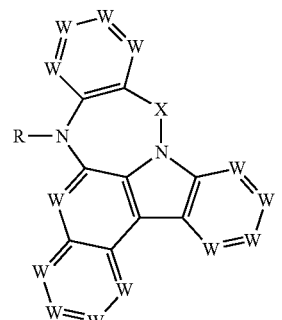
formula (32)
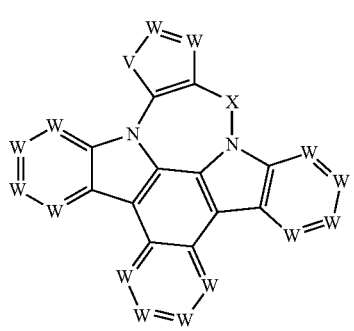
formula (33)
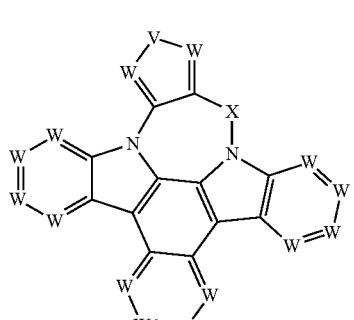
formula (34)
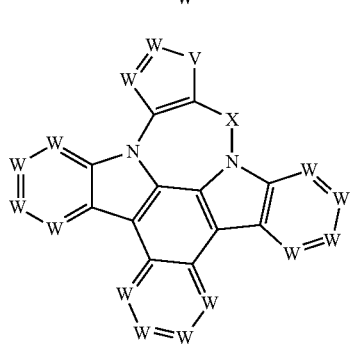

formula (35)

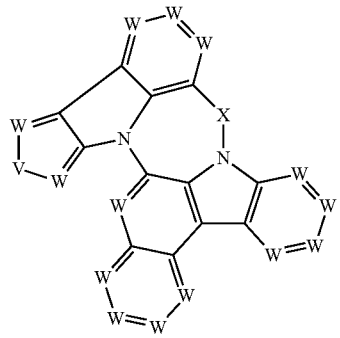

formula (12a)

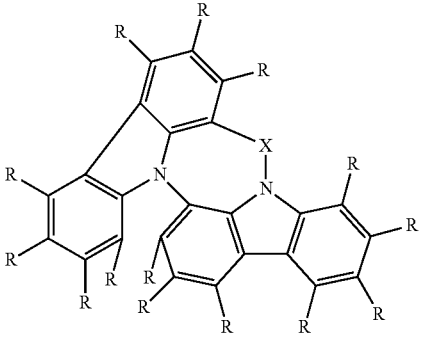

formula (36)

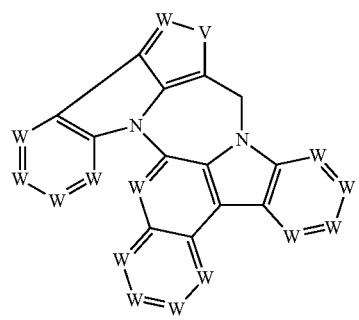

formula (13a)

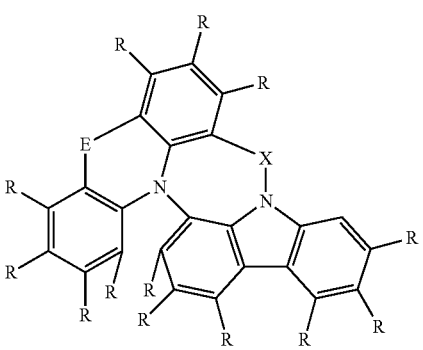

formula (37)

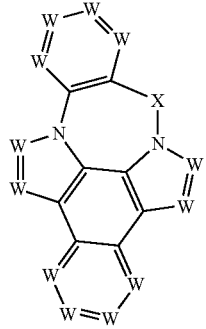

formula (14a)

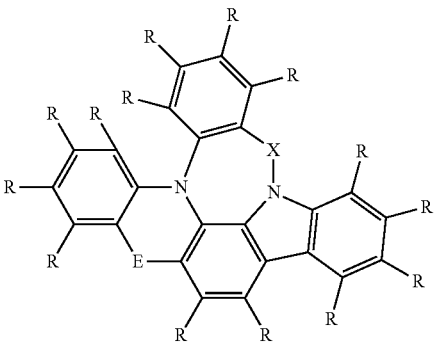

where the symbols used have the meanings given above.

In a further preferred embodiment of the compounds of the formulae (11) to (37), a total of a maximum of one symbol W or Z per ring stands for N and the remaining symbols W and Z stand for CR. In a particularly preferred embodiment of the invention, all symbols W and Z stand for CR. Particular preference is therefore given to the compounds of the following formulae (11a) to (37a):

formula (11a)

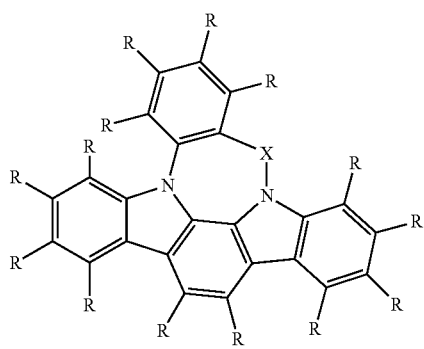

formula (15a)

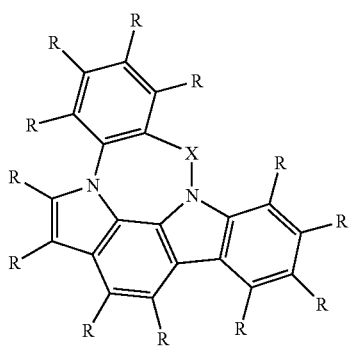

formula (16a)
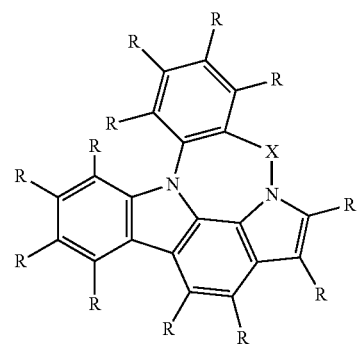
formula (17a)
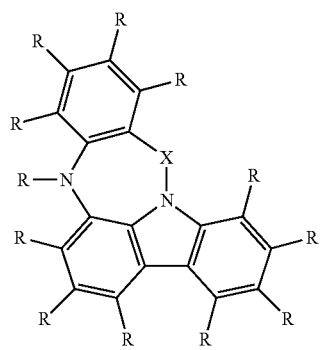
formula (18a)
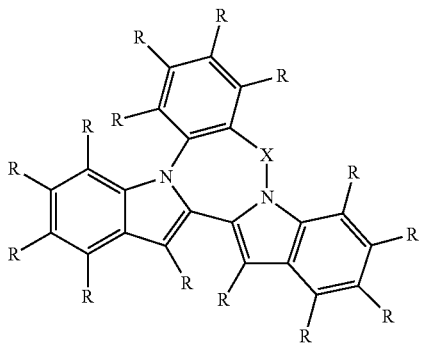
formula (19a)
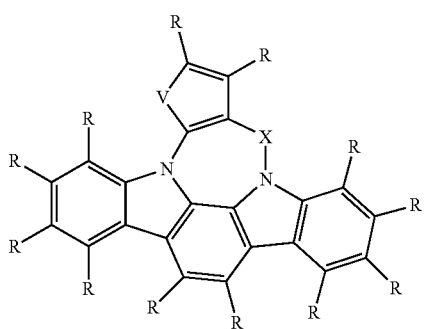
formula (20a)
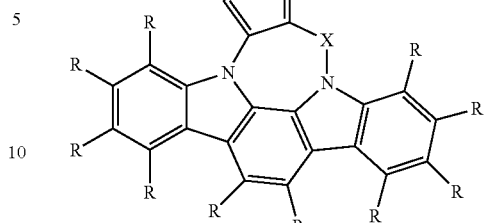
formula (21a)
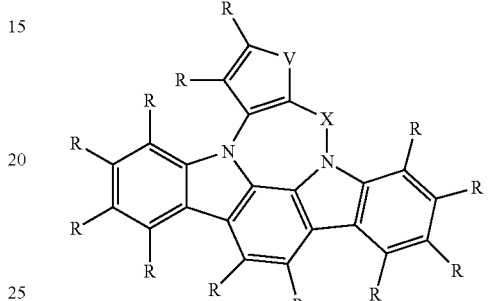
formula (22a)
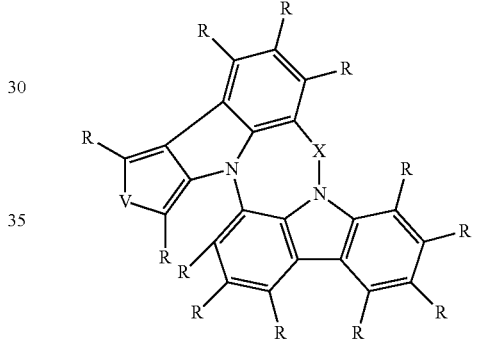
formula (23a)
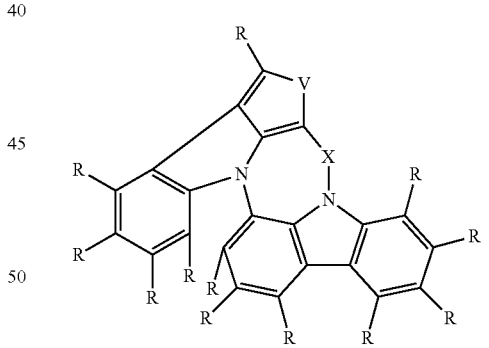
formula (24a)
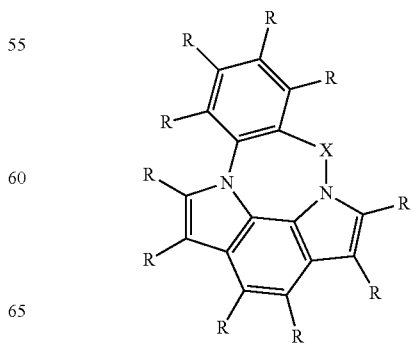

formula (25a)
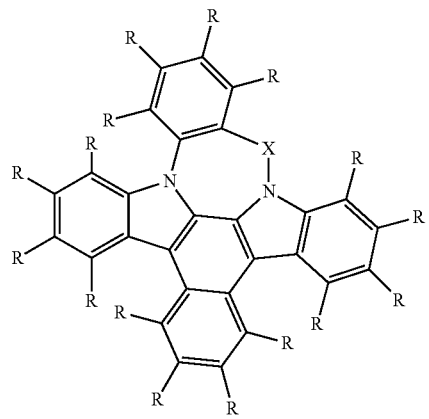
formula (28a)
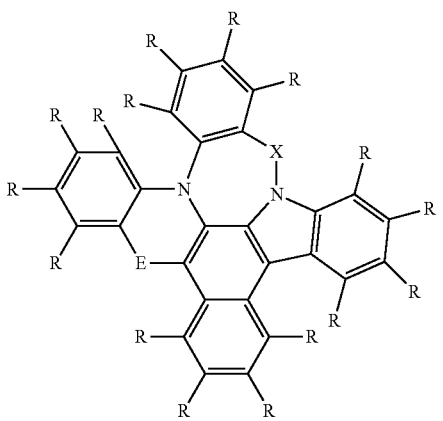
formula (26a)
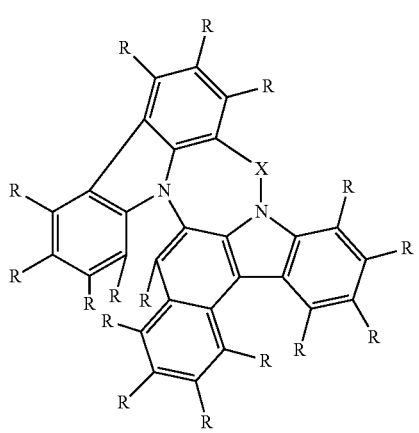
formula (29a)
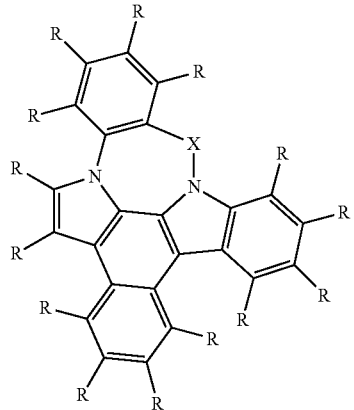
formula (27a)
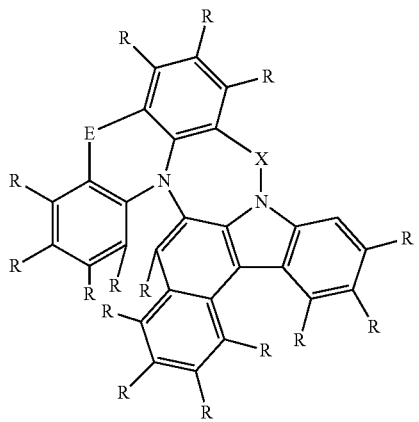
formula (30a)
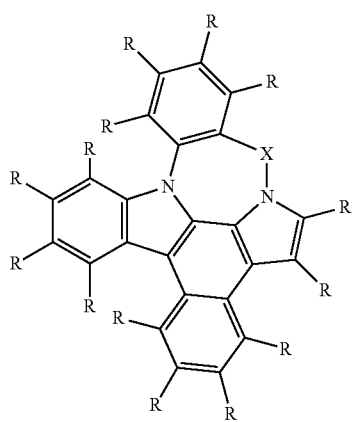

formula (31a)
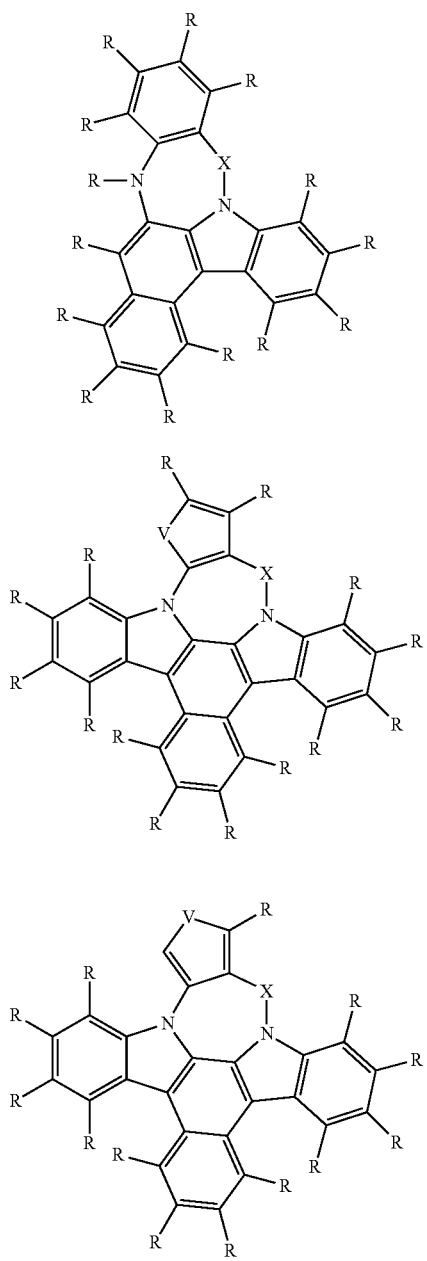
formula (32a)
formula (33a)
formula (34a)
formula (35a)
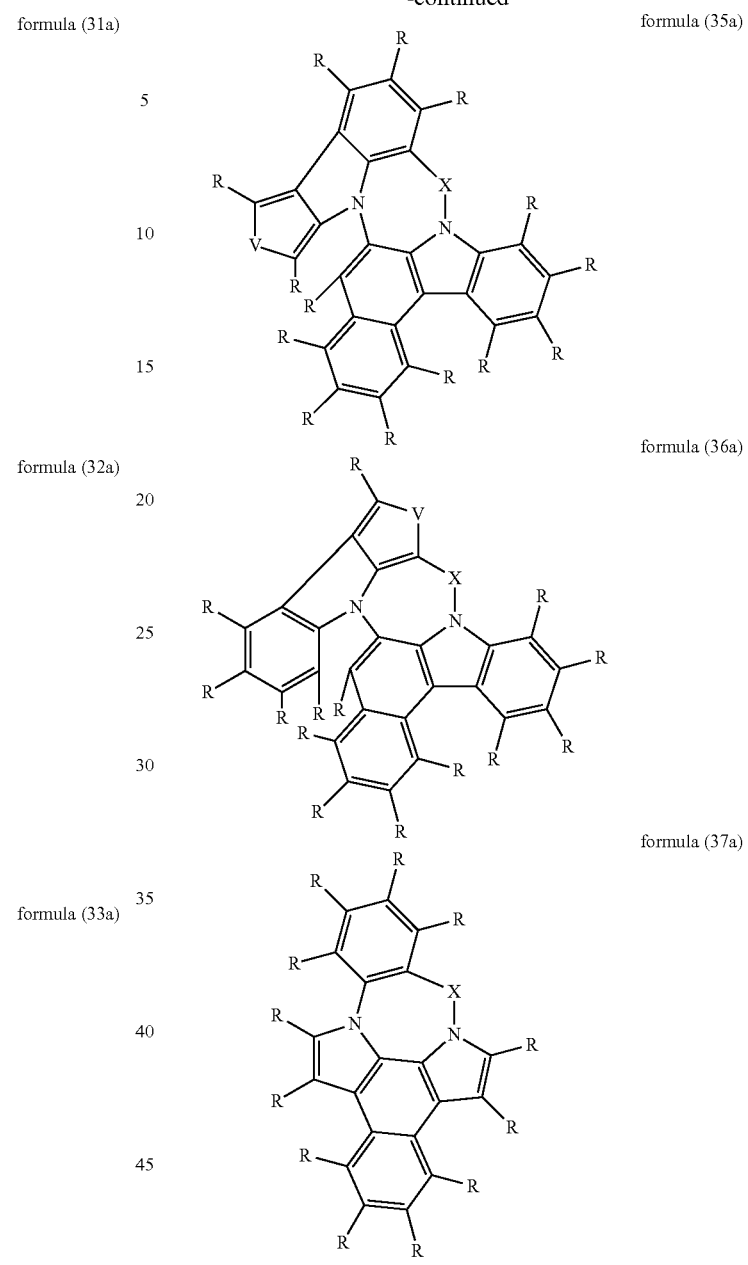
formula (36a)
formula (37a)
where the symbols used have the meanings given above.
Very particular preference is given to the compounds of the following formulae (11b) to (37b):
formula (11b)
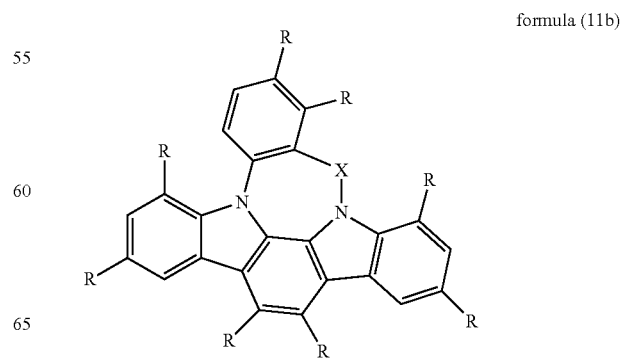

-continued
formula (12b)
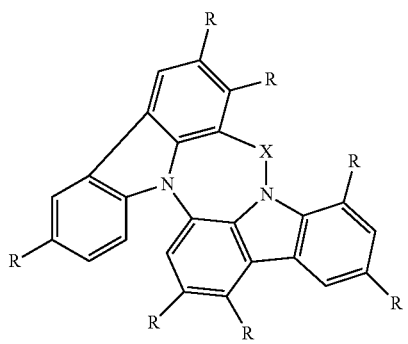
formula (13b)
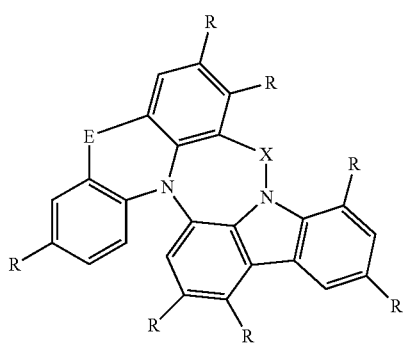
formula (14b)
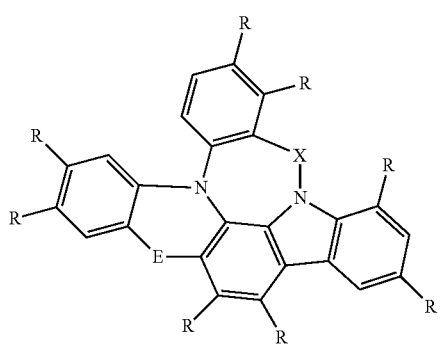
formula (15b)
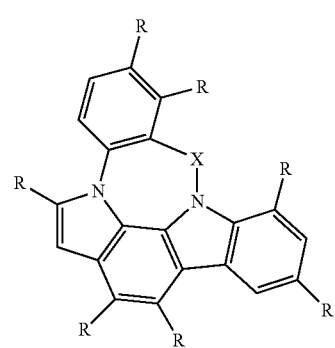
formula (16b)
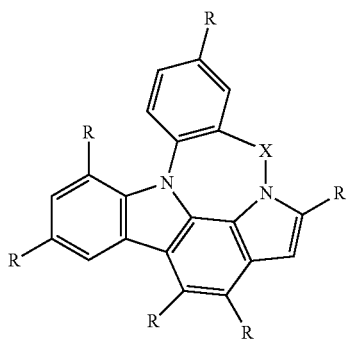
formula (17b)
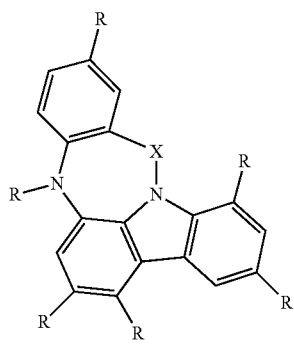
formula (18b)
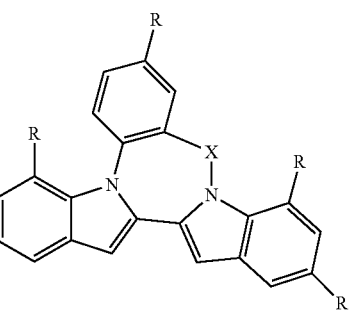
formula (19b)
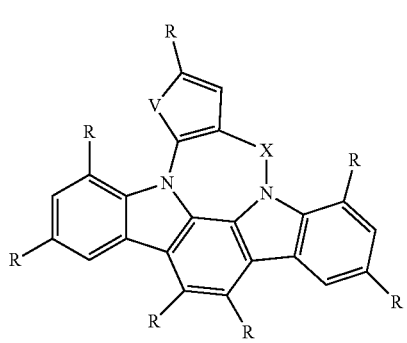
formula (20b)
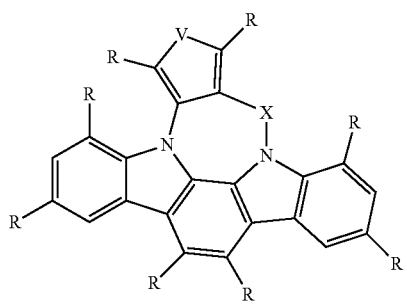

formula (21b)
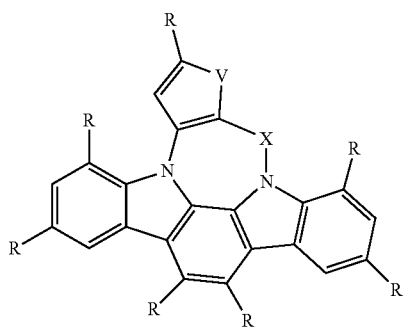
formula (22b)
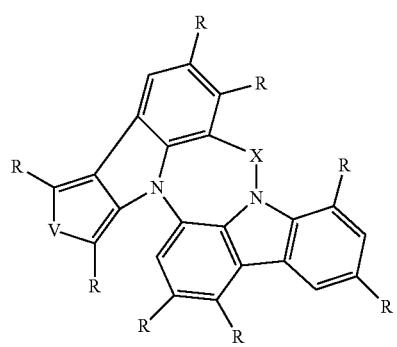
formula (23b)
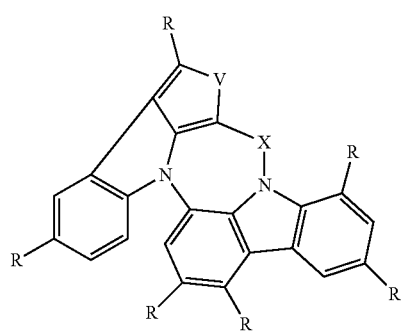
formula (24b)
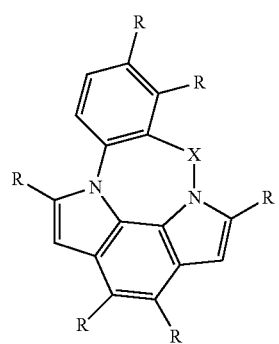
formula (25b)
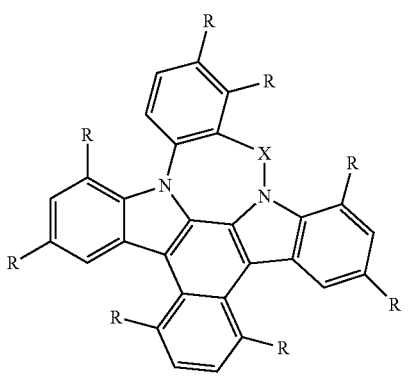
formula (26b)
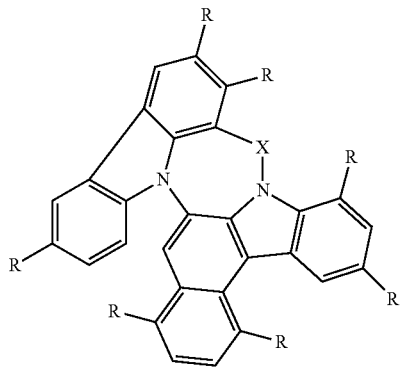
formula (28b)
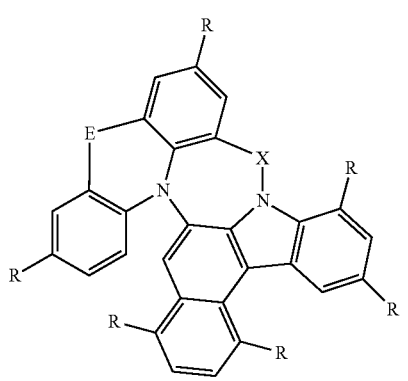
formula (27b)
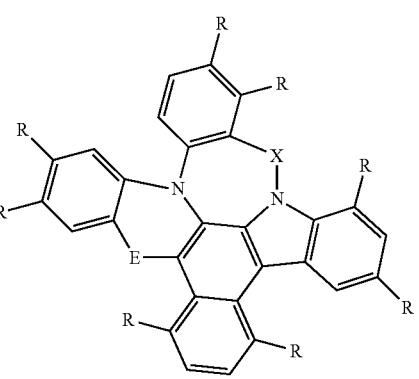

-continued
formula (29b)
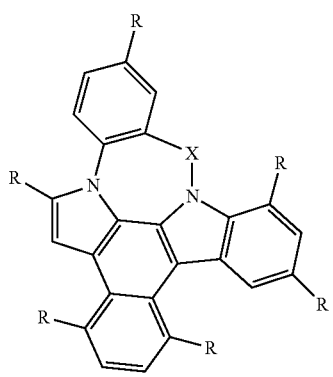
formula (30b)
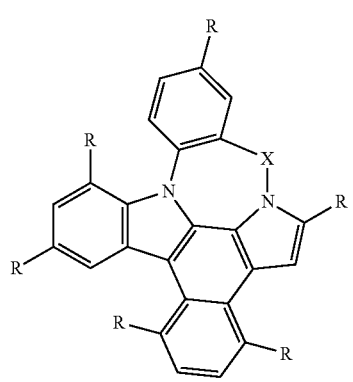
formula (31b)
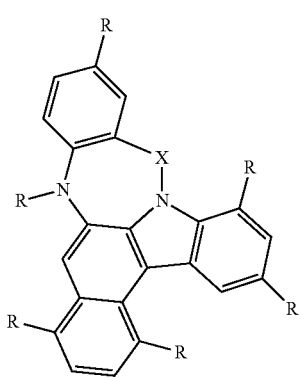
formula (32b)
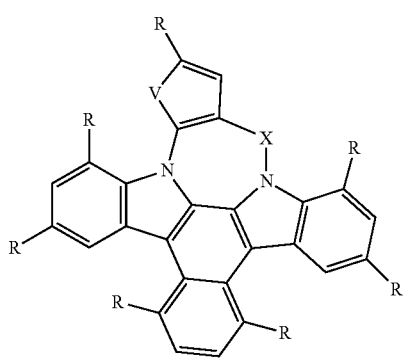
formula (33b)
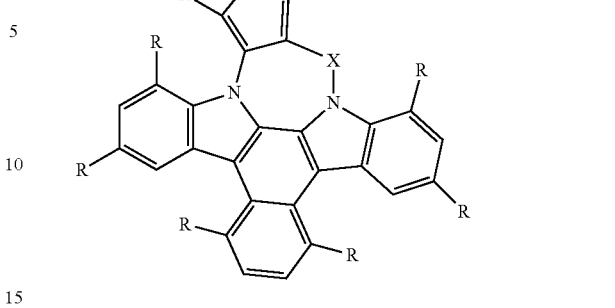
formula (34b)
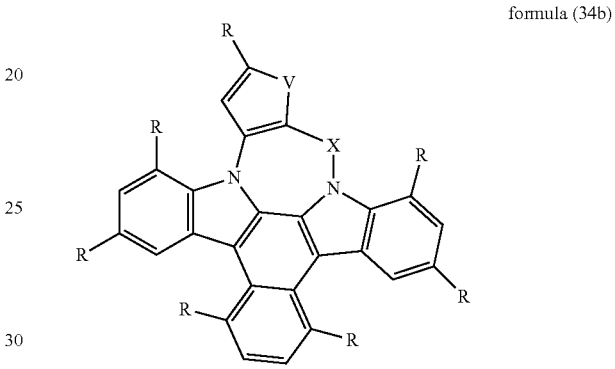
formula (35b)
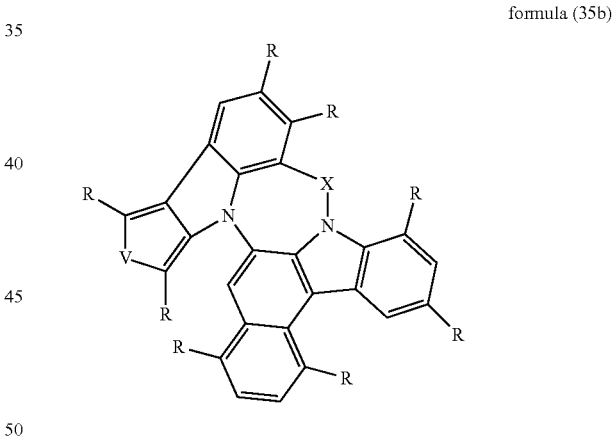
formula (36b)
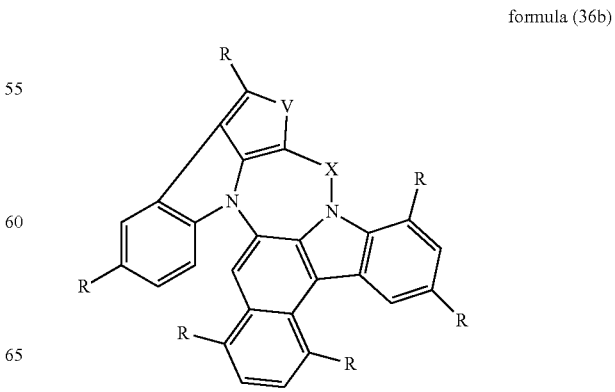

formula (37b)
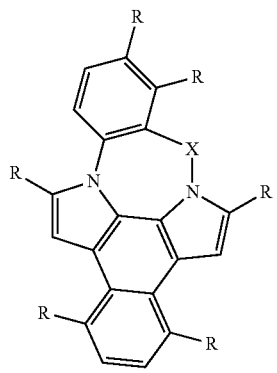
where the symbols used have the meanings given above.
Especial preference is given to the compounds of the following formulae (11c) to (37c):
formula (11c)
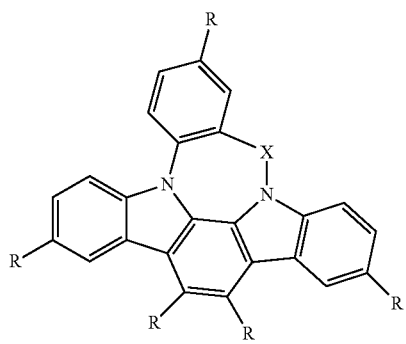
formula (12c)
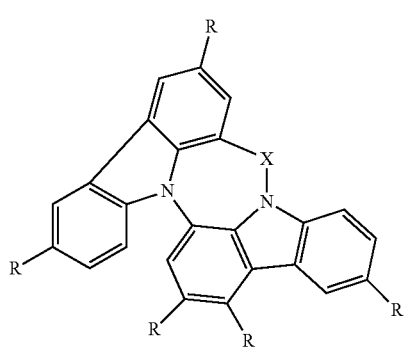
formula (13c)
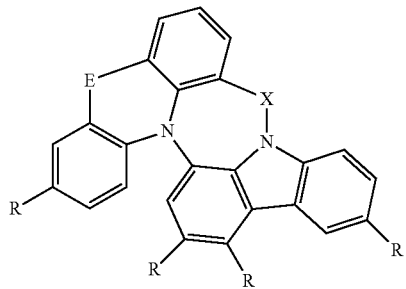
formula (14c)
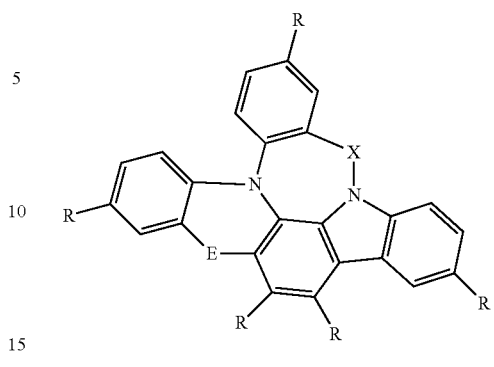
formula (15c)
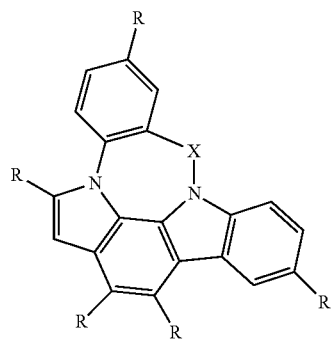
formula (16c)
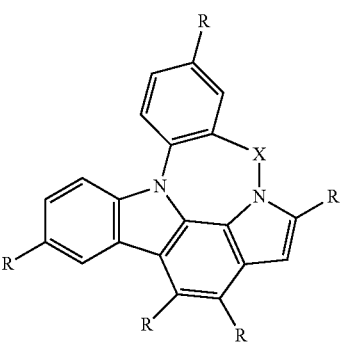
formula (17c)
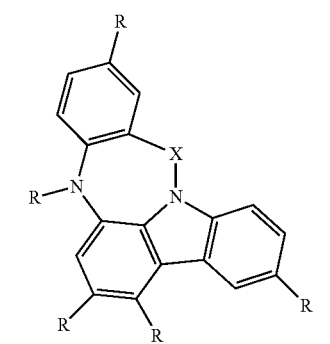

formula (18c)
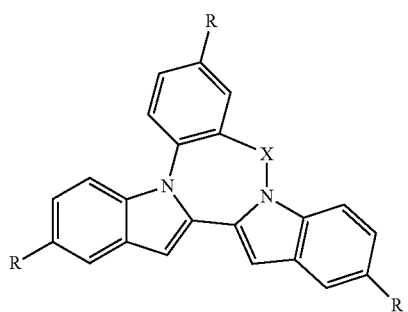
formula (19c)
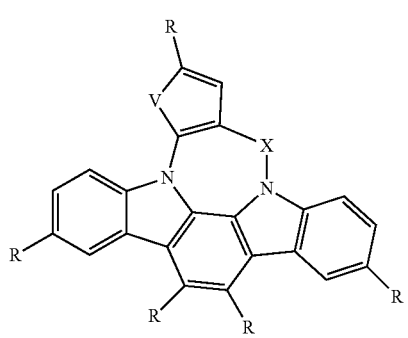
formula (20c)
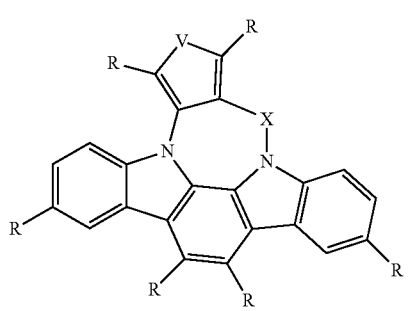
formula (21c)
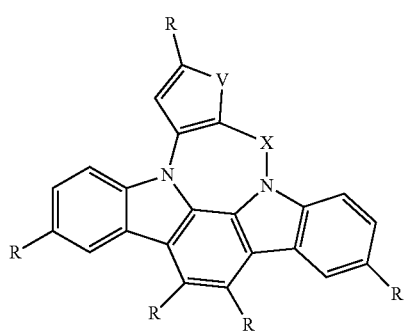
formula (22c)
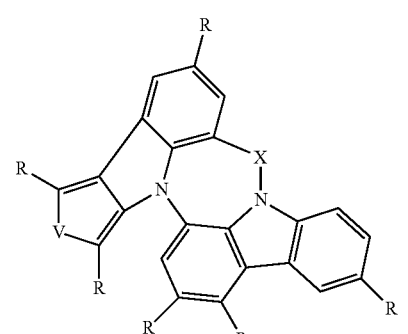
formula (23c)
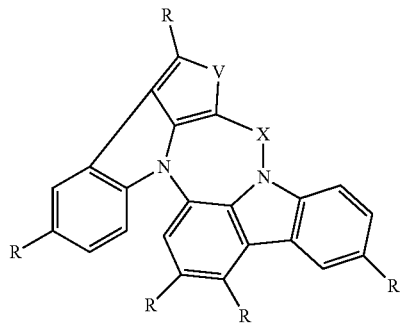
formula (24c)
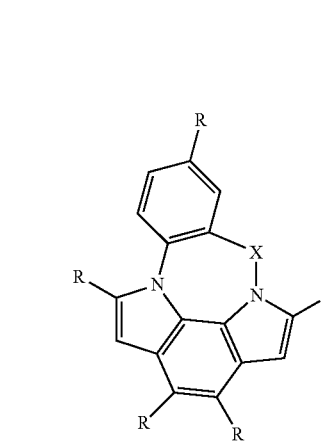
formula (25c)
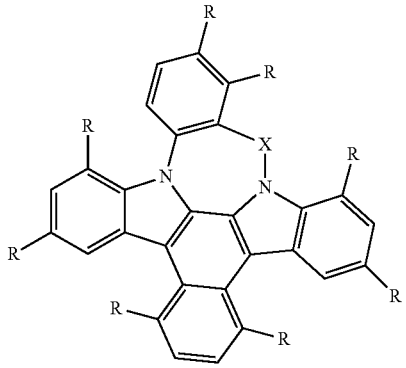
formula (26c)

-continued
formula (28c)
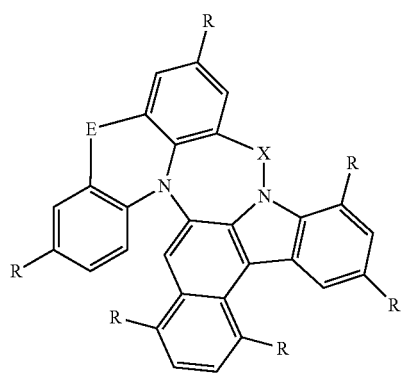
formula (27c)
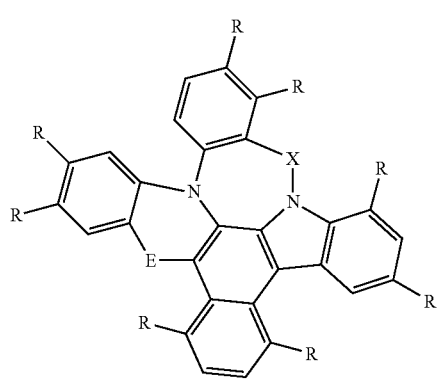
formula (29c)
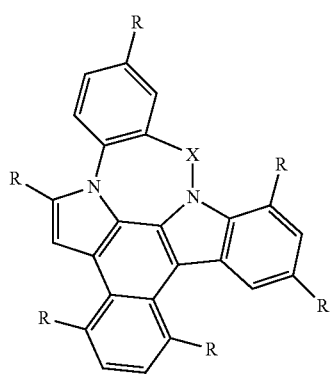
formula (30c)
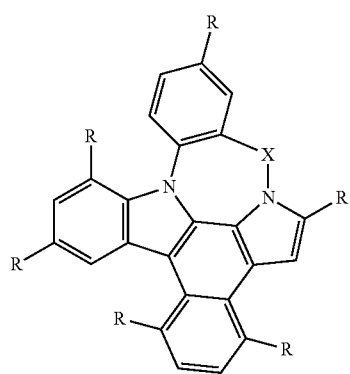
formula (31c)
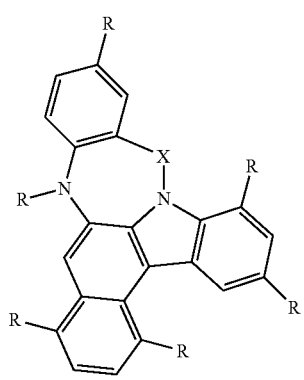
formula (32c)
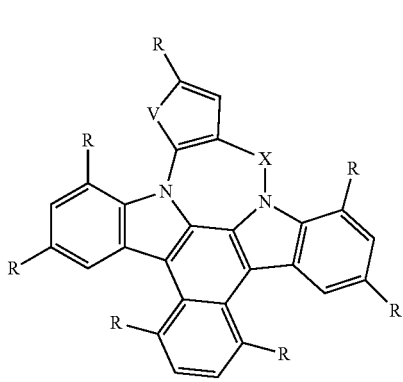
formula (33c)
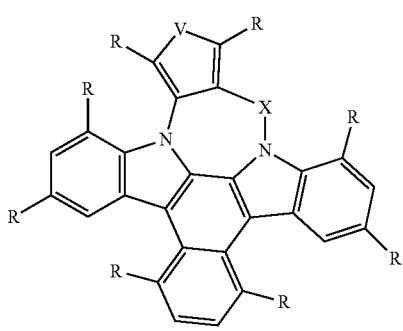
formula (34c)
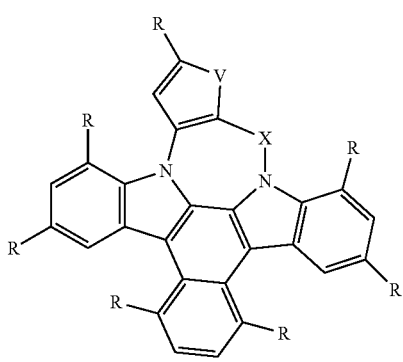

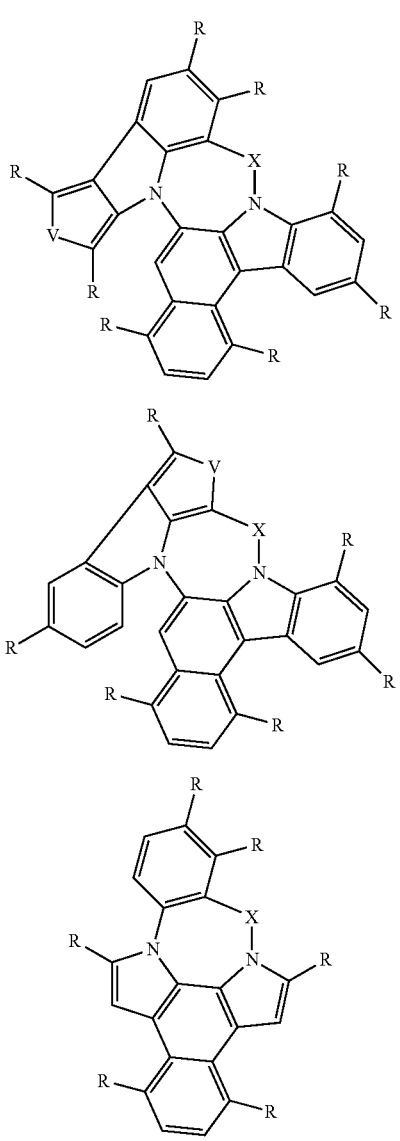

formula (35c)

formula (36c)

formula (37c)

where the symbols used have the meanings given above.

In the formulae (11a) to (37c), X preferably stands for C=O or SO$_2$.

Furthermore, in the formulae (11a) to (37c), E preferably stands for CR$_2$, C=O or NR.

In the formulae (11a) to (37c), it is particularly preferred for X to stand for C=O or SO$_2$ and at the same time for E to stand for CR$_2$, C=O or NR.

In a preferred embodiment of the invention, R in the formulae given above is selected, identically or differently on each occurrence, from the group consisting of H, D, F, Cl, Br, CN, N(Ar$^1$)$_2$, C(=O)Ar$^1$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which may be substituted by one or more radicals R$^1$, where one or more non-adjacent CH$_2$ groups may be replaced by O and where one or more H atoms may be replaced by D or F, an aromatic or heteroaromatic ring system having 5 to 30 aromatic ring atoms, which may in each case be substituted by one or more radicals R$^1$, an aryloxy or heteroaryloxy group having 5 to 30 aromatic ring atoms, which may be substituted by one or more radicals R$^1$, or a combination of these systems.

In a particularly preferred embodiment of the invention, R in the formulae given above is selected, identically or differently on each occurrence, from the group consisting of H, D, F, Cl, Br, CN, a straight-chain alkyl group having 1 to 10 C atoms or a branched or cyclic alkyl group having 3 to 10 C atoms, each of which may be substituted by one or more radicals R$^1$, where one or more H atoms may be replaced by D or F, an aromatic or heteroaromatic ring system having 5 to 18 aromatic ring atoms, which may in each case be substituted by one or more radicals R$^1$, or a combination of these systems.

For compounds which are processed by vacuum evaporation, the alkyl groups preferably have not more than four C atoms, particularly preferably not more than 1 C atom. For compounds which are processed from solution, compounds which are substituted by alkyl groups having up to 10 C atoms or which are substituted by oligoarylene groups, for example ortho-, meta-, para- or branched terphenyl groups, are also suitable.

Examples of preferred compounds in accordance with the embodiments indicated above or compounds as can preferably be employed in electronic devices are the compounds of the following structures.

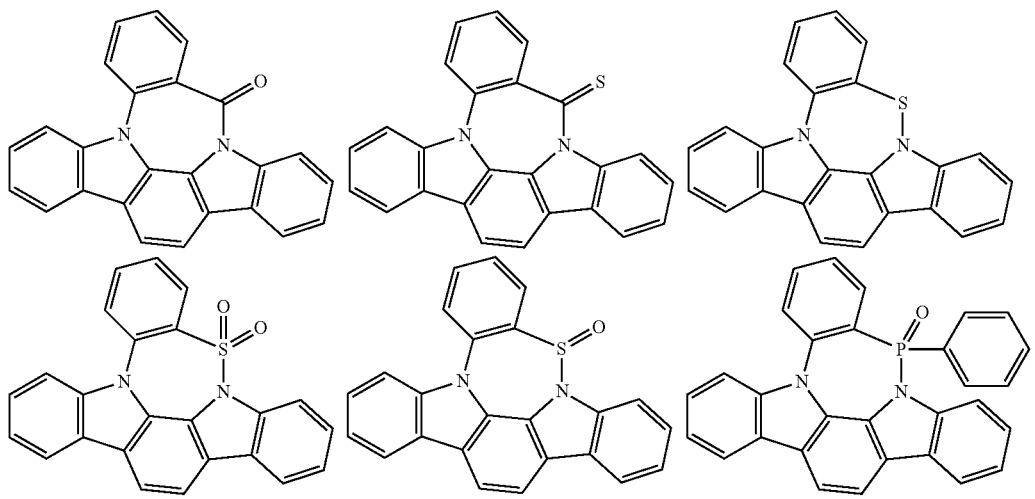

-continued
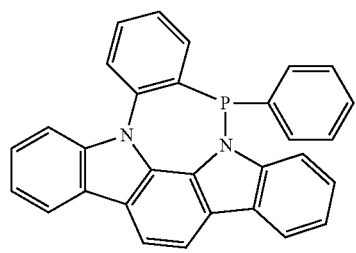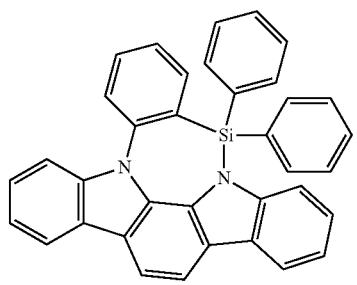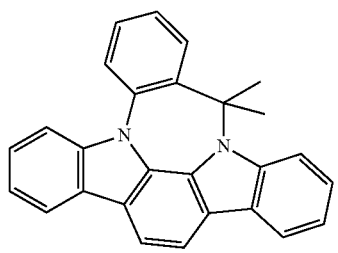
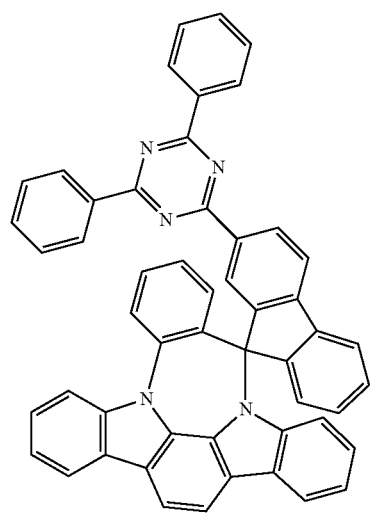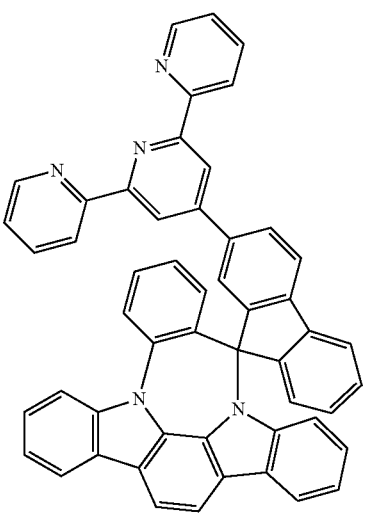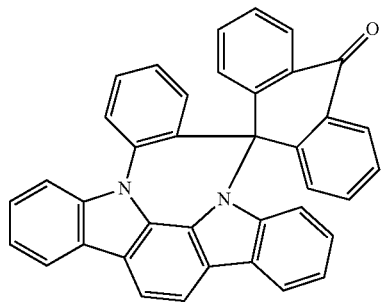
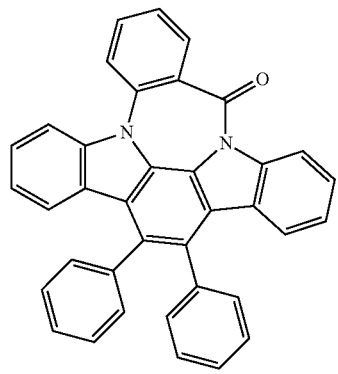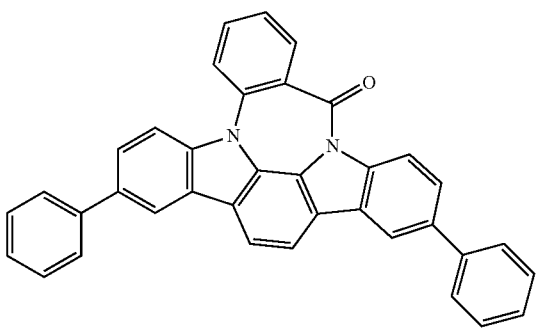
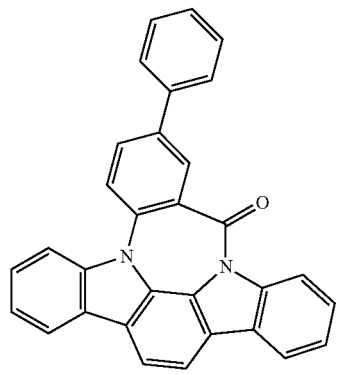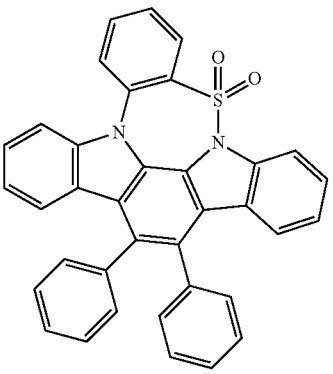

-continued
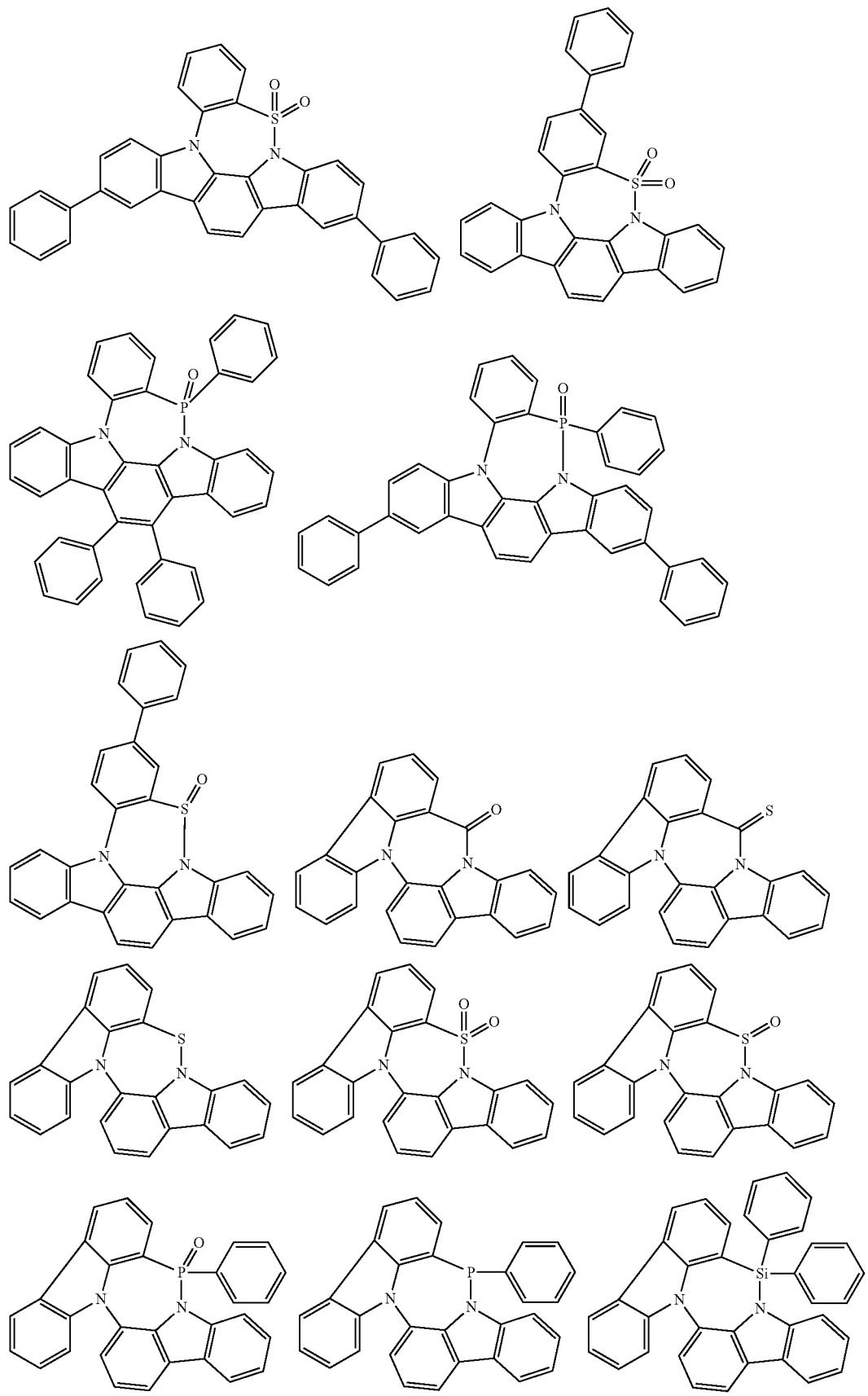

-continued
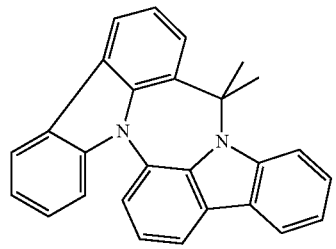
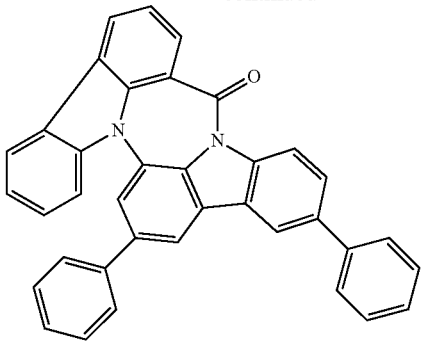
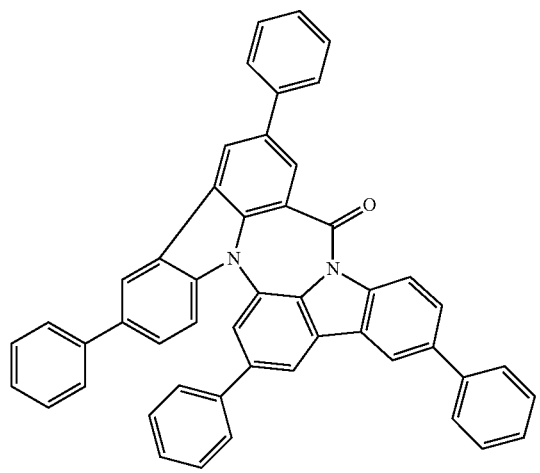
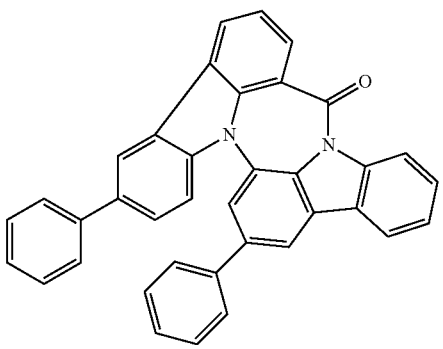
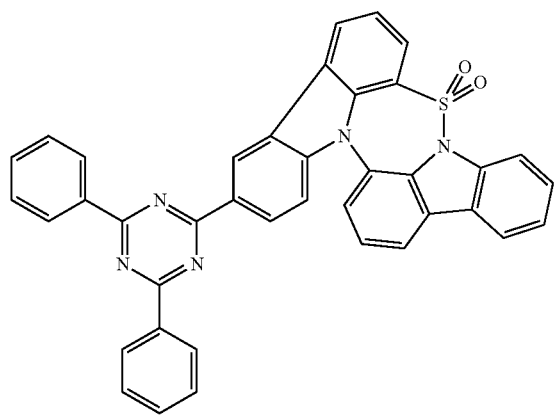
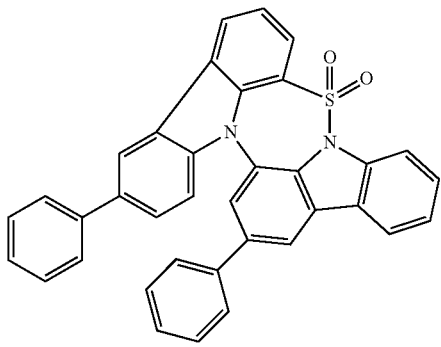
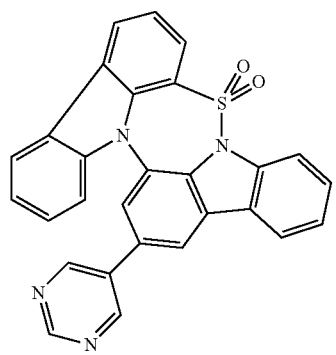
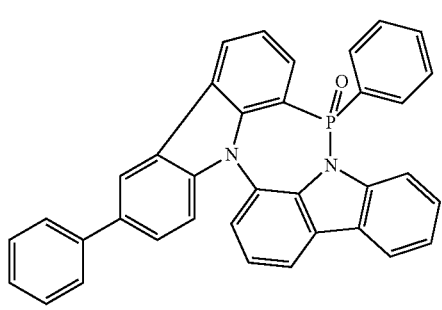

-continued
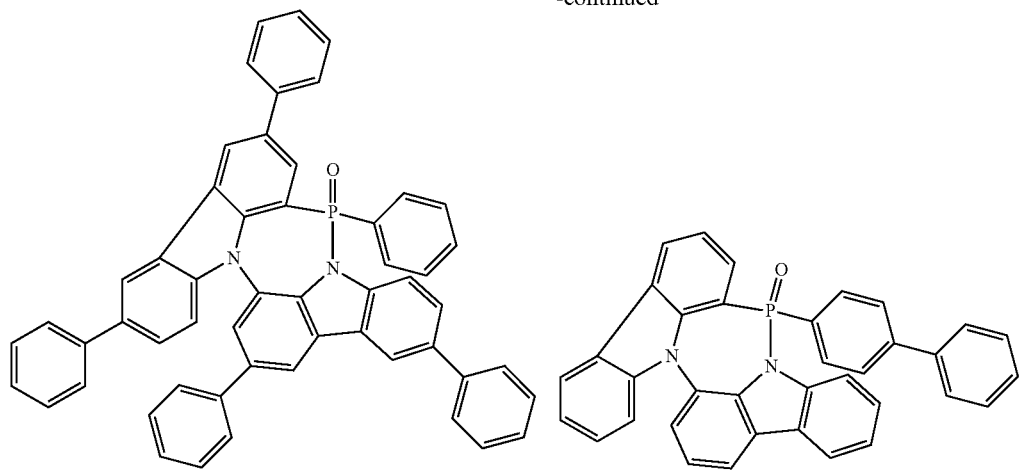
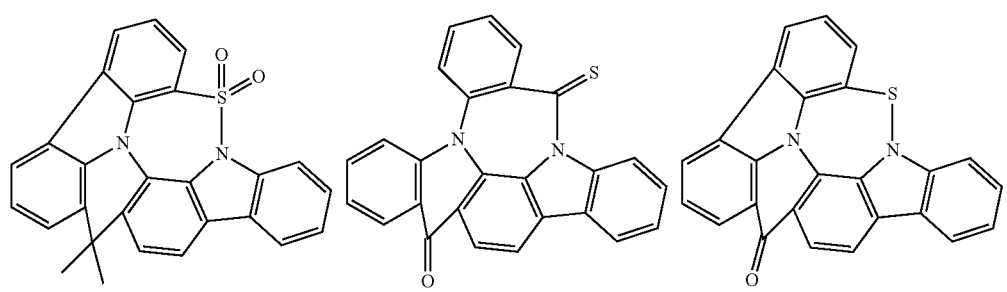
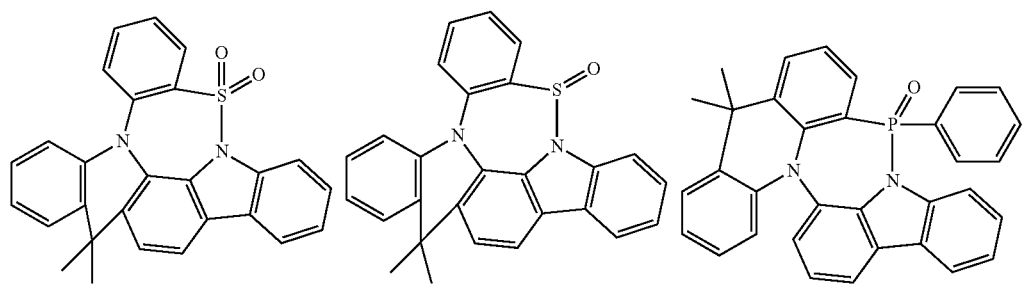
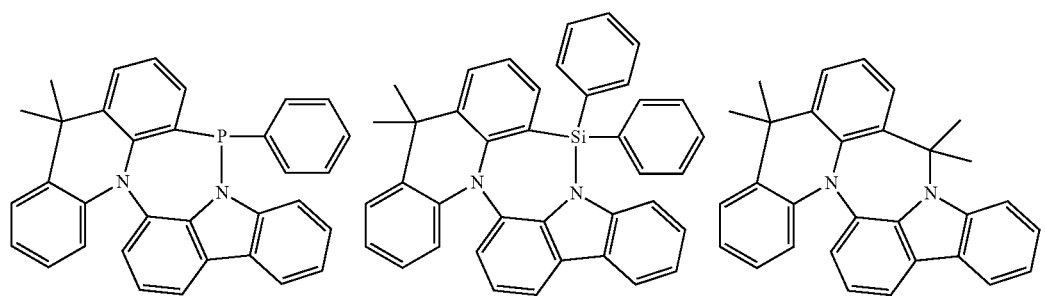
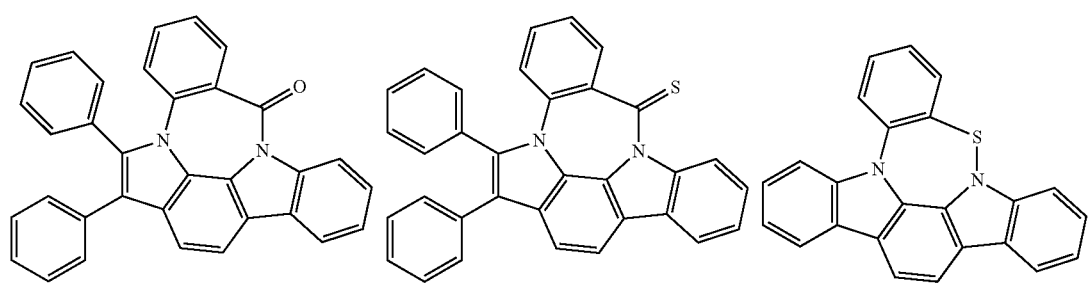

-continued
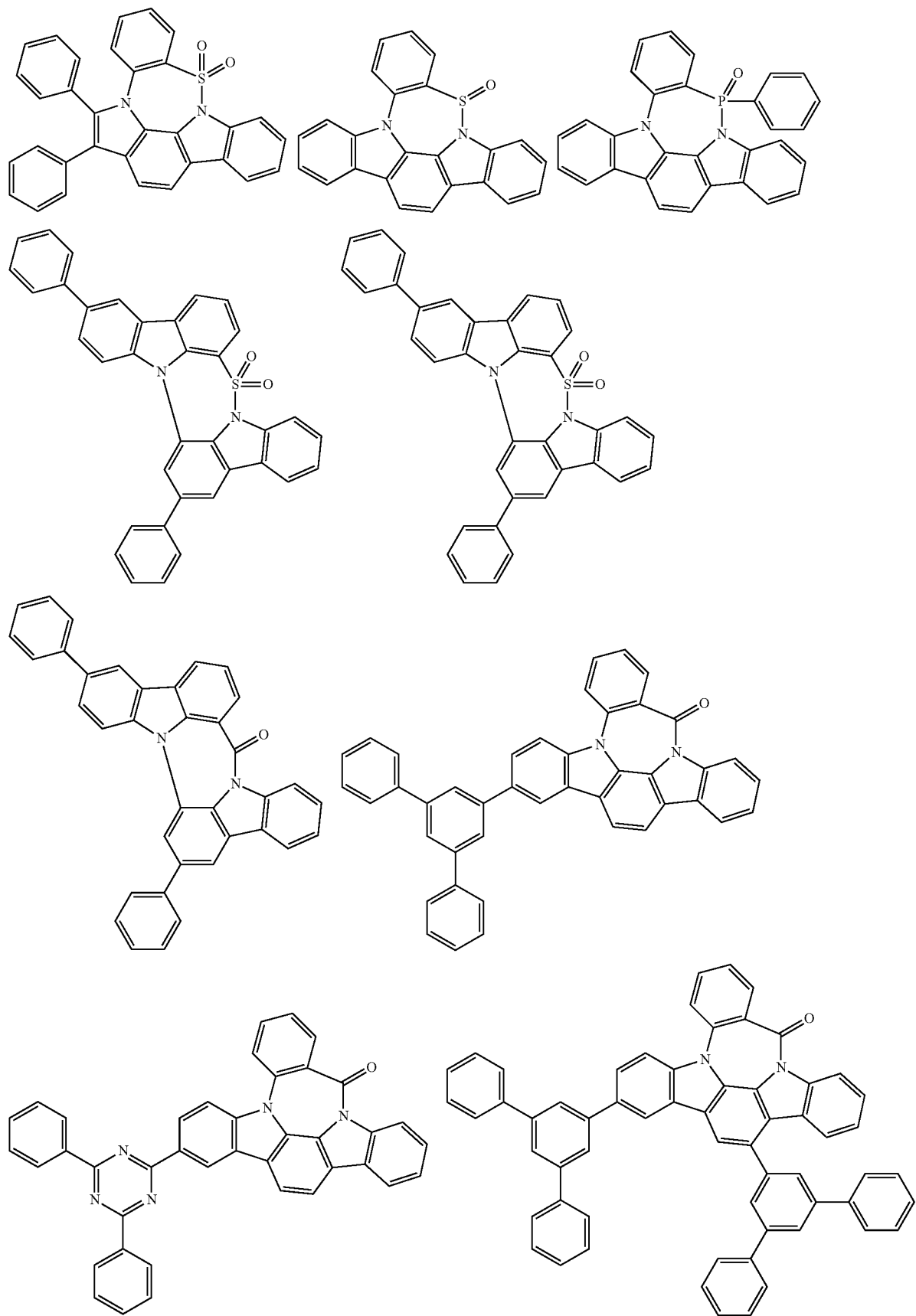

-continued
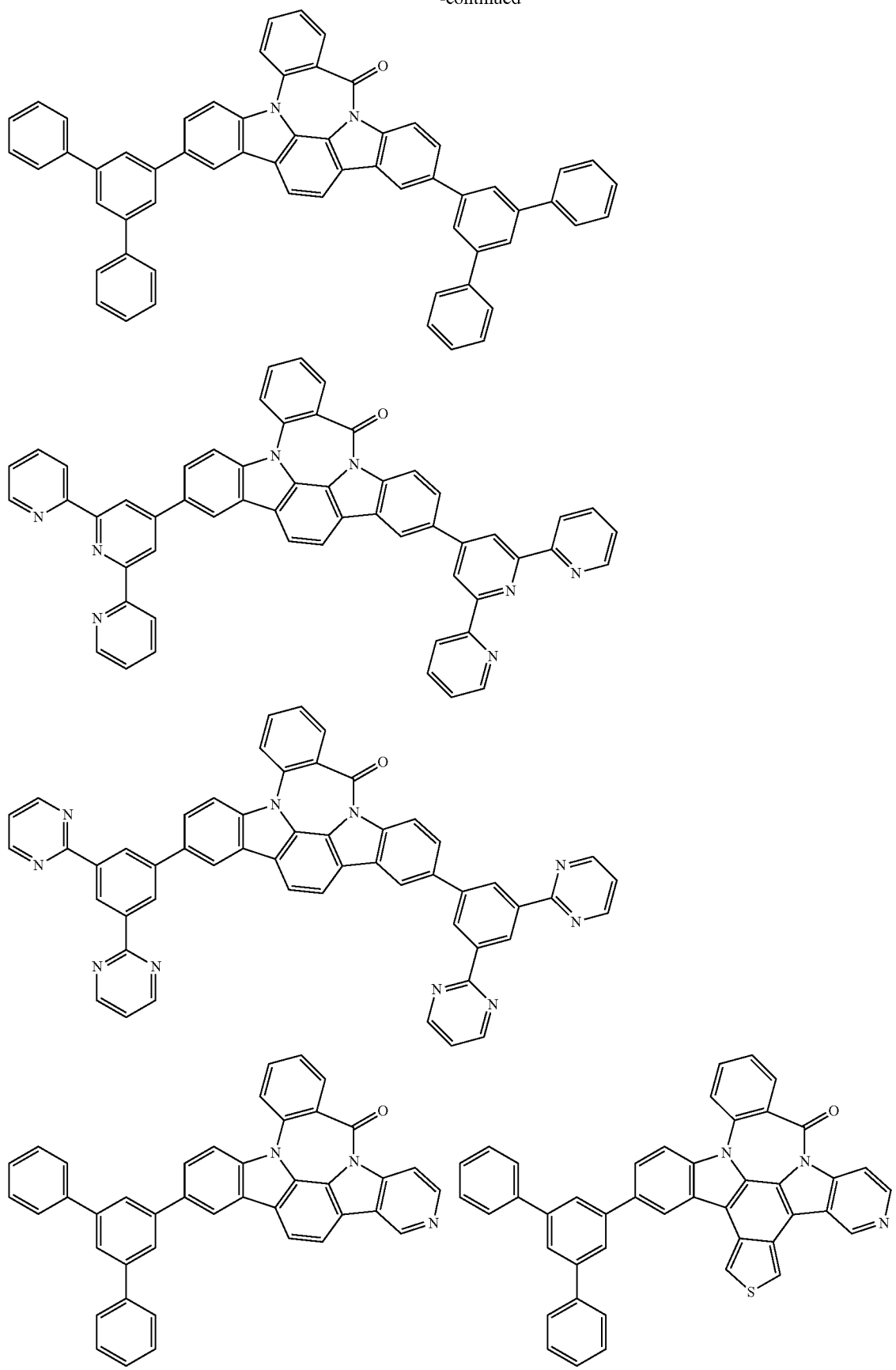

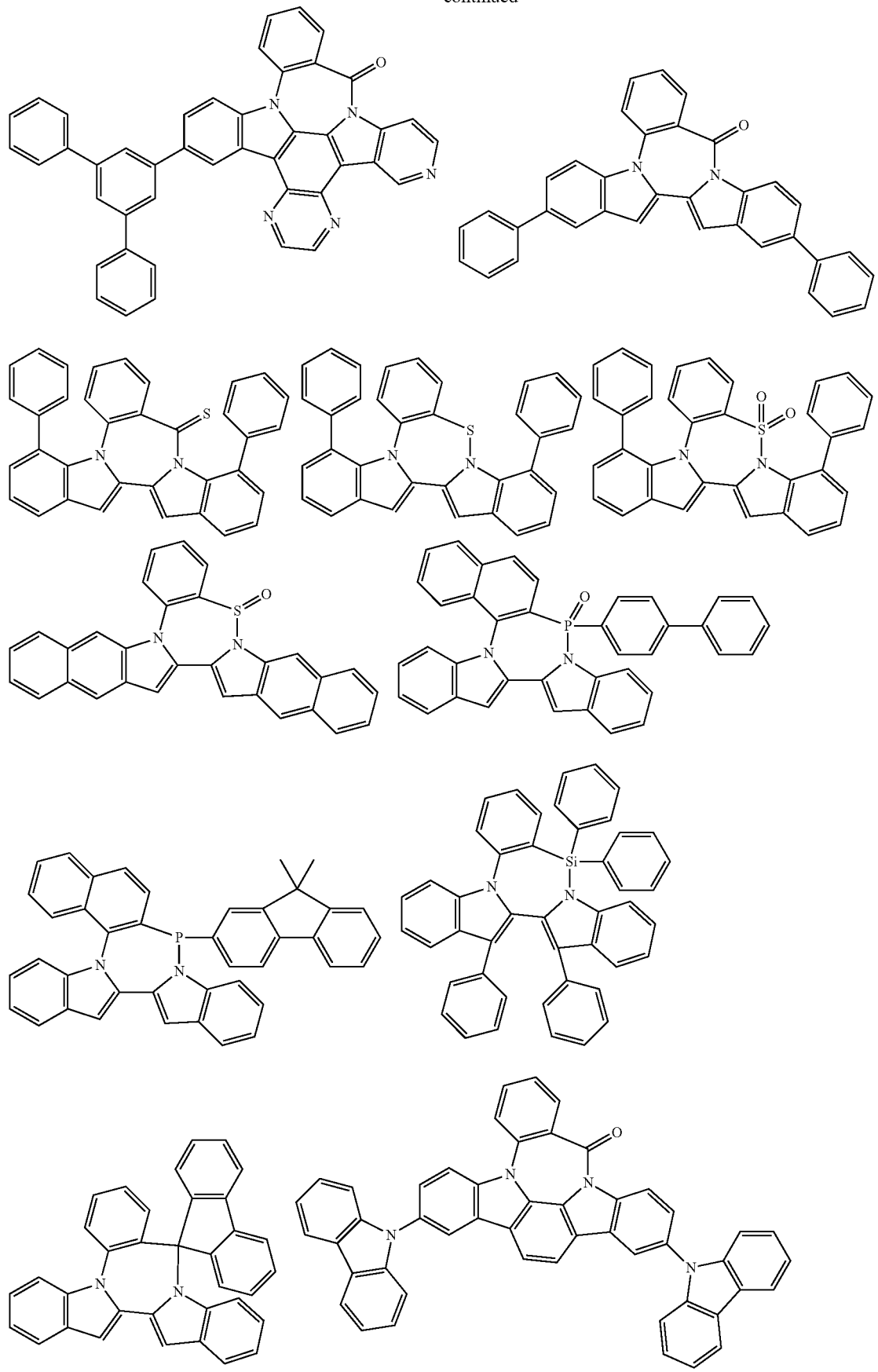

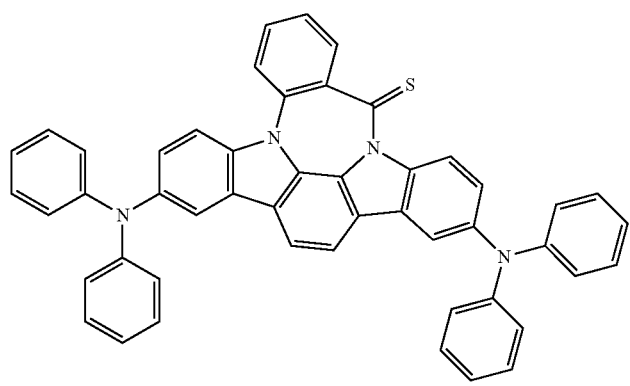
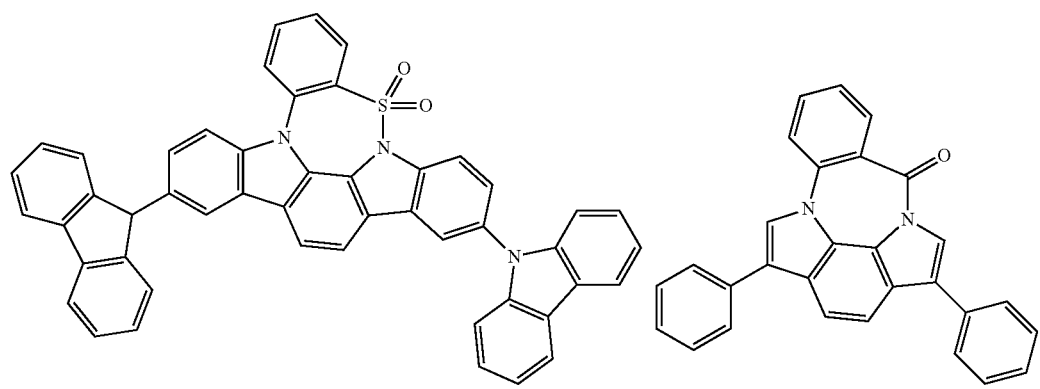
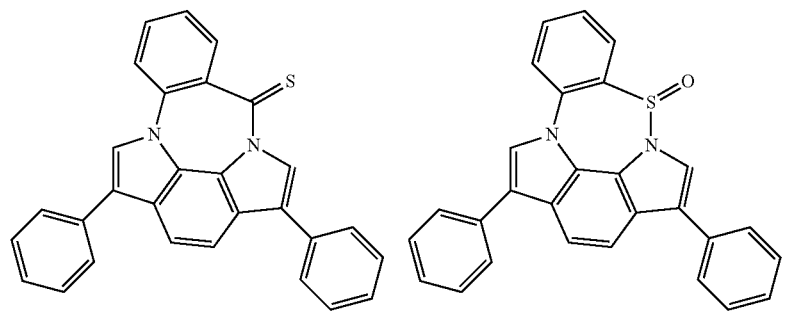
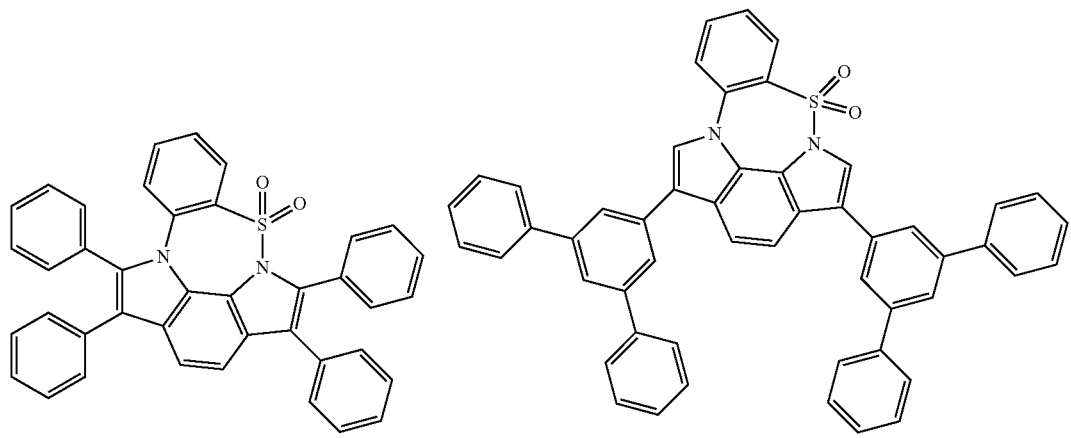

51
-continued
52
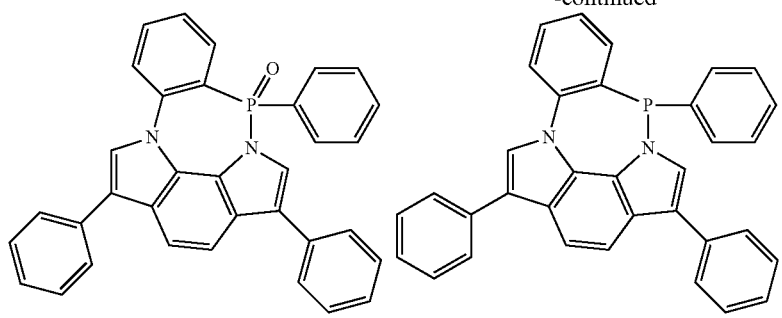
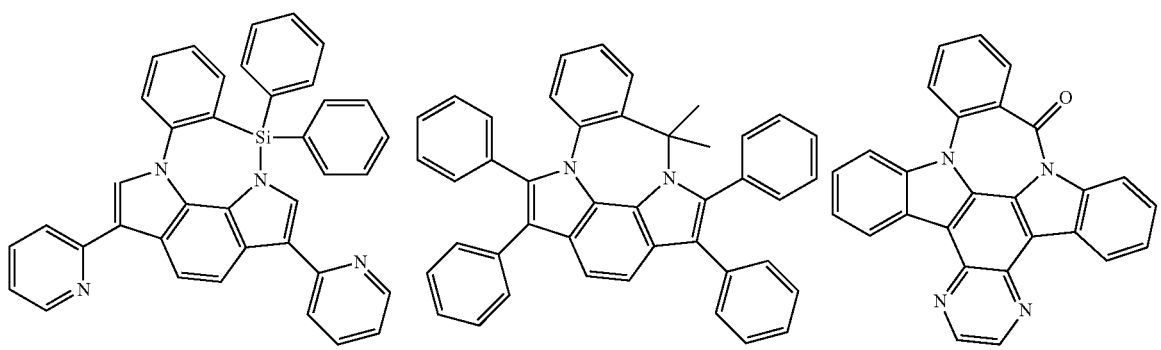
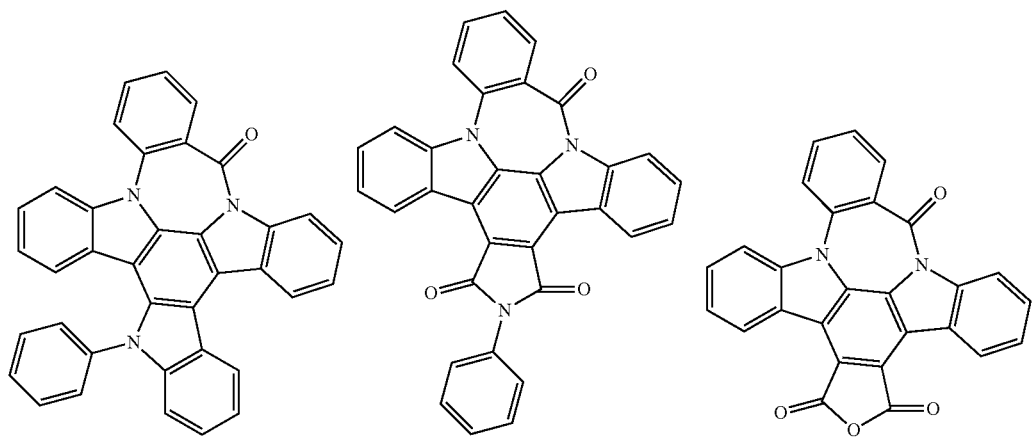
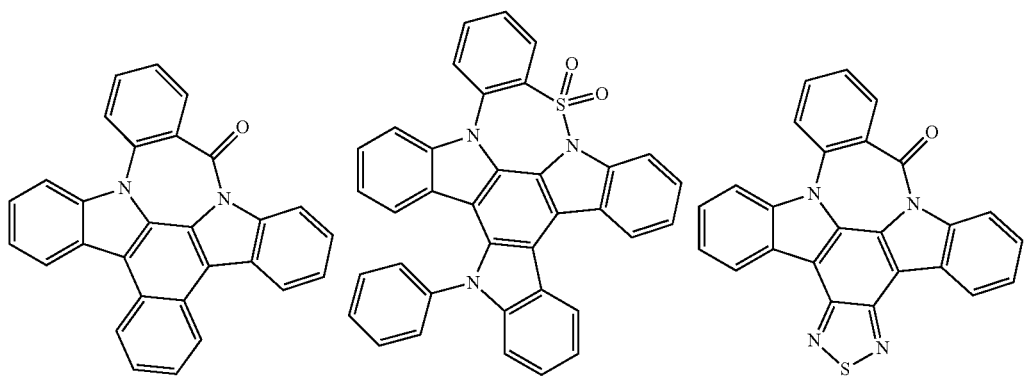

-continued
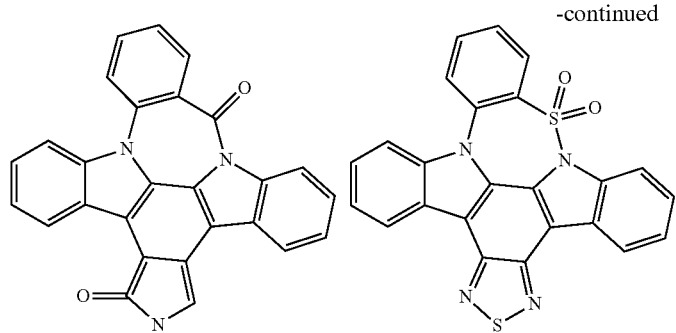
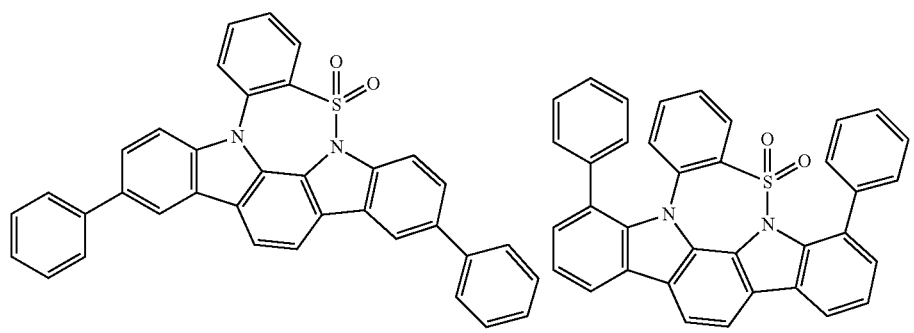
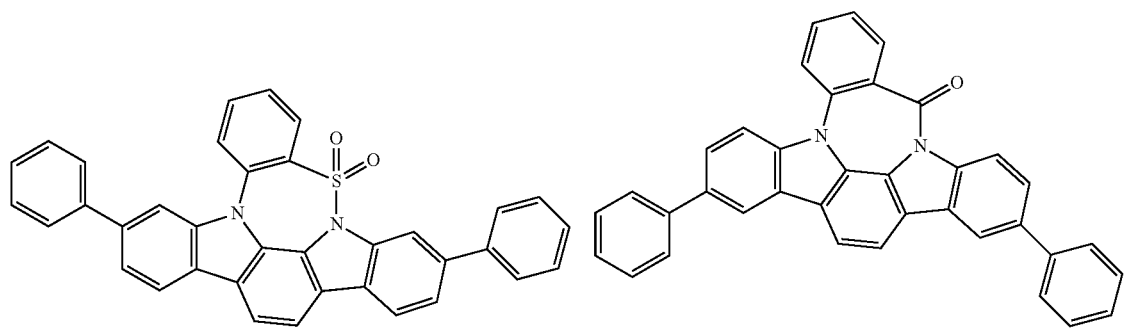
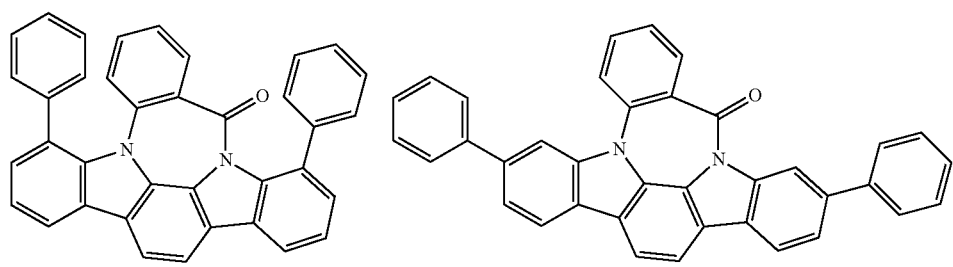
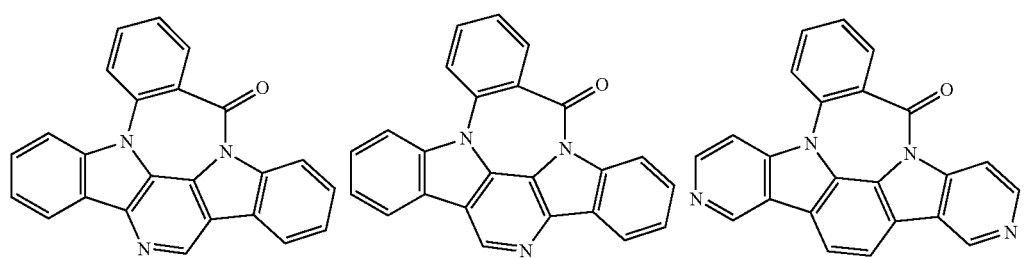

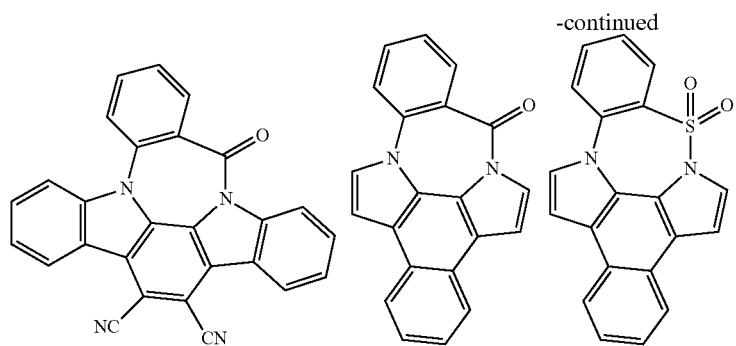

The compounds according to the invention can be prepared by synthetic steps known to the person skilled in the art, as depicted schematically in Schemes 1 to 8. The synthesis here is carried out starting from cis-indolocarbazole or related derivatives, the synthesis of which is known to the person skilled in the art (for example Chemistry Letters 2005, 34(11), 1500-1501; Tetrahedron Letters 2009, 50(13), 1469-1471; Khimiya Geterotsiklichenskikh Soedinenii 1985, (9), 1222-1224).

A possible synthesis here is the reaction of the cis-indolocarbazole or the related derivative with an ortho-halobenzoic acid ester, where the halogen is preferably iodine, in the presence of copper and a copper(I) salt, as depicted in Scheme 1.

Scheme 1:

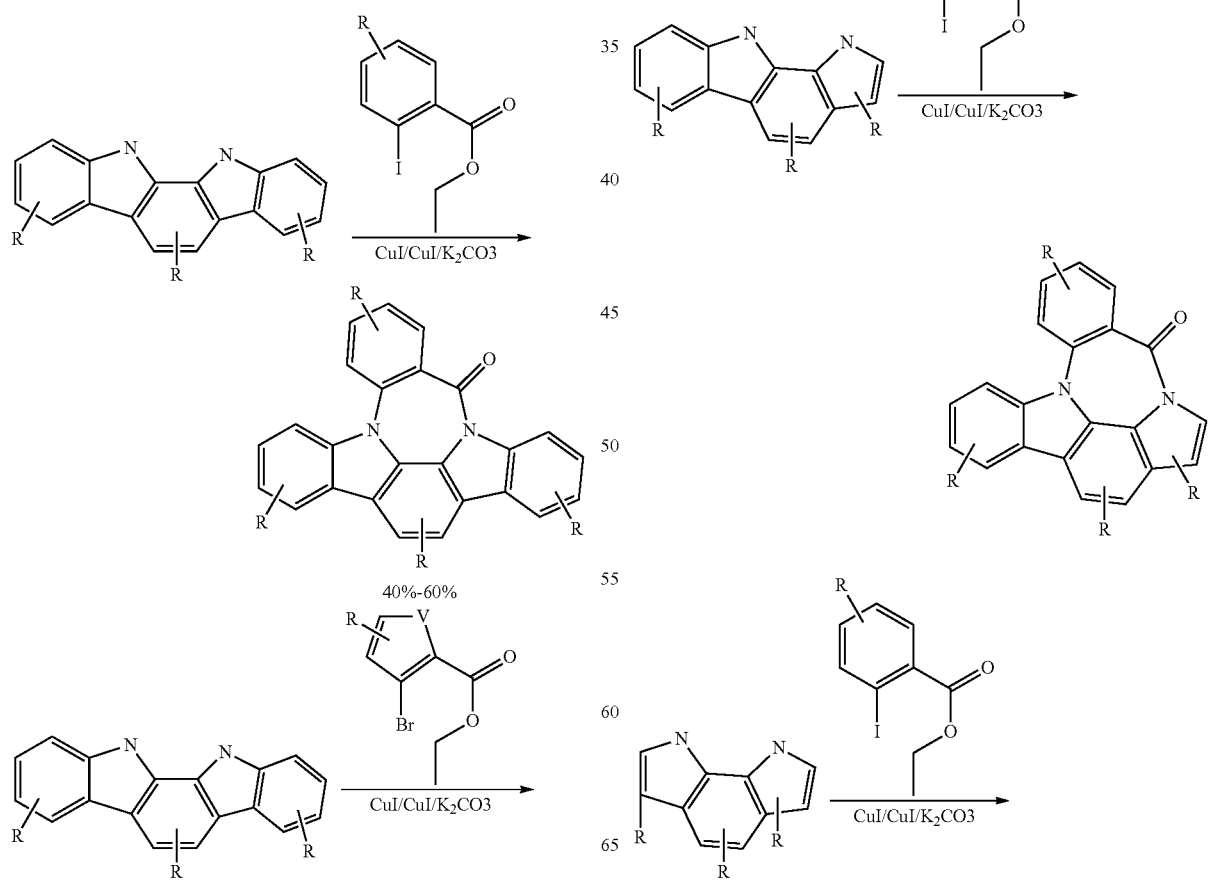

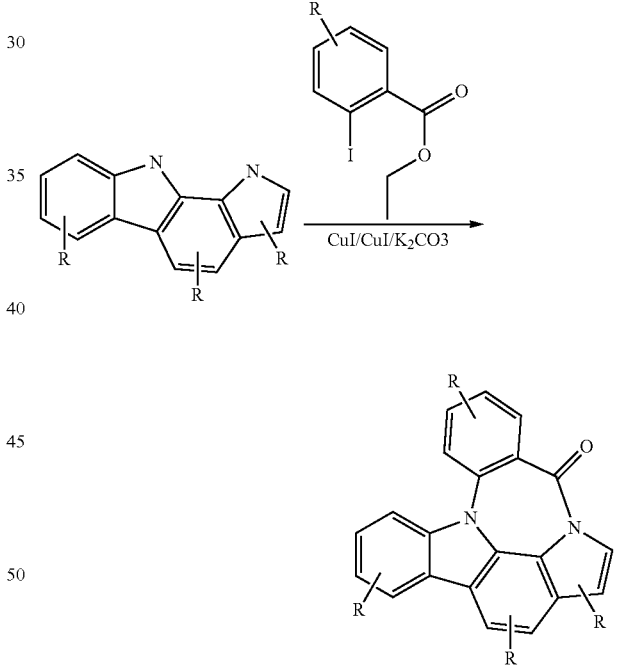

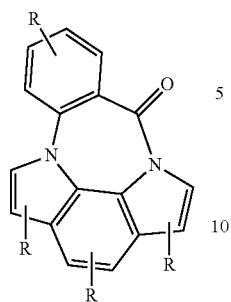

A further possible synthesis here is the reaction of the cis-indolocarbazole or the related derivative with an ortho-halobenzoyl chloride, where the halogen is preferably iodine. In a first step here, the acid chloride reacts with one of the two nitrogen atoms, and, in a further step, the halogen reacts with the second nitrogen atom in the presence of copper and a copper(I) salt, as depicted in Scheme 2.

Scheme 2:

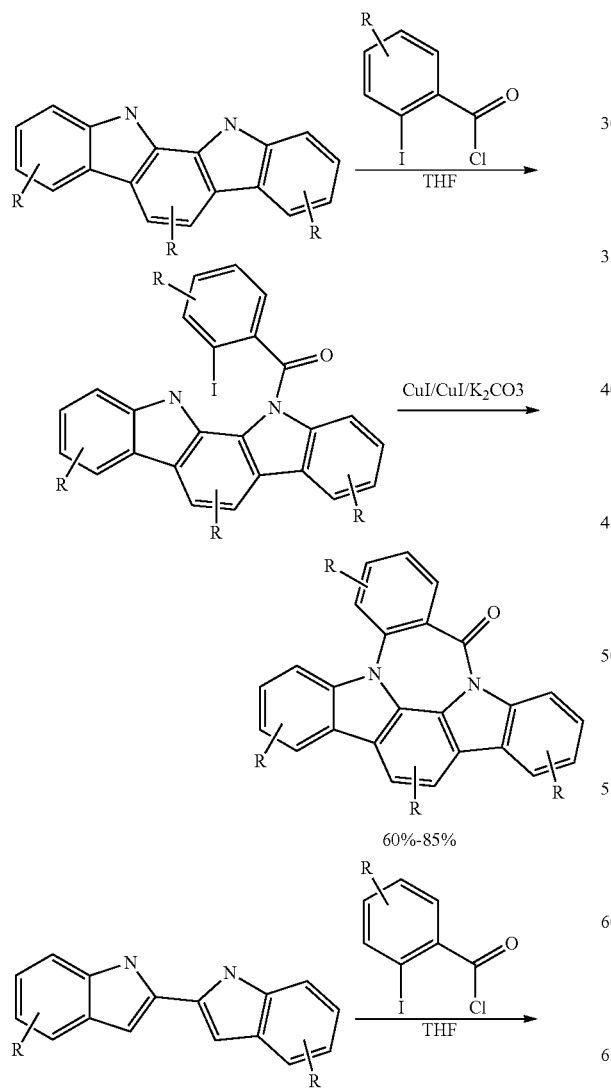

60%-85%

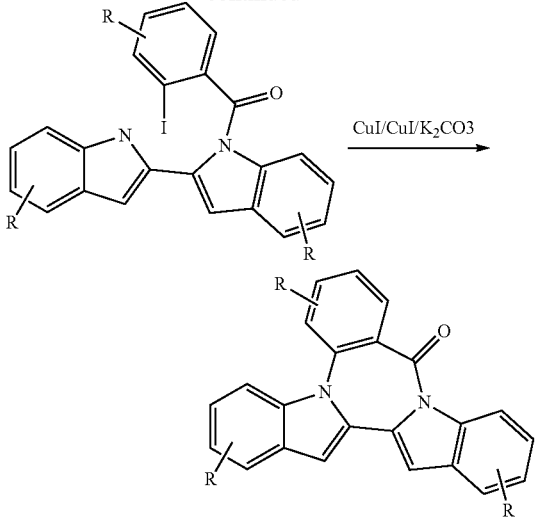

An $SO_2$ bridge can be introduced by reacting the cis-indolocarbazole or the related derivative with an ortho-halosulfonic acid chloride, where the halogen is preferably iodine. In a first step here, the sulfonic acid chloride reacts with one of the two nitrogen atoms, and, in a further step, the halogen reacts with the second nitrogen atom in the presence of copper and a copper(I) salt, as depicted in Scheme 3.

Scheme3:

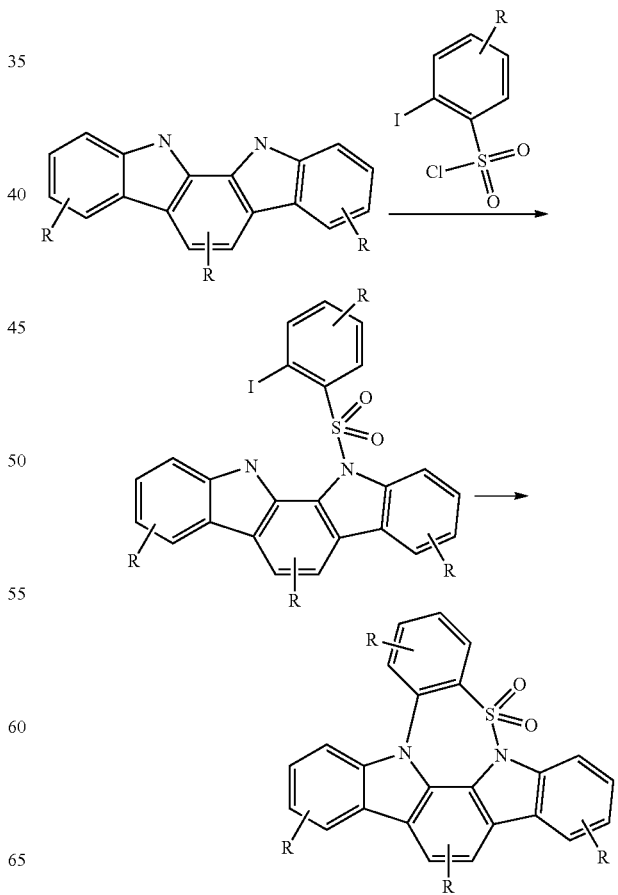

A CR$_2$ bridge can be introduced by reacting the cis-indolocarbazole or the related derivative with an ortho-halobenzyl chloride, where the halogen is preferably iodine. In a first step here, the benzyl chloride reacts with one of the two nitrogen atoms, and, in a further step, the halogen reacts with the second nitrogen atom in the presence of copper and a copper (I) salt, as depicted in Scheme 4.

Scheme 4:

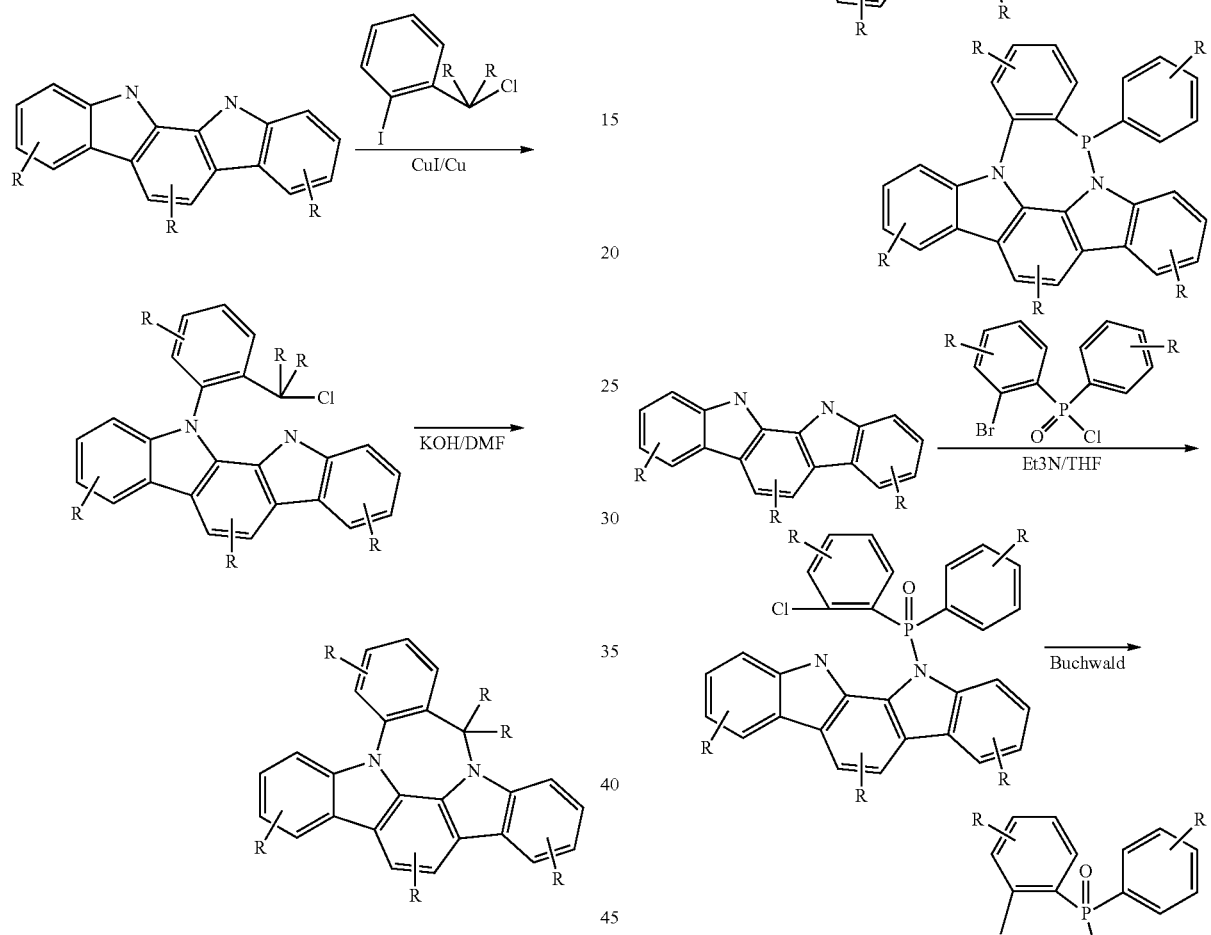

A phosphorus bridge can be introduced by reacting the cis-indolocarbazole or the related derivative with an ortho-halophosphinyl chloride, where the halogen is preferably iodine. In a first step here, the phosphinyl chloride reacts with one of the two nitrogen atoms, and, in a further step, the halogen reacts with the second nitrogen atom in the presence of copper and a copper(I) salt, as depicted in Scheme 5. A phosphine oxide bridge can be introduced analogously by reaction with a phosphinyl oxychloride.

Scheme 5:

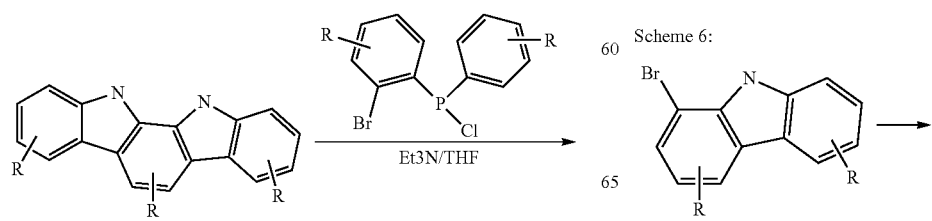

The synthesis of further derivatives according to the invention which are not derived directly from the indolocarbazole, but instead which contain other groups E, is depicted schematically in Scheme 6 to Scheme 8.

Scheme 6:

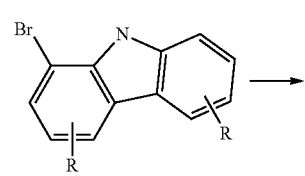

61
-continued
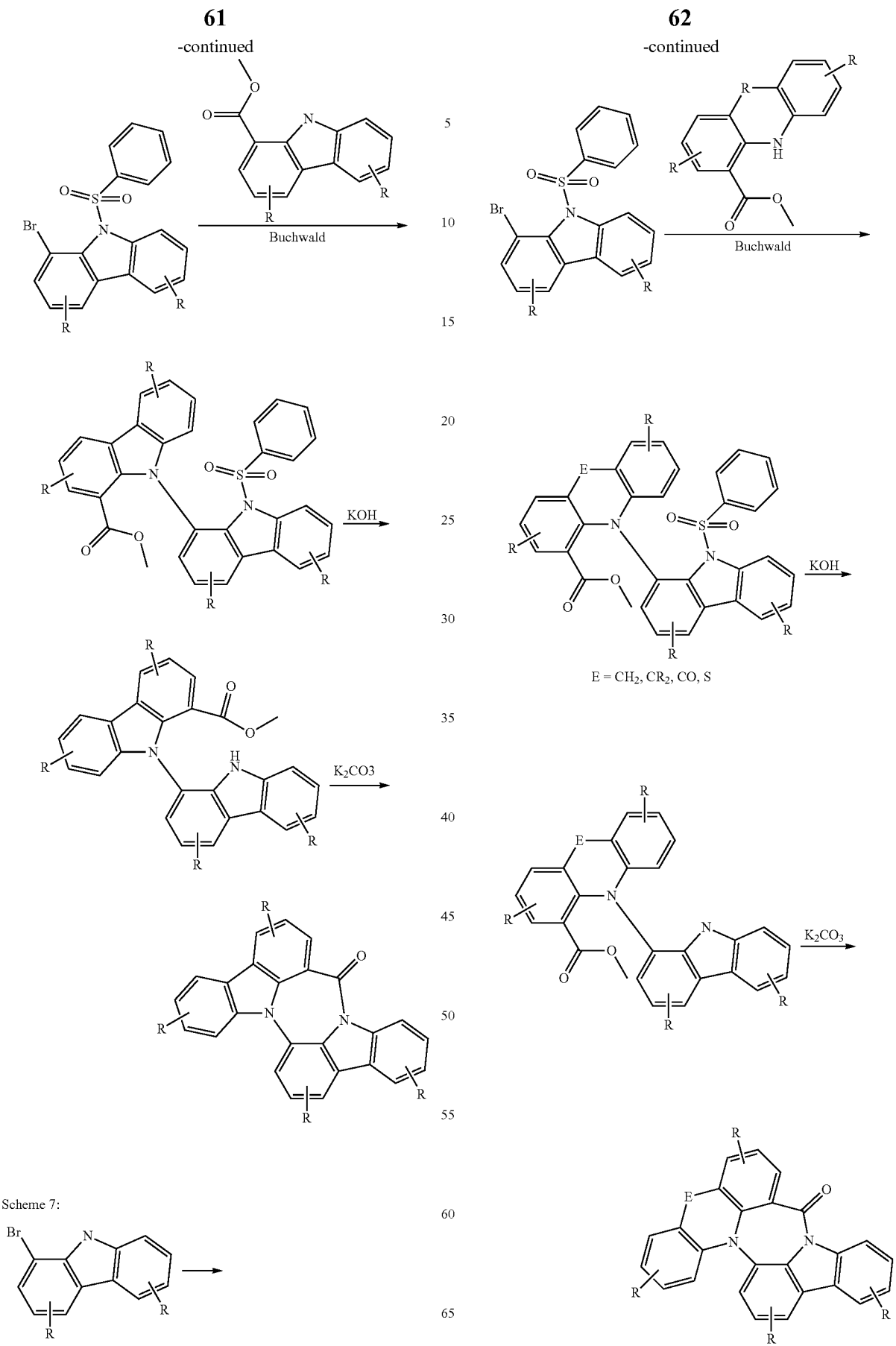
Scheme 7:

Scheme 8:

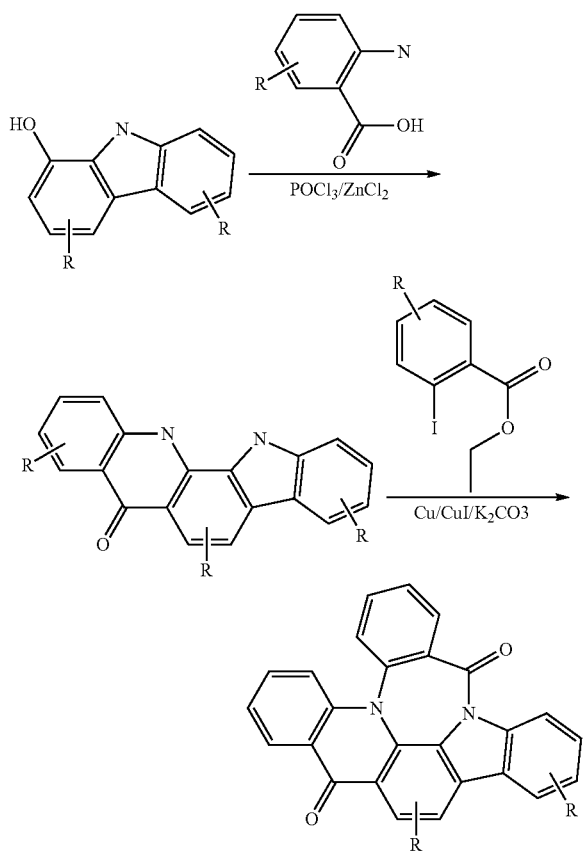

The present invention therefore furthermore relates to a process for the preparation of a compound of the formula (1) by reaction of a cis-indolocarbazole derivative with an aryl or heteroaryl derivative which is substituted in the ortho-positions by halogen, preferably iodine, and an acid derivative. The acid derivative here is preferably a carboxylic acid ester, a carboxylic acid halide, a sulfonic acid halide, a phosphinyl halide or a phosphinyl oxyhalide.

The compounds according to the invention described above, in particular compounds which are substituted by reactive leaving groups, such as bromine, iodine, chlorine, boronic acid or boronic acid ester, or by reactive, polymerisable groups, such as olefins or oxetanes, can be used as monomers for the preparation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as a crosslinked or uncrosslinked layer.

The invention therefore furthermore relates to oligomers, polymers or dendrimers comprising one or more of the compounds according to the invention indicated above, where one or more bonds are present from the compound according to the invention to the polymer, oligomer or dendrimer.

Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers, where the units of the formula (1) or the preferred embodiments mentioned above are present in a proportion of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also comprise further units, for example hole-transport units, in particular those based on triarylamines, and/or electron-transport units. In addition, the polymers can either comprise triplet emitters in copolymerised form or mixed in as a blend. Precisely the combination of units of the formula (1) or the preferred embodiments mentioned above with triplet emitters gives particularly good results.

Furthermore, the compounds of the formula (1) or the preferred embodiments mentioned above may also be functionalised further and thus converted into extended structures. An example which may be mentioned here is the reaction with arylboronic acids by the Suzuki method or with primary or secondary amines by the Hartwig-Buchwald method. Thus, the compounds of the formula (1) or the preferred embodiments mentioned above can also be bonded directly to phosphorescent metal complexes or also to other metal complexes.

The compounds according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds according to the invention mentioned above in an electronic device, in particular in an organic electroluminescent device.

The present invention again furthermore relates to an electronic device comprising at least one of the compounds according to the invention mentioned above. The preferences stated above likewise apply to the electronic devices.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al.,

*Nature Photonics* 2008, 1-4), but preferably organic electroluminescent devices (OLEDs), particularly preferably phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013).

The compound according to the invention in accordance with the embodiments indicated above can be employed in various layers, depending on the precise structure. Preference is given to an organic electroluminescent device comprising a compound of the formula (1) or the preferred embodiments mentioned above as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a further embodiment of the invention, the organic electroluminescent device comprises the compound of the formula (1) or the preferred embodiments mentioned above in an optical coupling-out layer. An optical coupling-out layer here is taken to mean a layer which is not located between the anode and cathode, but instead is applied to an electrode outside the actual device, for example between an electrode and a substrate, in order to improve the optical coupling out.

In a preferred embodiment of the invention, the compound of the formula (1) or the preferred embodiments mentioned above is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or the preferred embodiments mentioned above is employed as matrix material for an emitting compound in an emitting layer, it is preferably employed in combination with one or more phosphorescent materials (triplet emitters). Phosphorescence in the sense of this invention is taken to mean the luminescence from an excited state of relatively high spin multiplicity, i.e. a spin state >1, in particular from an excited triplet state. For the purposes of this application, all luminescent complexes containing transition metals or lanthanides, in particular all iridium, platinum and copper complexes, are to be regarded as phosphorescent compounds.

The mixture comprising the compound of the formula (1) or the preferred embodiments mentioned above and the emitting compound comprises between 99 and 1% by vol., preferably between 98 and 10% by vol., particularly preferably between 97 and 60% by vol., in particular between 95 and 80% by vol., of the compound of the formula (1) or the preferred embodiments mentioned above, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or the preferred embodiments mentioned above as matrix material for a phosphorescent emitter in combination with a further matrix material. Particularly suitable matrix materials which can be employed in combination with the compounds of the formula (1) or the preferred embodiments mentioned above are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or the unpublished application DE 102009023155.2 or DE 102009031021.5, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306 or the unpublished application DE 102009053382.6, DE 102009053644.2 or DE 102009053645.0, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with the unpublished applications DE 102009048791.3 and DE 102009053836.4. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373, US 2005/0258742 and WO 2010/086089. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) or the preferred embodiments mentioned above is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxyquinolinate).

In yet a further preferred embodiment of the invention, the compound of the formula (1) or the preferred embodiments mentioned above is employed in a hole-blocking layer. A hole-blocking layer is taken to mean a layer which is directly adjacent to an emitting layer on the cathode side.

It is furthermore possible to use the compound of the formula (1) or the preferred embodiments mentioned above both in a hole-blocking layer or electron-transport layer and as matrix in an emitting layer.

In yet a further embodiment of the invention, the compound of the formula (1) or the preferred embodiments mentioned above is employed in a hole-transport layer or in an electron-blocking layer or exciton-blocking layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) according to the invention or the preferred embodiments mentioned above.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds, which are obtained, for example, by suitable substitution, are necessary for this purpose. These processes are also particularly suitable for oligomers, dendrimers and polymers.

Also possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished by the following surprising advantages over the prior art:

1. The compounds according to the invention or compounds of the formula (1) or the preferred embodiments mentioned above, employed as matrix material for fluorescent or phosphorescent emitters, result in very high efficiencies and long lifetimes. This applies, in particular, if the compounds are employed as matrix material for a phosphorescent emitter.
2. The compounds according to the invention or compounds of the formula (1) or the preferred embodiments mentioned above are suitable not only as matrix for red- and green-phosphorescent compounds, but, in particular, also for blue-phosphorescent compounds.
3. On use as matrix material for phosphorescent compounds, very good results are also achieved with a low emitter concentration. This is frequently not the case with matrix materials in accordance with the prior art, but is desirable in view of the rarity of the metals, such as iridium or platinum, usually used in phosphorescent compounds.
4. In contrast to many compounds in accordance with the prior art, which undergo partial or complete pyrolytic decomposition on sublimation, the compounds according to the invention have high thermal stability.
5. The compounds according to the invention, employed in organic electroluminescent devices, result in high efficiencies and in steep current/voltage curves with low use voltages.
6. The compounds according to the invention also result in very good properties with respect to the efficiency, lifetime and operating voltage of organic electroluminescent devices on use as electron-transport material.

These above-mentioned advantages are not accompanied by an impairment in the other electronic properties.

The invention is explained in greater detail by the following examples, without wishing to restrict it thereby. The person skilled in the art will be able to use the descriptions to carry out the invention throughout the range disclosed and to prepare further compounds according to the invention without inventive step and use them in electronic devices or use the process according to the invention.

EXAMPLES

The following syntheses are carried out under a protective-gas atmosphere, unless indicated otherwise. The starting materials can be purchased from ALDRICH or ABCR (palladium(II) acetate, tri-o-tolylphosphine, inorganics, solvents). The synthesis of 11,12-dihydroindolo[2,3-a]carbazole can be carried out in accordance with the literature (Bulletin of the Chemical Society of Japan 2007, 80 (6), 1199-1201). The syntheses of bisindole (Journal of Organic Chemistry 2007, 72(9), 3537-3542) and 1-bromocarbazole (Journal of Organic Chemistry 2001, 66(25), 8612-8615), 1-hydroxycarbazole (Journal of Organic Chemistry 1988, 53(4), 794-9), 1,10-dihydropyrrolo[2,3-a]carbazole (Khimiya Geterotsiklicheskikh Soedinenii 1979, (10), 1362-6) and 1H,8H-pyrrolo[3,2-g]indole (Tetrahedron Letters 2009, 50 (13), 1469-1471) and 1,8-dihydro-2,7-diphenyl-benzo[2,1-b:3,4-b']dipyrrole (Tetrahedron Letters 2009, 50 (13), 1469-1471) are likewise known from the literature.

Example 1

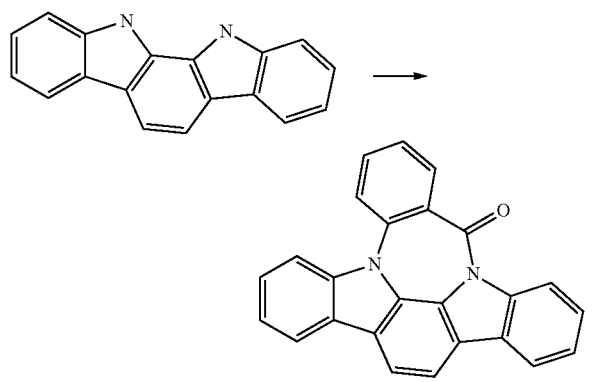 [SMILES: c1ccc2c(c1)[nH]c1c2ccc2c3ccccc3[nH]c21 ; O=c1c2ccccc2n2c3ccccc3c3ccc4c5ccccc5n1c4c32]

37.4 g (145 mmol) of 11,12-dihydroindolo[2,3-a]carbazole are added to 23 ml (159.5 mmol) of methyl 2-iodobenzoate in 150 ml of di-n-butyl ether, and the solution is degassed. 10 g (158 mmol) of copper powder, 1.38 g (7 mmol) of copper(I) iodide and 22 g (159.6 mmol) of $K_2CO_3$ are subsequently added to the mixture, which is then stirred at 144° C. under protective gas for 4 days. The organic phase is dried over $MgSO_4$, and the solvent is removed in vacuo. The residue is recrystallised from acetone and finally sublimed in a high vacuum. Yield: 20.9 g (58.4 mmol), 40% of theory, purity according to HPLC 99.9%.

Example 2

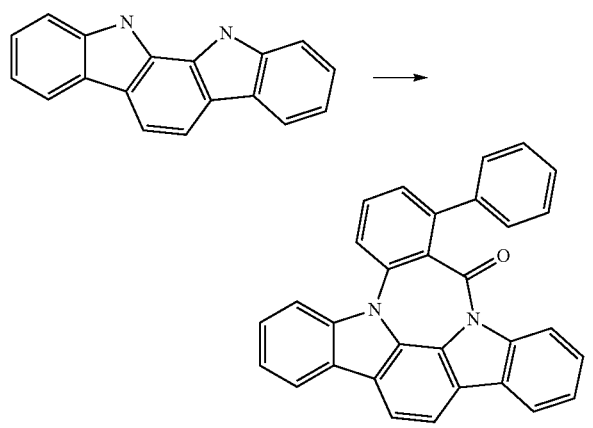

The compound is synthesised by the same procedure as Example 1 by reaction of 37.4 g (145 mmol) of 11,12-dihy-droindolo[2,3-a]carbazole with 54 g (159.5 mmol) of methyl 3-iodobiphenyl-2-carboxylate. The residue is recrystallised from $CH_2Cl_2$/isopropanol and finally sublimed in a high vacuum. Yield: 24.5 g (56 mmol), 39% of theory, purity according to HPLC 99.9%.

Example 3

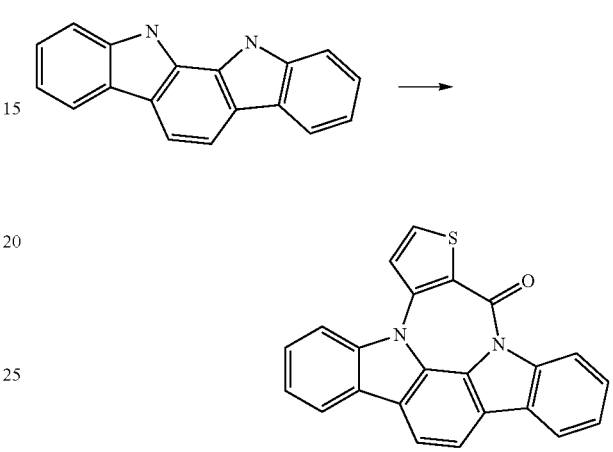

The compound is synthesised by the same procedure as Example 1 by reaction of 37.4 g (145 mmol) of 11,12-dihy-droindolo[2,3-a]carbazole with 42 g (159.5 mmol) of methyl 3-iodothiophene-2-carboxylate. The residue is recrystallised from $CH_2Cl_2$/isopropanol and finally sublimed in a high vacuum. Yield: 22.6 g (62 mmol), 43% of theory, purity according to HPLC 99.9%.

Example 4

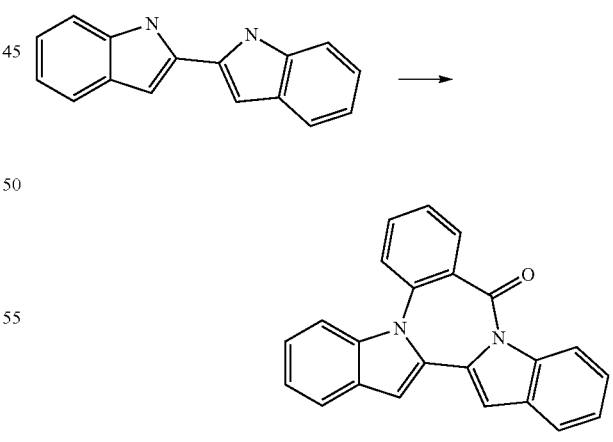

The compound is synthesised by the same procedure as Example 1 by reaction of 33.6 g (145 mmol) of bisindole with 23 ml (159.5 mmol) of methyl 2-iodobenzoate. The residue is recrystallised from toluene and finally sublimed in a high vacuum. Yield: 22.4 g (66 mmol), 47% of theory, purity according to HPLC 99.9%.

Example 5

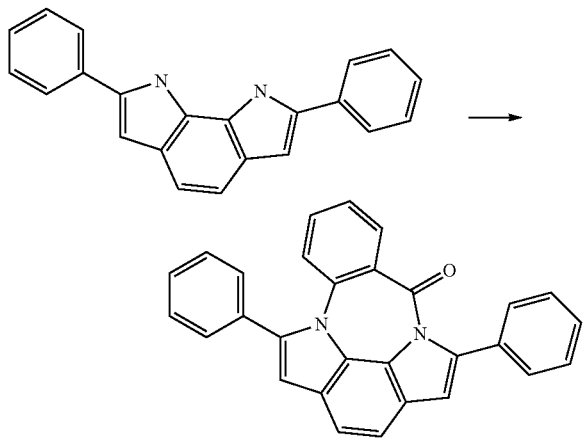

The compound is synthesised by the same procedure as Example 1 by reaction of 44 g (145 mmol) of 1,8-dihydro-2,7-diphenylbenzo[2,1-b:3,4-b]-dipyrrole with 23 ml (159.5 mmol) of methyl 2-iodobenzoate. The residue is recrystallised from toluene and finally sublimed in a high vacuum. Yield: 20.84 g (50 mmol), 35% of theory, purity according to HPLC 99.9%.

Example 6

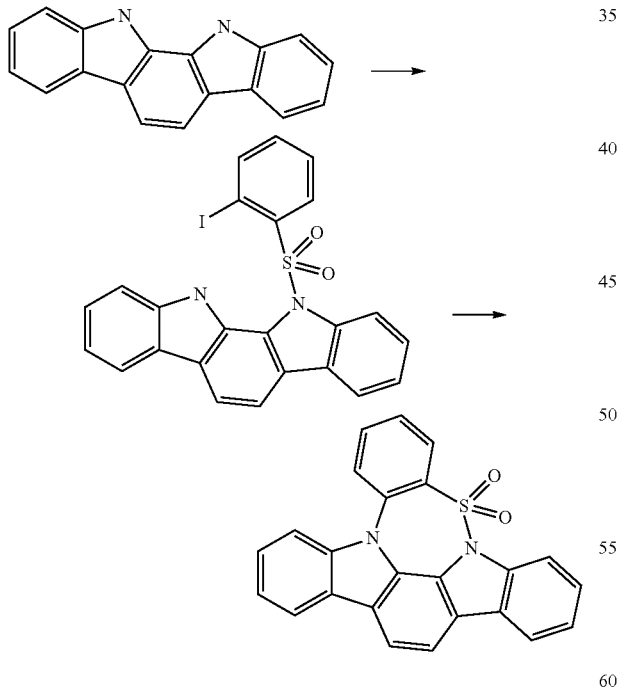

1st step: 11-(2-iodobenzenesulfonyl)-11,12-dihydro-11,12-diazaindeno[2,1-a]fluorene 43 g (169 mmol) of 11,12-dihydroindolo[2,3-a]carbazole are initially introduced in 1000 ml of THF, and 8.9 g (223.3 mmol) of NaH (60% in oil) are added at 0° C. 24 g (80 mmol) of 2-iodobenzenesulfonyl chloride are subsequently added to the mixture, which is then stirred at 40° C. for 12 h. The organic phase is dried over MgSO₄, and the solvent is removed in vacuo. The residue is recrystallised from acetone and finally sublimed in a high vacuum. Yield: 29 g (574 mmol), 72% of theory, purity according to HPLC 99.9%.

2nd Step

The ring closure is carried out by the same procedure as Example 1 by reaction of 46 g (145 mmol) of 11-(2-iodobenzenesulfonyl)-11,12-dihydro-11,12-diazaindeno[2,1-a]fluorene with 10 g (158 mmol) of copper powder, 1.38 g (7 mmol) of copper(I) iodide and 22 g (159.6 mmol) of $K_2CO_3$. The residue is recrystallised from $CH_2Cl_2$/isopropanol and finally sublimed in a high vacuum. Yield: 11.9 g (30 mmol), 38% of theory, purity according to HPLC 99.9%.

Example 7

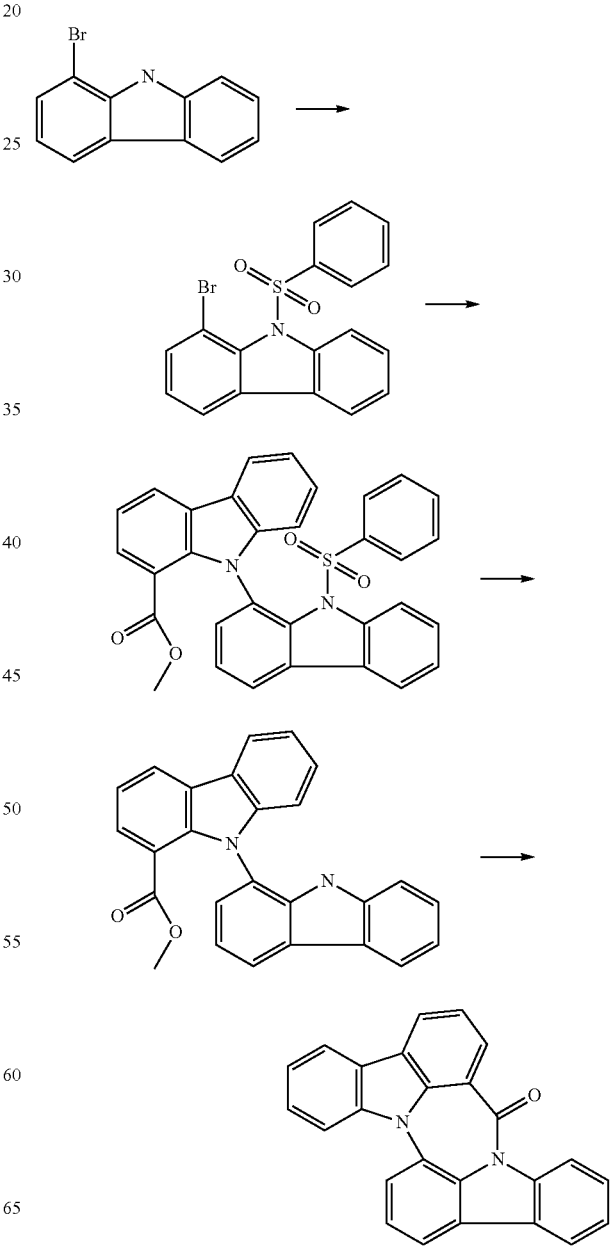

1st step: 9-benzenesulfonyl-1-bromo-9H-carbazole 19.6 g (80 mmol) of 1-bromocarbazole are initially introduced in 1000 ml of THF, and 8.9 g (223.3 mmol) of NaH (60% in oil) are added at 0° C. 24 g (80 mmol) of 2-iodobenzenesulfonyl chloride are subsequently added to the mixture, which is then stirred at 40° C. for 12 h. The organic phase is dried over MgSO$_4$, and the solvent is removed in vacuo. The residue is recrystallised from acetone and finally sublimed in a high vacuum. Yield: 29 g (574 mmol), 72% of theory, purity according to HPLC 99.9%.

2nd step: methyl 9-benzenesulfonyl-9H-[1,9']bicarbazolyl-1'-carboxylate 8.0 g (42.2 mmol) of copper(I) iodide, 11.7 ml (97.5 mmol) of trans-cyclo-hexanediamine are added to a well-stirred suspension of 26.3 g (117 mmol) of methyl 9H-carbazole-1-carboxylate, 45.2 g (117 mmol) of 9-benzenesulfonyl-1-bromo-9H-carbazole and 416.4 g (1961 mmol) of potassium phosphate in 1170 ml of dioxane, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol. Yield: 43 g (81 mmol), 70% of theory.

3rd step: methyl 9H-[1,9']bicarbazolyl-1'-carboxylate 65 g (123 mmol) of methyl 9-benzenesulfonyl-9H-[1,9']bicarbazolyl-1'-carboxylate and 48 g (856 mmol) of potassium hydroxide in 65 ml of dimethyl sulfoxide and 21 ml of water are heated at 60° C. for 1 h. The mixture is subsequently cooled to room temperature, neutralised using 1 M HCl solution and extracted with dichloromethane. The solvent is evaporated in vacuo, and the residue is purified by chromatography (heptane/ethyl acetate 10:1). Yield: 45 g (116 mmol), 95% of theory.

4th Step: Cyclisation 22 g (159.6 mmol) of K$_2$CO$_3$ are added to 56.5 g (145 mmol) of methyl 9H-[1,9']bicarbazolyl-1-carboxylate in 151 ml of di-n-butyl ether, and the mixture is stirred at 144° C. under protective gas for 4 days. The organic phase is dried over MgSO$_4$, and the solvent is removed in vacuo. The residue is recrystallised from acetone and finally sublimed in a high vacuum. Yield: 25 g (69.7 mmol), 49% of theory, purity according to HPLC 99.9%.

Example 8

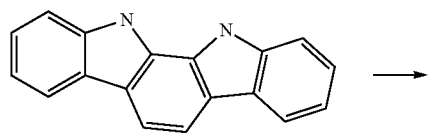

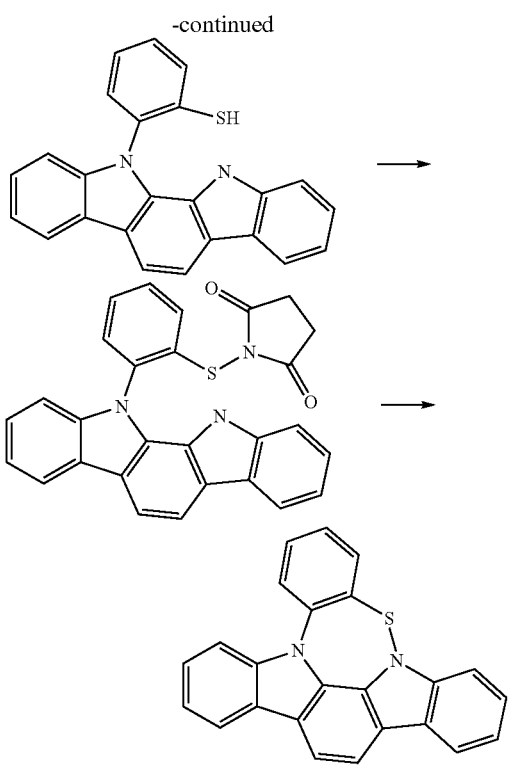

1st step: 2-(12H-11,12-diazaindeno[2,1-a]fluoren-11-yl)benzenethiol 25 g (96.6 mmol) of 11,12-dihydroindolo[2,3-a]carbazole are added to 12.5 g (48 mmol) of 2-iodobenzenethiol in 80 ml of di-n-butyl ether, and the solution is degassed. 6.6 g (0.105 mmol) of copper powder, 0.92 g (0.003 mmol) of copper(I) iodide and 14.6 g (106.6 mmol) of K$_2$CO$_3$ are subsequently added to the mixture, which is then stirred at 144° C. under protective gas for 4 days. The organic phase is dried over MgSO$_4$, and the solvent is removed in vacuo. The residue is recrystallised from acetone and finally sublimed in a high vacuum. Yield: 22.5 g (61 mmol), 66% of theory, purity according to HPLC 89.4%.

2nd step: 1-[2-(12H-11,12-diazaindeno[2,1-a]fluoren-1'-yl)phenyl-sulfanyl]pyrrolidine-2,5-dione 27.3 g (75 mmol) of 2-(12H-11,12-diazaindeno[2,1-a]fluoren-11-yl)-benzenethiol are added to a solution of 10 g (75 mmol) of NCS in 150 ml of CH$_2$Cl$_2$ at 0° C., 10.5 ml (75.3 mmol) of Et$_3$N are subsequently added, and the mixture is stirred at room temperature for 18 h. The organic phase is dried over MgSO$_4$, and the solvent is removed in vacuo. The residue is recrystallised from acetone and finally sublimed in a high vacuum. Yield: 30 g (66 mmol), 85% of theory, purity according to HPLC 88.3%.

3rd Step: Cyclisation

A solution of 4.6 g (10 mmol) of 1-[2-(12H-11,12-diazaindeno[2,1-a]fluoren-11-yl)phenylsulfanyl]pyrrolidine-2,5-dione in 40 ml of CH$_2$Cl$_2$ is added to a solution of 0.9 g (5 mmol) of N,N-dimethyltryptamine, 0.2 g (0.5 mmol) of tetrabutylammonium hydrogensulfate and 5 ml of 50% KOH solution in 25 ml of CH$_2$Cl$_2$, and the mixture is stirred at room temperature for 3 h. 0.2 g (0.5 mmol) of tetrabutylammonium hydrogensulfate is subsequently again added, and the mixture is stirred for a further 3 h. The organic phase is dried over MgSO$_4$, and the solvent is removed in vacuo. The residue is recrystallised from acetone and finally sublimed in a high vacuum. Yield: 2.4 g (6.5 mmol), 66% of theory, purity according to HPLC 99.9%.

Example 9

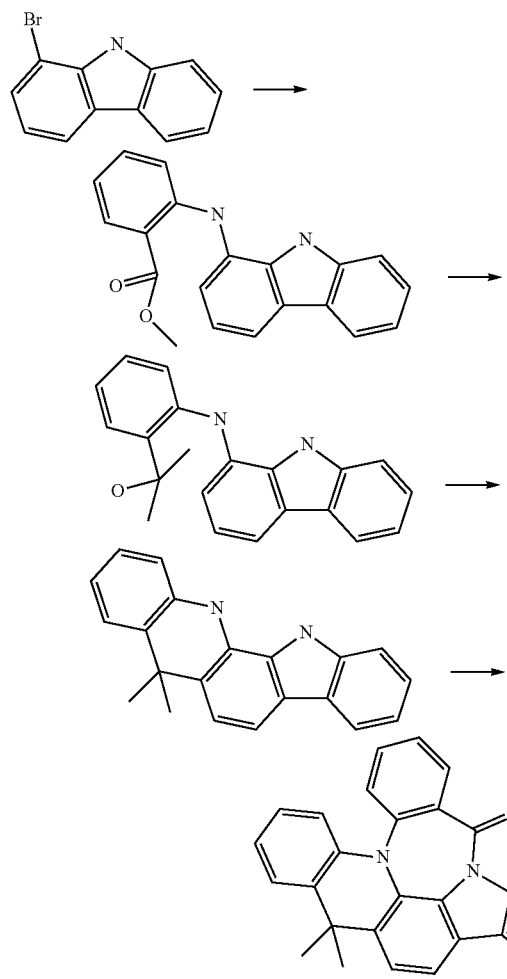

1st step: methyl 2-(9H-carbazol-1-ylamino)benzoate 35.51 g (234.9 mmol) of methyl anthranilate are dissolved in 500 ml of toluene and degassed well. 52 g (213 mmol) of 1-bromocarbazole, 2.1 g (10.7 mmol) of 4,5-bis(diphenylphosphino)-9,9-dimethylxanthene, 1.19 g (5.34 mmol) of Pd(OAc)$_2$ and 76.5 g (234.9 mmol) of Cs$_2$CO$_3$ are added, and the mixture is then degassed and stirred at 100° C. under a protective-gas atmosphere for 24 h. The solids are subsequently filtered off via Celite, and the organic phase is washed with water, dried over MgSO$_4$ and evaporated. The crude product is washed by stirring with hot heptane, giving 57.4 g (108 mmol), 86% of theory, purity according to HPLC 86%.

2nd step: 2-[2-(9H-carbazol-1-ylamino)phenyl]propan-2-ol 71.7 g (227 mmol) of methyl 2-(9H-carbazol-1-ylamino) benzoate are initially introduced in 2000 ml of THF under protective gas and cooled to 0° C. 300 ml of 2 M methylmagnesium chloride solution are added dropwise at this temperature, and the mixture is subsequently brought to room temperature overnight. 600 ml of saturated NH$_4$Cl solution and 900 ml of water/conc. HCl 8:1 are added to the solution. The phases are separated, and the solvent is removed in vacuo. The content of product according to $^1$H-NMR is about 90% with an overall yield of 64.5 g (90%).

3rd step: 7,7-dimethyl-12,13-dihydro-7H-indolo[3,2-c]acridine 63 g (200 mmol) of 2-[2-(9H-carbazol-1-ylamino)phenyl] propan-2-ol are initially introduced in 268 g (2734 mmol) of polyphosphoric acid under protective gas and cooled to 0° C. The mixture is subsequently stirred at 100° C. for 3 h and then cooled to room temperature. Water is added to the mixture with ice cooling, the mixture is extracted with ethyl acetate, and the solvent is removed in vacuo. The content of product according to $^1$H-NMR is about 96% with an overall yield of 53 g (90%).

4th Step: Cyclisation 43 g (145 mmol) of 7,7-dimethyl-12,13-dihydro-7H-indolo[3,2-c]acridine are added to 23 ml (159.5 mmol) of methyl 2-iodobenzoate in 150 ml of di-n-butyl ether, and the solution is degassed. 10 g (0.158 mmol) of copper powder, 1.38 g (0.007 mmol) of copper(I) iodide and 22 g (159.6 mmol) of K$_2$CO$_3$ are subsequently added to the mixture, which is then stirred at 144° C. under protective gas for 4 days. The organic phase is dried over MgSO$_4$, and the solvent is removed in vacuo. The residue is recrystallised from acetone and finally sublimed in a high vacuum. Yield: 19.5 g (49 mmol), 34% of theory, purity according to HPLC 99.9%.

Example 10

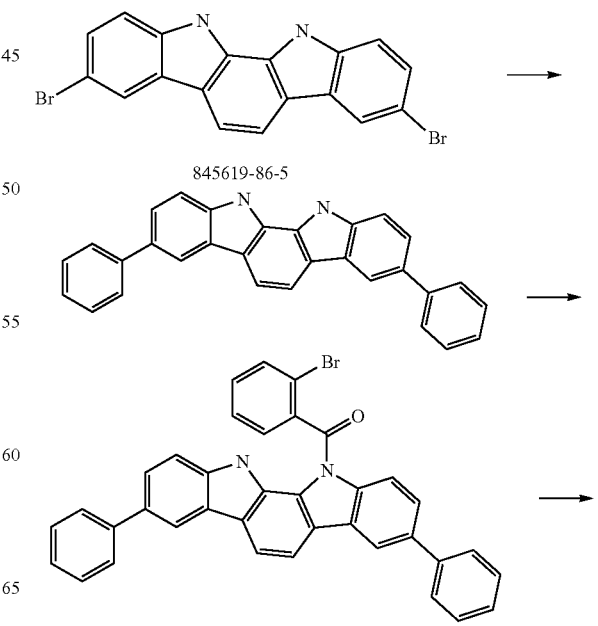

-continued

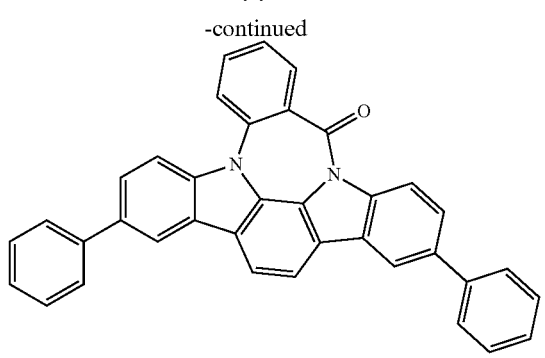

1st step: 3-[(Z)-1-eth-(E)-ylidenepenta-2,4-dienyl]-8-phenyl-11,12-dihydro-11,12-diazaindeno[2,1-a]fluorene 13.3 g (110.0 mmol) of phenylboronic acid, 20 g (50 mmol) of 3,8-dibromo-11,12-dihydroindolo[2,3-a]carbazole and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol. The yield is 16 g (39 mmol), corresponding to 80% of theory.

2nd step: (2-bromophenyl)-(3,8-diphenyl-12H-11,12-diazaindeno-[2,1-a]fluoren-11-yl)methanone 2.1 g (52.5 mmol) of NaH (60% in mineral oil) are dissolved in 500 ml of THF under a protective atmosphere. 20 g (50 mmol) of 3-[(Z)-1-eth-(E)-ylidenepenta-2,4-dienyl]-8-phenyl-11,12-dihydro-11,12-diazaindeno[2,1-a]-fluorene and 11.5 g (52.5 mmol) of 15-crown-5 dissolved in 200 ml of THF are added. After 1 h at room temperature, a solution of 12 g (55 mmol) of 2-bromobenzoyl chloride in 250 ml of THF is added dropwise. The reaction mixture is stirred at room temperature for 18 h. After this time, the reaction mixture is poured onto ice and extracted three times with dichloromethane. The combined organic phases are dried over Na$_2$SO$_4$ and evaporated. The residue is extracted with hot toluene and recrystallised from toluene/n-heptane. The yield is 22 g (75%).

3rd Step 150 ml of di-n-butyl ether are added to 85 g (145 mmol) of (2-bromo-phenyl)-(3,8-diphenyl-12H-11,12-diazaindeno[2,1-a]fluoren-11-yl)methanone, and the solution is degassed. 10 g (158 mmol) of copper powder, 1.38 g (7 mmol) of copper(I) iodide and 22 g (159.6 mmol) of K$_2$CO$_3$ are subsequently added to the mixture, which is then stirred at 144° C. under protective gas for 4 days. The organic phase is dried over MgSO$_4$, and the solvent is removed in vacuo. The residue is recrystallised from acetone and finally sublimed in a high vacuum. Yield: 63 g (124 mmol), 86% of theory, purity according to HPLC 99.9%.

Example 11

Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs are presented in the following Examples I1-I10 (see Tables 1 and 2). Glass plates coated with structured ITO (indium tin oxide) in a thickness of 150 nm are coated with 20 nm of PEDOT (poly(3,4-ethylene-dioxy-2,5-thiophene), spin-coated from water; purchased from H. C. Starck, Goslar, Germany) for improved processing. These coated glass plates form the substrates to which the OLEDs are applied. The OLEDs have in principle the following layer structure: substrate/hole-transport layer (HTL)/interlayer (IL)/electron-blocking layer (EBL)/emission layer (EML)/electron-transport layer (ETL)/optional electron-injection layer (EIL) and finally a cathode. The cathode is formed by an aluminium layer with a thickness of 100 nm. The precise structure of the OLEDs is shown in Table 1. The materials used for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. An expression such as M1:TEG1 (95%:5%) here means that material M1 is present in the layer in a proportion by volume of 95% and TEG1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), and the lifetime are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. SE1000 and LE1000 denote the current and power efficiencies achieved at 1000 cd/m$^2$. Finally, EQE1000 is the external quantum efficiency at an operating luminous density of 1000 cd/m$^2$.

The data for the various OLEDs are summarised in Table 2.

Some of the examples are explained in greater detail below. However, it should be pointed out that this only represents a selection of the data shown in Table 2.

Use of Compounds According to the Invention as Matrix Materials in Phosphorescent OLEDs On use of materials according to the invention as matrix for phosphorescent emitters, good voltages and in some cases very good efficiencies are obtained. In particular, materials M1 and M2 are distinguished by the fact that very high current efficiencies (62 cd/A, 17.1% EQE) are achieved for low emitter concentrations of 5% (Examples 11 and 12). This is not the case for a large number of conventional matrix materials and is advantageous from a technical point of view since the iridium complexes often employed as emitter are not sufficiently thermally stable for mass production with short tact times. The use of a relatively low emitter concentration allows lower vapour-deposition temperatures for the same tact time, enabling the problem of the thermal stability to be avoided. On operation at constant current, the luminous density of Examples 11 and 12 drops from an initial value of 8000 cd/m$^2$ to 6400 cd/m$^2$ after about 90 h. Further materials according to the invention likewise exhibit good performance data, as revealed by Table 2.

Use of Compounds According to the Invention as Electron-Transport Materials

The compounds according to the invention can furthermore be employed in the electron-transport layer of OLEDs. On combination of material ETM1 according to the invention with LiQ as electron-injection layer, a voltage of 4.7 V, a current efficiency of 51 cd/A and thus a good power efficiency of 35 lm/W are obtained for a green-phosphorescent OLED (Example 19).

TABLE 1

Structure of the OLEDs

| Ex. | HTL Thickness | IL Thickness | EBL Thickness | EML Thickness | ETL Thickness | EIL Thickness |
|---|---|---|---|---|---|---|
| I1 | SpA1 70 nm | HATCN 5 nm | BPA1 90 nm | M1:TEG1 (95%:5%) 30 nm | ST1:LiQ (50%:50%) 30 nm | — |

TABLE 1-continued

Structure of the OLEDs

| Ex. | HTL Thickness | IL Thickness | EBL Thickness | EML Thickness | ETL Thickness | EIL Thickness |
|---|---|---|---|---|---|---|
| I2 | SpA1 70 nm | HATCN 5 nm | BPA1 90 nm | M2:TEG1 (95%:5%) 30 nm | ST1:LiQ (50%:50%) 30 nm | — |
| I3 | SpA1 70 nm | HATCN 5 nm | BPA1 90 nm | M3:TER1 (85%:15%) 30 nm | ST1:LiQ (50%:50%) 30 nm | — |
| I4 | SpA1 70 nm | HATCN 5 nm | BPA1 90 nm | M4:TER1 (85%:15%) 30 nm | ST1:LiQ (50%:50%) 30 nm | — |
| I5 | SpA1 70 nm | HATCN 5 nm | BPA1 90 nm | M5:TEG1 (90%:10%) 30 nm | ST1:LiQ (50%:50%) 30 nm | — |
| I6 | SpA1 70 nm | HATCN 5 nm | BPA1 90 nm | M6:TEG1 (90%:10%) 30 nm | ST1:LiQ (50%:50%) 30 nm | — |
| I7 | SpA1 70 nm | HATCN 5 nm | BPA1 90 nm | M7:TEG1 (90%:10%) 30 nm | ST1:LiQ (50%:50%) 30 nm | — |
| I8 | SpA1 70 nm | HATCN 5 nm | BPA1 90 nm | M8:TEG1 (90%:10%) 30 nm | ST1:LiQ (50%:50%) 30 nm | — |
| I9 | SpA1 70 nm | HATCN 5 nm | BPA1 90 nm | IC1:TEG1 (90%:10%) 30 nm | ETM1 30 nm | LiQ 3 nm |
| I10 | SpA1 70 nm | HATCN 5 nm | BPA1 90 nm | M9:TEG1 (90%:10%) 30 nm | ST1:LiQ (50%:50%) 30 nm | — |

TABLE 2

Data for the OLEDs

| Ex. | U1000 (V) | SE1000 (cd/A) | LE1000 (lm/W) | EQE 1000 | CIE x/y at 1000 cd/m$^2$ |
|---|---|---|---|---|---|
| I1 | 3.7 | 62 | 54 | 17.1% | 0.34/0.62 |
| I2 | 3.8 | 59 | 49 | 16.2% | 0.35/0.61 |
| I3 | 4.6 | 6.1 | 4.2 | 9.1% | 0.69/0.31 |
| I4 | 4.3 | 5.8 | 4.2 | 8.6% | 0.69/0.31 |
| I5 | 5.1 | 34 | 21 | 9.2% | 0.35/0.61 |
| I6 | 3.9 | 54 | 44 | 15.3% | 0.36/0.61 |
| I7 | 5.1 | 44 | 27 | 12.1% | 0.37/0.60 |
| I8 | 3.8 | 48 | 40 | 13.2% | 0.37/0.60 |
| I9 | 4.7 | 51 | 35 | 13.9% | 0.35/0.61 |
| I10 | 3.7 | 52 | 50 | 14.7% | 0.36/0.61 |

TABLE 3

Structural formulae of the materials for the OLEDs

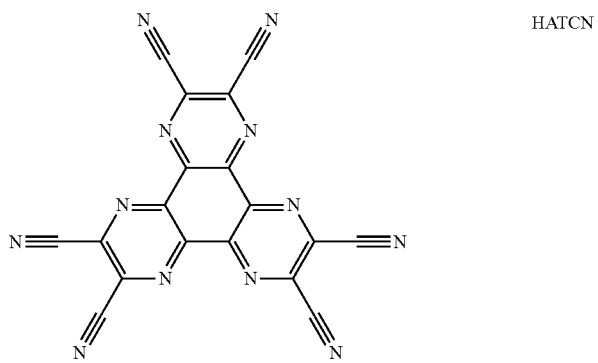

HATCN

TABLE 3-continued
Structural formulae of the materials for the OLEDs
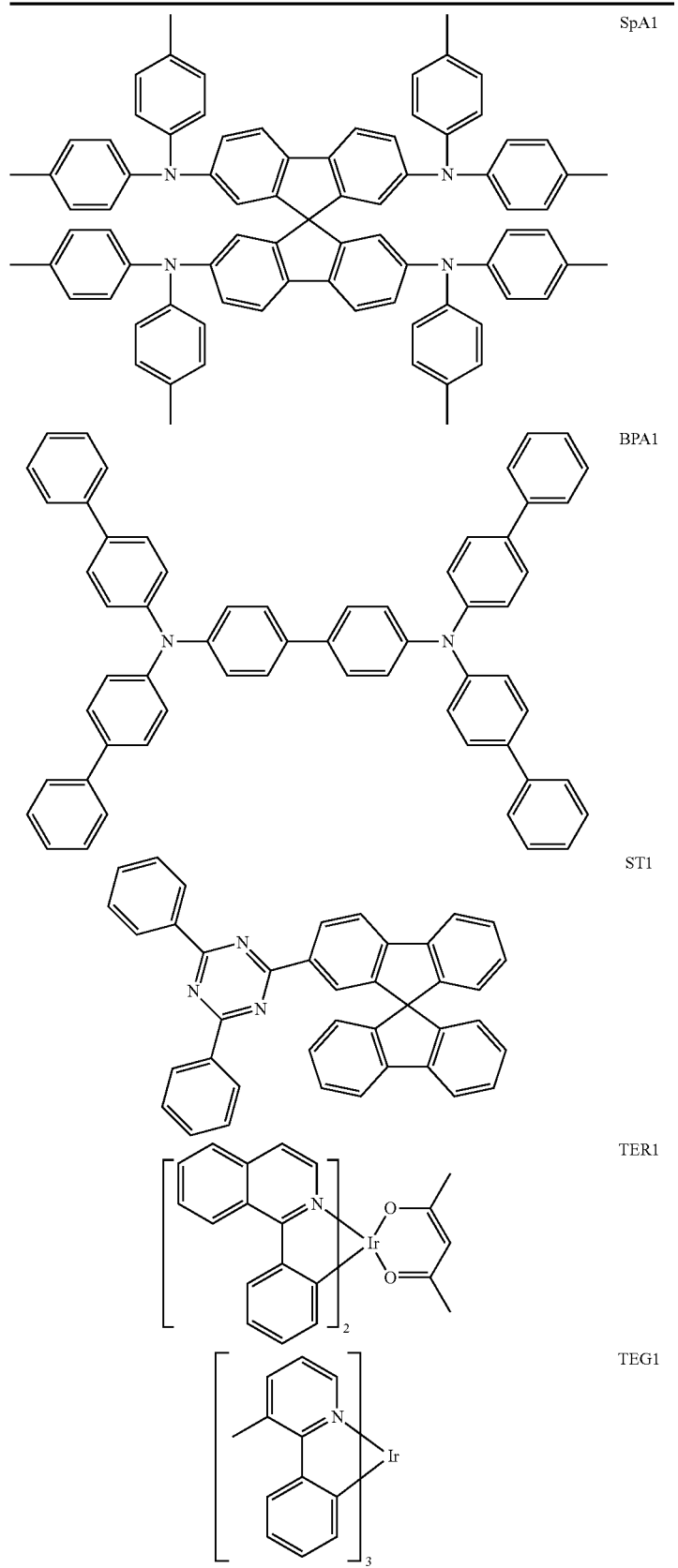

TABLE 3-continued
Structural formulae of the materials for the OLEDs
IC1
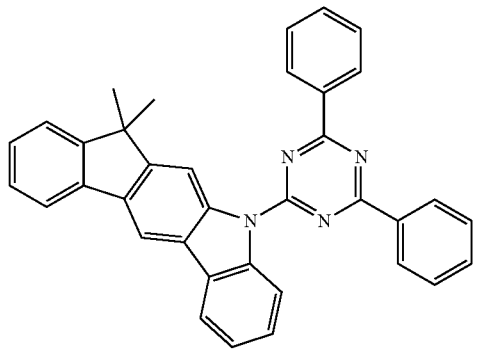 [SMILES: CC1(C)c2ccccc2-c2cc3c4ccccc4n(-c4nc(-c5ccccc5)nc(-c5ccccc5)n4)c3cc21]
M1
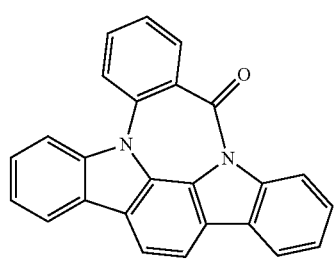 [SMILES: O=c1c2ccccc2n2c3ccccc3c3ccc4c5ccccc5n1c4c32]
(according to the invention)
M2
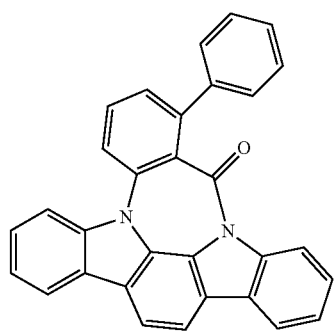 [SMILES: O=c1c2c(-c3ccccc3)cccc2n2c3ccccc3c3ccc4c5ccccc5n1c4c32]
(according to the invention)
M3
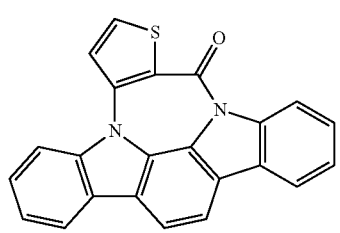 [SMILES: O=c1c2sccc2n2c3ccccc3c3ccc4c5ccccc5n1c4c32]
(according to the invention)
ETM1
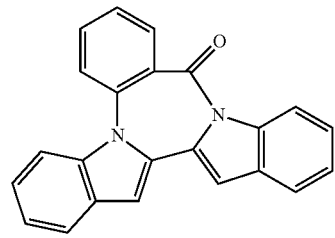 [SMILES: O=c1c2ccccc2n2c3ccccc3cc2c2cc3ccccc3n12]
(according to the invention)

TABLE 3-continued
Structural formulae of the materials for the OLEDs
M4
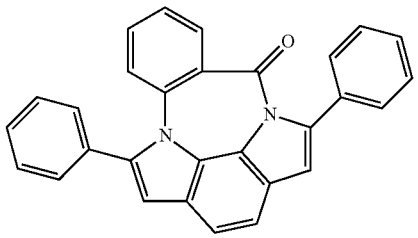 [SMILES: O=c1c2ccccc2n2c(-c3ccccc3)cc3ccc4cc(-c5ccccc5)n1c4c32]
(according to the invention)
M5
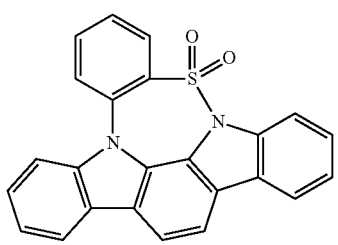 [SMILES: O=S1(=O)c2ccccc2-n2c3ccccc3c3ccc4c5ccccc5n1c4c32]
(according to the invention)
M6
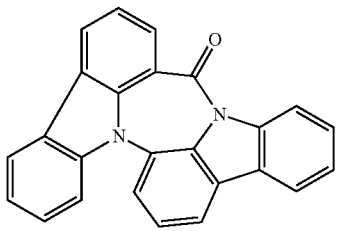 [SMILES: O=c1c2cccc3c4ccccc4n(c4cccc5c6ccccc6n1c54)c23]
(according to the invention)
M7
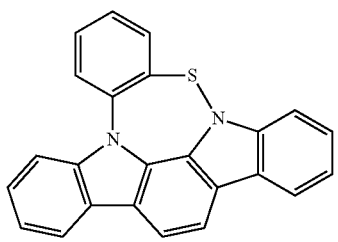 [SMILES: c1ccc2c(c1)sn1c3ccccc3c3ccc4c5ccccc5n2c4c31]
(according to the invention)
M8
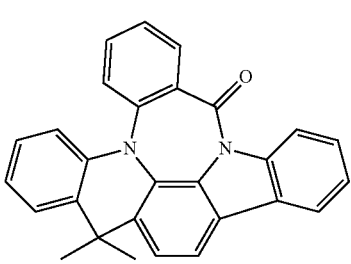 [SMILES: CC1(C)c2ccccc2N2c3ccccc3C(=O)n3c4ccccc4c4ccc1c2c43]
(according to the invention)
LiQ
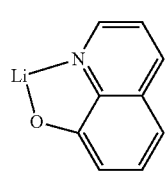

TABLE 3-continued

Structural formulae of the materials for the OLEDs

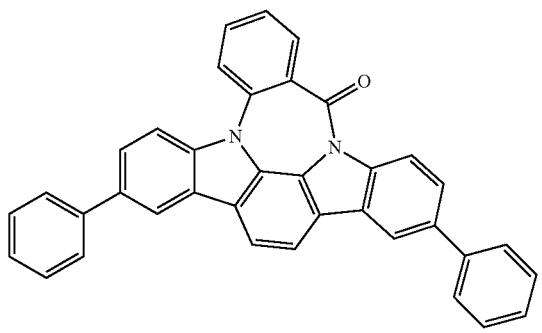 [SMILES: O=c1c2ccccc2n2c3ccc(-c4ccccc4)cc3c3ccc4c5cc(-c6ccccc6)ccc5n1c4c32]

M9

(according to the invention)

The invention claimed is:

1. A compound of the formula (1)

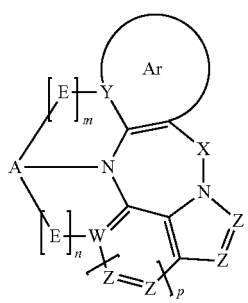

formula (1)

where the following applies to the symbols and indices used:

X is C=O, C(R)$_2$, O, S, C=S, SO or SO$_2$;

Y is C;

W is on each occurrence, identically or differently, CR or N, with the proviso that not more than three groups W in a ring stand for N, and with the further proviso that W=C if a group E is bonded to this group W;

Z is, identically or differently on each occurrence, CR or N; or two adjacent groups Z stand for a group of the formula (2)

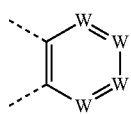

formula (2)

in which the dashed bonds indicate the linking of this unit;

E is, identically or differently on each occurrence, a single bond, C(R)$_2$, NR, O, S, C=O, C=S, C=NR, C=C(R)$_2$, Si(R)$_2$, BR, PR, P(=O)R, SO or SO$_2$;

Ar is a group of one of the following formulae (7), (8), (9), (10):

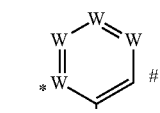

formula (7)

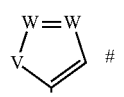

formula (8)

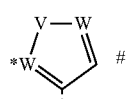

formula (9)

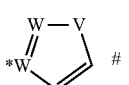

formula (10)

wherein the dashed bond indicates the link to N, # indicates the position of the link to X, * indicates the position of the link to E if a group E is present, and W and V stands for NR, O or S, wherein W is equal to C if a group E is bonded at this position; and wherein a maximum of one symbol W per ring stands for N and the remaining symbols W per ring stand for CR;

A is R if m =n =0, and is an aryl or heteroaryl group having 5 to 30 aromatic ring atoms, which may in each case be substituted by R, or a group —CR=CR—, —CR=N— or —N=N— if an index m or n =1 and the other index m or n =0, or is an aryl or heteroaryl group having 5 to 30 aromatic ring atoms, which may in each case be substituted by R, if the indices m =n =1;

R is selected on each occurrence, identically or differently, from H, D, F, Cl, Br, I, CN, NO$_2$, N(Ar$^1$)$_2$, N(R$^1$)$_2$, C(=O)Ar$^1$, P(=O)(Ar$^1$)$_2$, a straight-chain alkyl or thioalkyl group having 1 to 40 C atoms or a branched or cyclic alkyl or thioalkyl group having 3 to 40 C atoms or an alkenyl or alkynyl group having 2 to 40 C atoms, each of which is optionally substituted by one or more radicals R$^1$, where one or more non-adjacent CH$_2$ groups is optionally replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, S or CONR$^1$ and where one or more H atoms is optionally replaced by D, F, Cl, Br, I, CN or NO$_2$, an aromatic or heteroaromatic ring system having 5 to 80 aromatic ring atoms, which is optionally in each case be substituted by one or more radicals R$^1$, an aryloxy or heteroaryloxy group having 5 to 60 aromatic ring atoms, which is optionally substituted by one or more radicals R$^1$, or a combination of these systems, where two or more adjacent substituents R may optionally form a monocyclic or polycyclic, aliphatic, aromatic or heteroaromatic ring system, which is optionally substituted by one or more radicals R$^1$;

R$^1$ is selected on each occurrence, identically or differently, is H, D, F, Cl, Br, I, CN, NO$_2$, N(Ar$^1$)$_2$, N(R$^2$)$_2$, C(=O)Ar, C(=O)R$^2$, P(=O)(Ar$^1$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R$^2$, where one or more non-adjacent CH$_2$ groups is optionally replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more atoms is optionally replaced by D, F, Cl, Br, I, CN or NO$_2$, an aromatic or heteroaromatic ring system having 5 to 60 aromatic ring atoms, which is optionally in each case be substituted by one or more radicals R$^2$, an aryloxy or heteroaryloxy group having 5 to 60 aromatic ring atoms, which is optionally substituted by one or more radicals R$^2$, or a combination of these systems, where two or more adjacent substituents R may optionally form a monocyclic or polycyclic, aliphatic, aromatic or heteroaromatic ring system, which is optionally substituted by one or more radicals R$^2$;

R$^2$ is selected from the group consisting of H, D, F, CN, an aliphatic hydrocarbon radical having 1 to 20 C atoms, an aromatic or hetero-aromatic ring system having 5 to 30 aromatic ring atoms, in which one or more H atoms is optionally replaced by D, F, Cl, Br, I or CN, where two or more adjacent substituents R$^2$ may form a mono- or polycyclic, aliphatic, aromatic or heteroaromatic ring system with one another;

Ar$^1$ is on each occurrence, identically or differently, an aromatic or heteroaromatic ring system having 5-30 aromatic ring atoms, which is optionally substituted by one or more non-aromatic radicals R$^2$; two radicals Ar$^1$ which are bonded to the same N atom or P atom may also be bridged to one another here by a single bond or a bridge selected from N(R$^2$), C(R$^2$)$_2$ or O;

m is 0;

n is 0 or 1, where, for n=0, a group R instead of the group E is bonded to A;

p is 1;

wherein said heteroaryl groups and heteroaromatic ring systems contain at least one heteroatom selected from the group consisting of N, O, and S.

2. The compound according to claim 1, wherein E stands, identically or differently on each occurrence, for a single bond, CR$_2$, C=O, NR, O or S.

3. The compound according to claim 1, wherein A stands for a group of one of the following formulae (3), (4), (5) or (6):

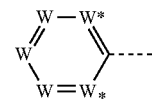

formula (3)

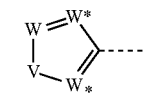

formula (4)

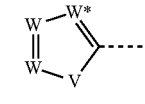

formula (5)

formula (6)

where the dashed bond indicates the link to N, * indicates the position of the link to E if a group E is present, W has the meaning given in claim 1, and W is equal to C if a group E is bonded at this position, and V stands for NR, O or S.

4. The compound according to claim 1, wherein the following applies to the symbols and indices used:

X is C=O, CR$_2$, S, O or SO$_2$;

E is, identically or differently on each occurrence, a single bond, CR$_2$, C=O, NR, O or S;

A is an aryl or heteroaryl group having 5 to 16 aromatic ring atoms, which may in each case be substituted by one or more radicals R, or a group —CR=CR—, —CR=N— or —N=N—;

Z=Z in the five-membered ring stands for a group of the formula (2) defined in claim 1;

Ar stands for a group of one of the following formulae (7) to (10):

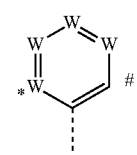

formula (7)

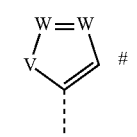

formula (8)

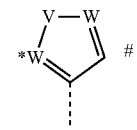

formula (9)

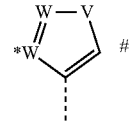

formula (10)

where the dashed bond indicates the link to N, # indicates the position of the link to X, * indicates the position of the link to E if a group E is present, and W has the meaning given in claim 1; W here is equal to C if a group E is bonded at this position; furthermore, V stands for NR, O, S or $CR_2$;
m is 0; and
n is 1.
5. The compound according to claim 1, wherein the compound is selected from the compounds of the following formulae (11) to (37):
formula (11)
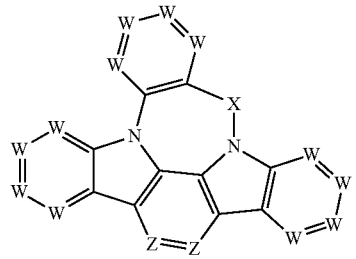
formula (14)
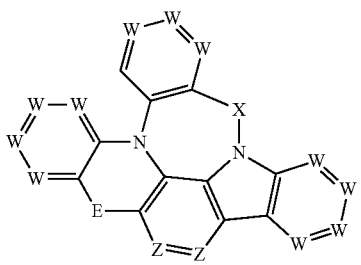
formula (15)
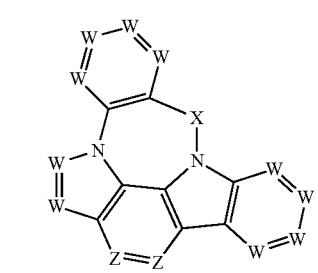
formula (16)
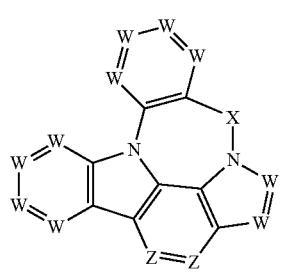
formula (17)
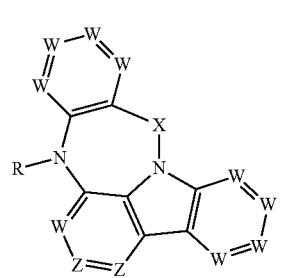
-continued
formula (18)
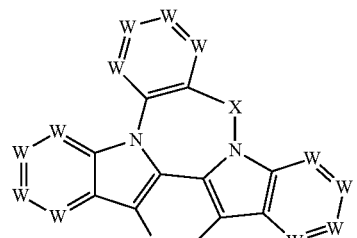
formula (19)
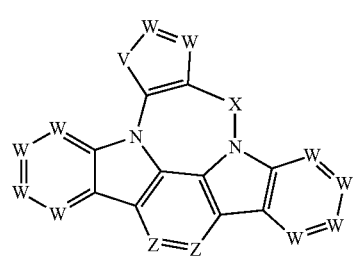
formula (20)
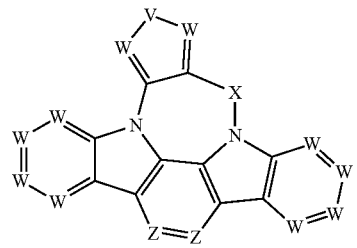
formula (21)
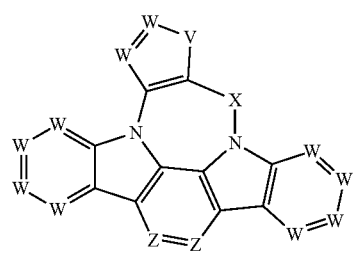
formula (24)
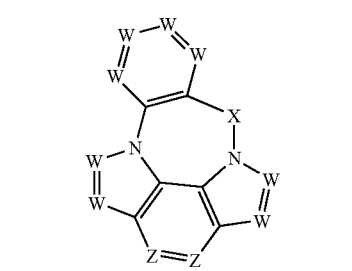
formula (25)
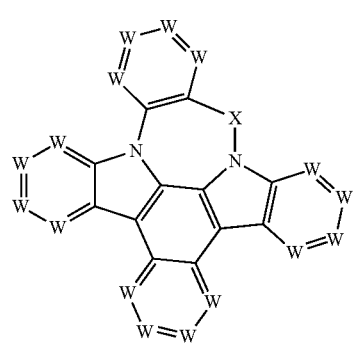

formula (28)
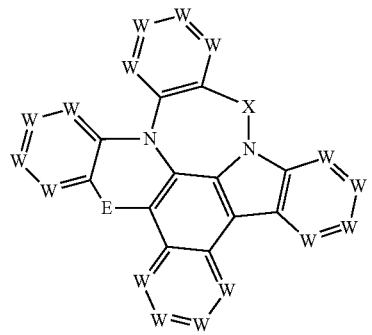
formula (29)
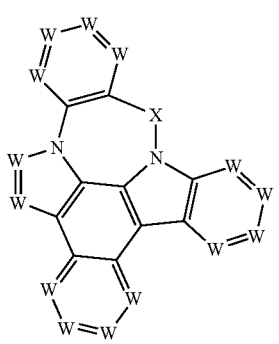
formula (30)
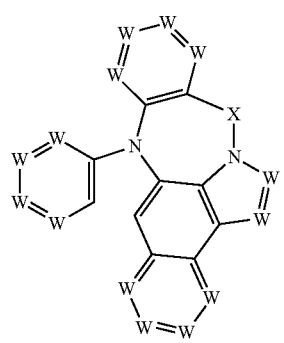
formula (31)
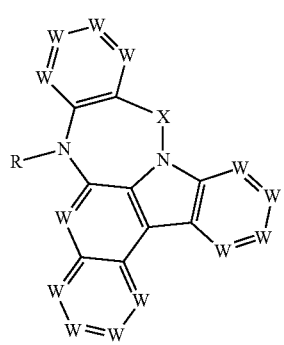
formula (32)
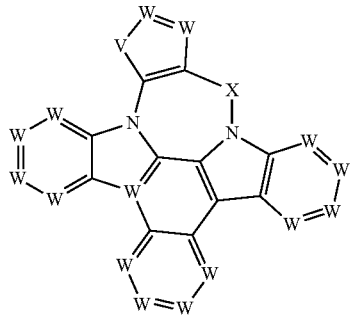
formula (33)
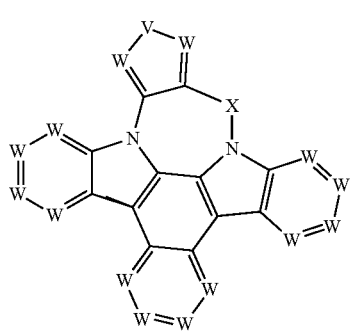
formula (34)
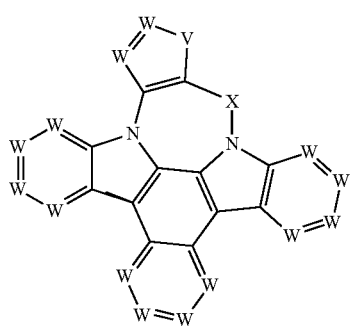
formula (37)
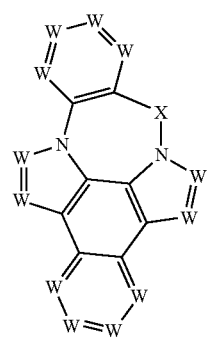
where the symbols used have the meanings given in claim 1.

6. The compound according to claim 1, wherein the compound is selected from the compounds of the following formulae (11a) to (37a):
formula (11a)
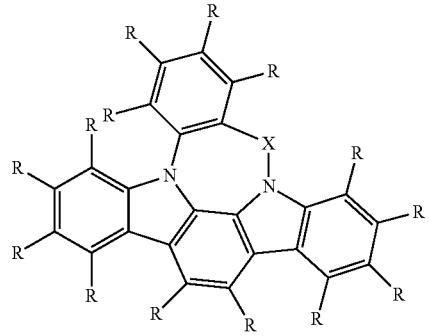
formula (14a)
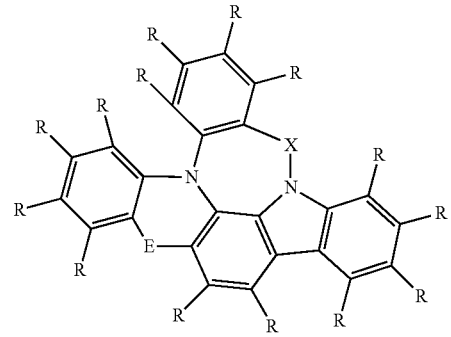
formula (15a)
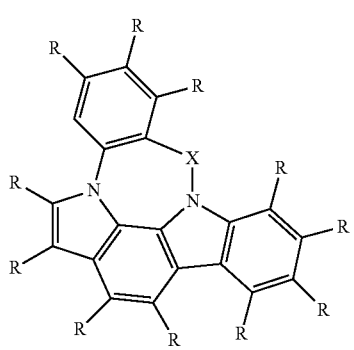
formula (16a)
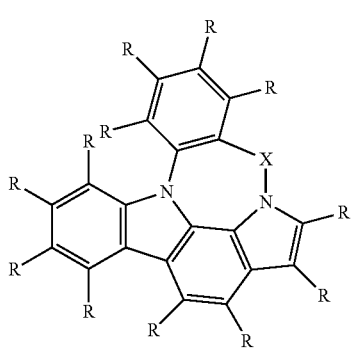
formula (17a)
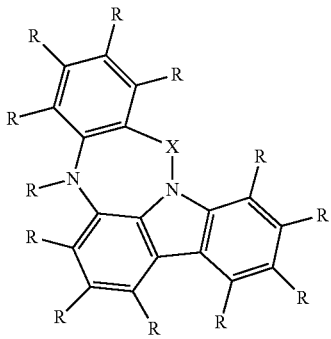
formula (18a)
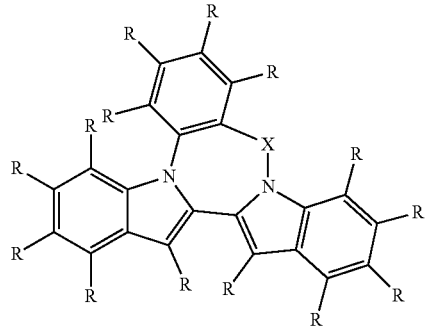
formula (19a)
formula (20a)
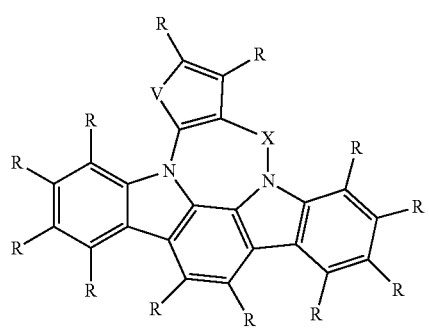
formula (21a)

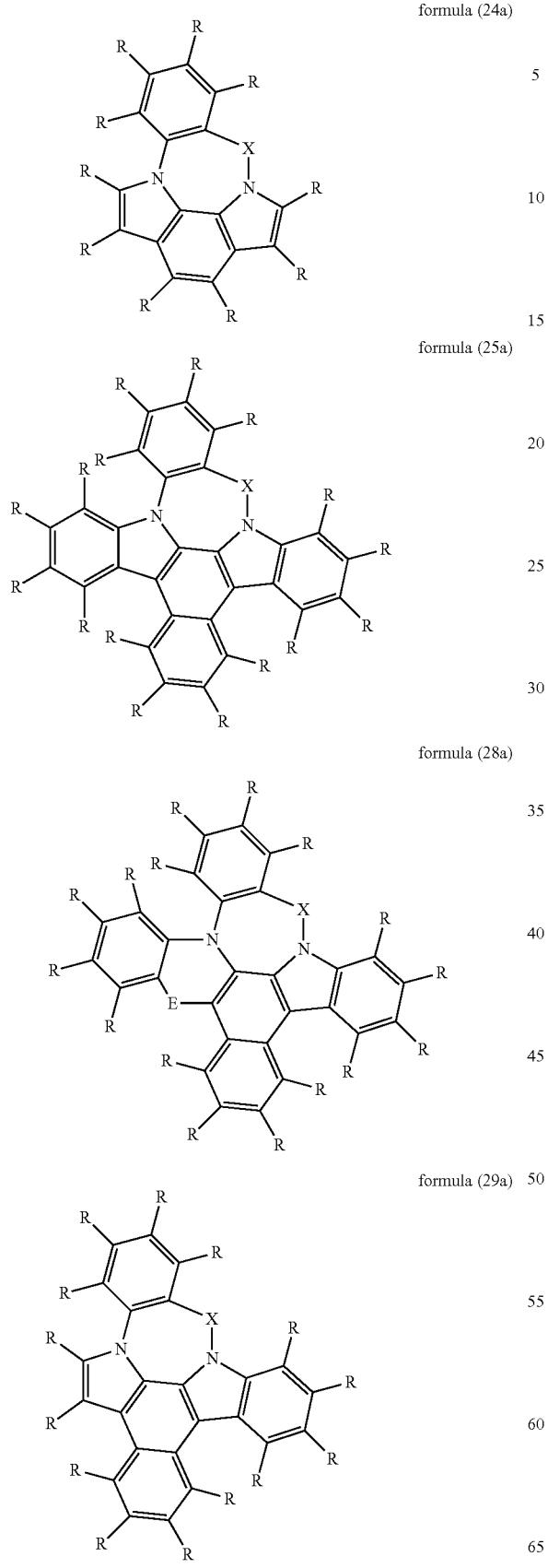

formula (34a)
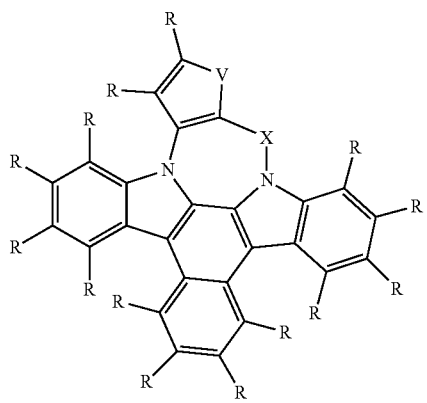
formula (15b)
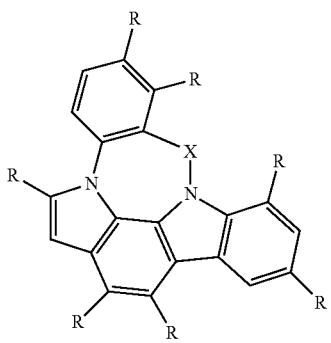
formula (37a)
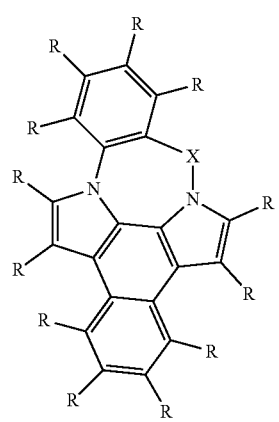
formula (16b)
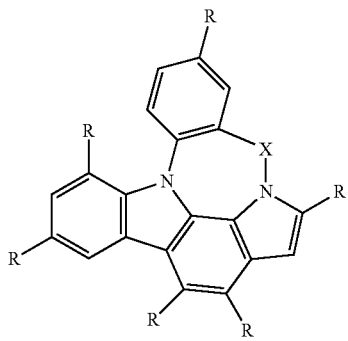
where the symbols used have the meanings given in claim 1.
7. The compound according to claim 1, wherein the compound is selected from the compounds of the following formulae (11 b) to (37b):
formula (11b)
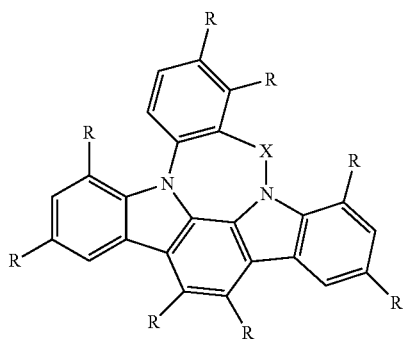
formula (17b)
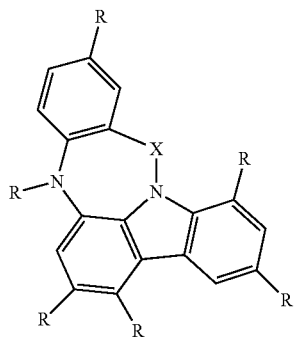
formula (14b)
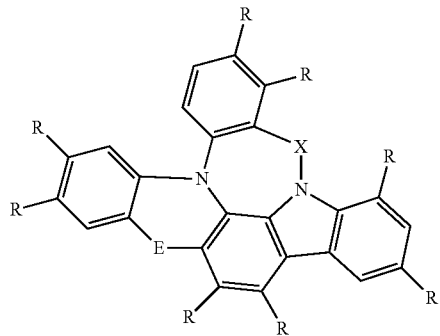
formula (18b)
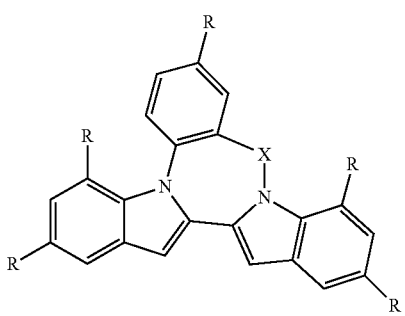

-continued
formula (19b)
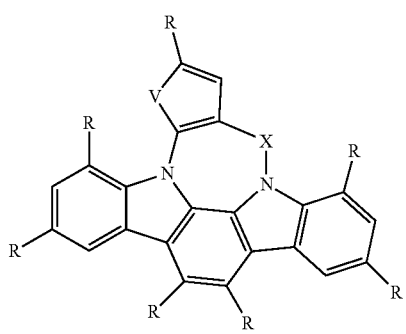
formula (20b)
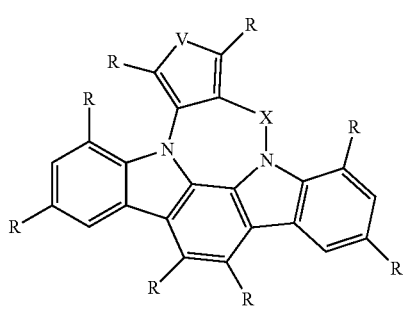
formula (21b)
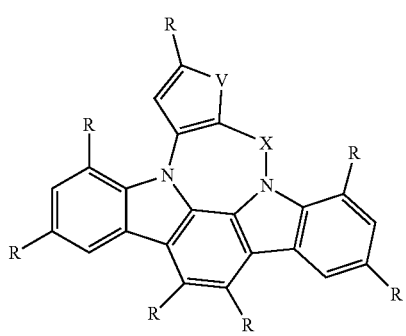
formula (24b)
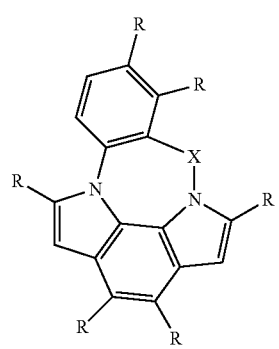
-continued
formula (25b)
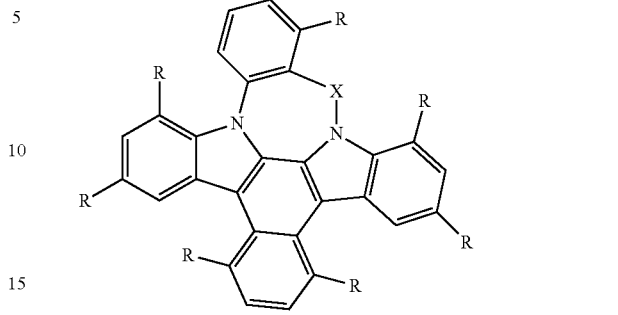
formula (27b)
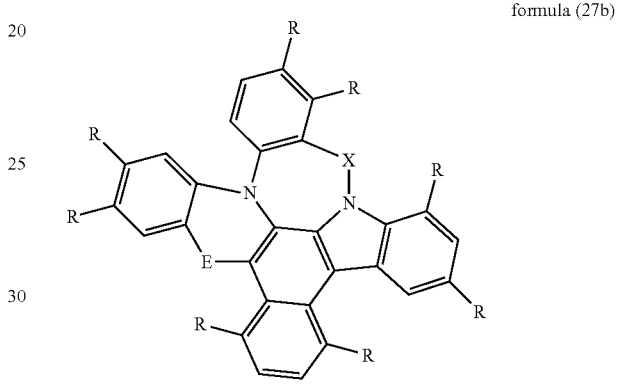
formula (29b)
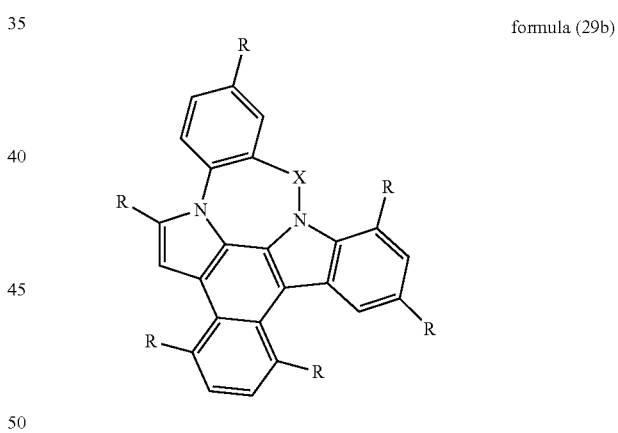
formula (30b)
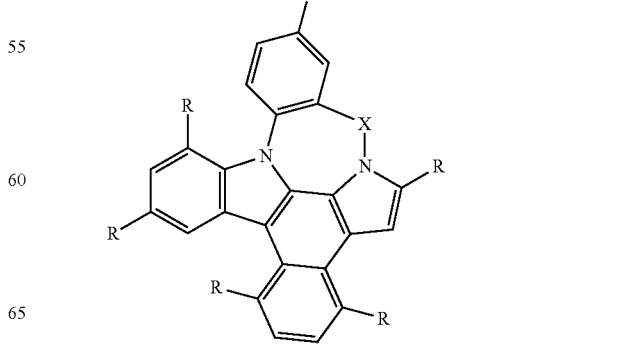

-continued formula (31b)
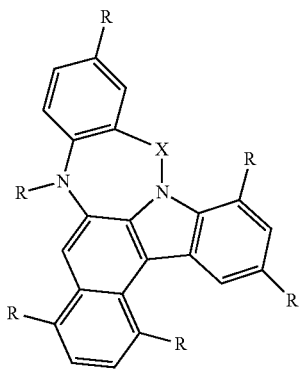

formula (32b)
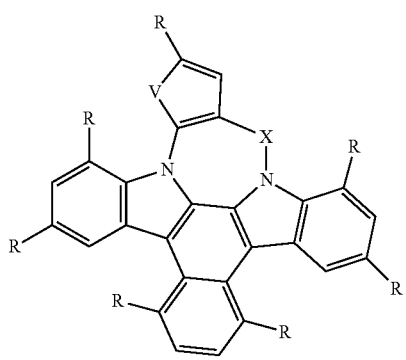

formula (33b)
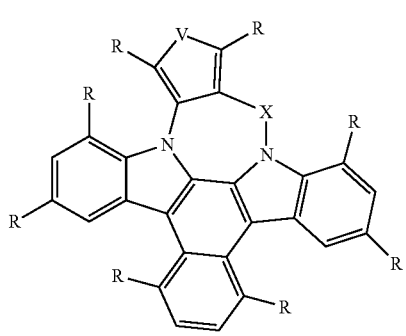

formula (34b)
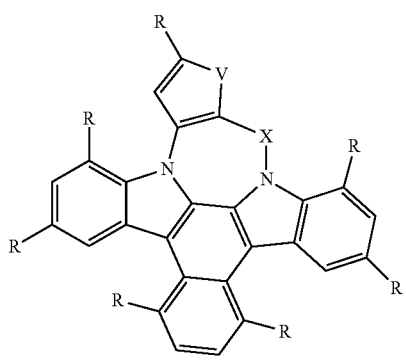

-continued formula (37b)
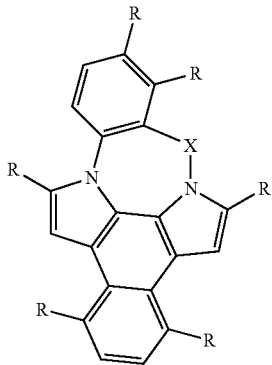

where the symbols used have the meanings given in claim 1.

8. The compound according to claim 5, wherein X stands for C=O or SO$_2$ and E stands for CR$_2$, C=O or NR.

9. The compound according to claim 1, wherein R is selected, identically or differently on each occurrence, from H, D, F, Cl, Br, CN, N(Ar$^1$)$_2$, C(=O)Ar$^1$, a straight-chain alkyl group having 1 to 10 C atoms or a branched or cyclic alkyl group having 3 to 10 C atoms or an alkenyl or alkynyl group having 2 to 10 C atoms, each of which is optionally substituted by one or more radicals R$^1$, where one or more non-adjacent CH$_2$ groups is optionally replaced by O and wherein one or more H atoms is optionally replaced by D or F, an aromatic or heteroaromatic ring system having 5 to 30 aromatic ring atoms, which may in each case be substituted by one or more radicals R$^1$, an aryloxy or heteroaryloxy group having 5 to 30 aromatic ring atoms, which is optionally substituted by one or more radicals R$^1$, or a combination of these systems.

10. A process for the preparation of the compound according to claim 1 which comprises reacting a cis-indolocarbazole derivative with an aryl or heteroaryl derivative which is substituted in the ortho-positions by halogen, and an acid derivative.

11. A process for the preparation of the compound according to claim 1 which comprises reacting a cis-indolocarbazole derivative with an aryl or heteroaryl derivative which is substituted in the ortho-positions by iodine, and an acid derivative, where the acid derivative which is a carboxylic acid ester, a carboxylic acid halide, a sulfonic acid halide, a phosphinyl halide or a phosphinyl oxyhalide.

12. The compound according to claim 1, wherein R is selected on each occurrence, identically or differently, from H, D, F, Cl, Br, I, CN, NO$_2$, N(Ar$^1$)$_2$, N(R$^1$)$_2$, C(=O)Ar$^1$, P(=O)(Ar$^1$)$_2$, a straight-chain alkyl or thioalkyl group having 1 to 40 C atoms or a branched or cyclic alkyl or thioalkyl group having 3 to 40 C atoms or an alkenyl or alkynyl group having 2 to 40 C atoms, each of which is optionally substituted by one or more radicals R$^1$, where one or more non-adjacent CH$_2$ groups is optionally replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, S or CONR$^1$ and where one or more H atoms is optionally replaced by D, F, Cl, Br, I, CN or NO$_2$, an aromatic or heteroaromatic ring system having 5 to 80 aromatic ring atoms, which is optionally in each case be substituted by one or more radicals R$^1$, an aryloxy or heteroaryloxy group having 5 to 60 aromatic ring atoms, which is optionally substituted by one or more radicals R$^1$, or a combination of these systems;

$R^1$ is selected on each occurrence, identically or differently, is H, D, F, Cl, Br, I, CN, $NO_2$, $N(Ar^1)_2$, $N(R^2)_2$, C(=O)Ar, C(=O)$R^2$, P(=O)$(Ar^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, C=$NR^2$, P(=O)($R^2$), SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 60 aromatic ring atoms, which is optionally in each case be substituted by one or more radicals $R^2$, an aryloxy or heteroaryloxy group having 5 to 60 aromatic ring atoms, which is optionally substituted by one or more radicals $R^2$, or a combination of these systems; and $R^2$ is selected from the group consisting of H, D, F, CN, an aliphatic hydrocarbon radical having 1 to 20 C atoms, an aromatic or hetero-aromatic ring system having 5 to 30 aromatic ring atoms, in which one or more H atoms is optionally replaced by D, F, Cl, Br, I or CN.

* * * * *